United States Patent
Polverino et al.

(10) Patent No.: US 7,629,144 B2
(45) Date of Patent: Dec. 8, 2009

(54) SECRETED EPITHELIAL COLON STROMAL-1 MOLECULES AND USES THEREOF

(75) Inventors: Anthony J. Polverino, Bainbridge Island, WA (US); Roland Luethy, Camarillo, CA (US)

(73) Assignee: Amgen Inc., Thousand Oaks, CA (US)

(*) Notice: Subject to any disclaimer, the term of this patent is extended or adjusted under 35 U.S.C. 154(b) by 181 days.

(21) Appl. No.: 11/364,871

(22) Filed: Feb. 28, 2006

(65) Prior Publication Data

US 2007/0059723 A1  Mar. 15, 2007

Related U.S. Application Data

(63) Continuation of application No. 09/599,087, filed on Jun. 21, 2000, now abandoned.

(51) Int. Cl.
*C12P 21/06* (2006.01)
(52) U.S. Cl. .......... 435/69.1; 536/23.1; 536/23.5; 530/300; 530/350; 435/320.1; 435/325
(58) Field of Classification Search ........... 536/23.1, 536/23.5; 435/320.1, 325, 69.1; 530/300, 530/350
See application file for complete search history.

(56) References Cited

U.S. PATENT DOCUMENTS

2003/0004311 A1* 1/2003 Baker et al. ............. 530/350
2007/0161034 A1* 7/2007 Jiang et al. .............. 435/6

FOREIGN PATENT DOCUMENTS

WO  00/43506  7/2000

OTHER PUBLICATIONS

Boehringer Mannheim Biochemicals, 1994 Catalog (No. 1034 731/1006 924), p. 93.*
Guo et al. (Proc. Natl. Acad. Sci. USA. Jun. 22, 2004; 101 (25): 9205-9210).*
Takada et al. (Mol. Endocrinol. 2000; 14 (5): 733-740).*
Vucic et al. (J. Biol. Chem. Dec. 18, 1998; 273 (51): 33915-33921).*
Luque et al. (Biochemistry. Nov. 19, 2002; 41(46): 13663-13671).*
Skolnick et al. (Trends in Biotechnology 2000; 18: 34-39).*
U.S. Appl. No. 09/599,087, filed Jun. 21, 2000, Polverion, AJ.
Hiller L et al. (Wash U-Merck EST Project) GenBank EST Database, Accession No. AA283751 (1997).
Hiller et al. (Wash U-Merck EST Project) GenBank EST Database, Accession No. AA422178 (1997).
The FAPESP/LICR Human Cancer Genome Project, GenBank EST Database, Accession No. AW351839 (1999).
Bergers G et al., "Extrinsic regulators of epithelial tumor progression." Current Opinions in Genetics and Development 10: 120-127 (2000).
EMBL Database Accession No. AI983767.
EMBL Database Accession No. AA238890.
EMBL Database Accession No. AA017989.
Hennigan et al., "Fos-transformation activates genes associated with invasion." Oncogene 9: 3591-3600 (1994).
Niwa H et al., "Efficient selection for high-expression transfectants with a novel eukaryotic vector." Gene 108(2): 193-199 (1991).
Bendig MM et al, "The production of foreign proteins in mammalian cells." Genet Eng 7: 91- 127 (1988).
Hiller L et al., "Generation and analysis of 280,000 human expressed sequence tags." Genome Research 6(9): 807-828 (1996).
Alberts et al., Molecular Biology of the Cell, Garland Publishing, Inc., pp. 5-7 (1994).
Houdebine LM, "Production of pharmaceutical proteins in transgenic animals." J Biotechnol. 34(3): 269-287 (1994).
Verma IM et al., "Gene therapy—promises, problems and prospects." Nature 389(6648): 239-42 (1997).
Amalfitano A et al., "Separating fact from fiction: assessing the potential of modified adenovirus vectors for use in human gene therapy." Current Gene Ther. 2: 111-133 (2002).
Pandha HS et al., "Oncological applications of gene therapy." Current Opinion in Investigational Drugs 1(1): 122-133 (2000).

* cited by examiner

*Primary Examiner*—Stephen L Rawlings
(74) *Attorney, Agent, or Firm*—John Lamerdin

(57) ABSTRACT

The present invention provides novel Secreted Epithelial Colon Stromal-1 (Secs-1) polypeptides and nucleic acid molecules encoding the same. The invention also provides vectors, host cells, selective binding agents, and methods for producing Secs-1 polypeptides. The invention further provides methods for the treatment, diagnosis, amelioration, or prevention of diseases associated with Secs-1 polypeptides.

8 Claims, 9 Drawing Sheets

Figure 1

```
gcttcctccc taggcgtgag actccggctc cttcact atg aga ctt cta gcc ctt    55
                                        Met Arg Leu Leu Ala Leu
                                         1               5 tcc ggt ctg ctc tgc atg ctg ctc ctc tgt ttc tgc att ttc tcc tca    103
Ser Gly Leu Leu Cys Met Leu Leu Leu Cys Phe Cys Ile Phe Ser Ser
         10              15                  20 gaa ggg aga aga cat cct gcc aag tcc ttg aaa ctc agg cgc tgc tgt    151
Glu Gly Arg Arg His Pro Ala Lys Ser Leu Lys Leu Arg Arg Cys Cys
         25              30                  35 cac cta tct cct aga tcc aag ctg aca acc tgg aaa gga aac cac aca    199
His Leu Ser Pro Arg Ser Lys Leu Thr Thr Trp Lys Gly Asn His Thr
         40              45                  50 agg ccc tgc aga ctc tgc aga aac aag cta cca gtc aag tca tgg gtg    247
Arg Pro Cys Arg Leu Cys Arg Asn Lys Leu Pro Val Lys Ser Trp Val
 55          60                  65                          70 gtg cct ggg gct ctc cca cag ata tag ggcctcctcc gcccagatga           294
Val Pro Gly Ala Leu Pro Gln Ile
                 75 agcgttgatg cccagatgtg gagacaccag aagcatacac actatgttgc cttgcccctt 354 gccaatgagc tgtgacactg gaatgcttca cttcagacat cagggcggat ggattgcaga 414 attccaagtc ctcattccaa aggtgtcacc aaccttcaga gtcactaagg tccaggctca 474 gcccacaagt caccatggct cctccagagt aaaagtccaa gattccacct gtgggagcta 534 cagatccaga gactttcaag ctgactagag tgcagagaag caagacctca gtgtgatcag 594 ccgagactac agcatcttgg gaaccctcag tcagccccaa accctaaca cttaaccact 654 ggtctccaaa ccaacacctg taacttccta atgaaatcat caggaggata ccaaaagaaa 714 taaaccataa atcagcatac acactaaaaa                                   744
```

Figure 2

```
ggaacgaggg aaaatctgcc ttctcacc atg agg ctt cta gtc ctt tcc agc    52
                                Met Arg Leu Leu Val Leu Ser Ser
                                 1               5 ctg ctc tgt atc ctg ctt ctc tgc ttc tcc atc ttc tcc aca gaa ggg   100
Leu Leu Cys Ile Leu Leu Leu Cys Phe Ser Ile Phe Ser Thr Glu Gly
     10              15              20 aag agg cgt cct gcc aag gcc tgg tca ggc agg aga acc agg ctc tgc   148
Lys Arg Arg Pro Ala Lys Ala Trp Ser Gly Arg Arg Thr Arg Leu Cys
 25              30              35              40 tgc cac cga gtc cct agc ccc aac tca aca aac ctg aaa gga cat cat   196
Cys His Arg Val Pro Ser Pro Asn Ser Thr Asn Leu Lys Gly His His
                 45              50              55 gtg agg ctc tgt aaa cca tgc aag ctt gag cca gag ccc cgc ctt tgg   244
Val Arg Leu Cys Lys Pro Cys Lys Leu Glu Pro Glu Pro Arg Leu Trp
             60              65              70 gtg gtg cct ggg gca ctc cca cag gtg tag cactcccaaa gcaagactcc     294
Val Val Pro Gly Ala Leu Pro Gln Val
         75              80 agacagcgga gaacctcatg cctggcacct gaggtaccca gcagcctcct gtctcccctt 354 tcagccttca cagcagtgag ctgcaatgtt ggagggcttc atctcgggct gcaaggaccc 414 tgggaaagtt ccagaactcc acgtccttgt ctcaattgtg ccatcaactt tcagagctat 474 catgagccaa cctcacccca cagggcctca gtcgccacca tgtgggcctc tccagtgcaa 534 accaccgagc attccaccat gaccggtcac agctacaaat ccagagacca tcaatcctgc 594 tagagtgcag ggtggcaagc acccaagggt ggctgaccaa gactgcagag tctcctccat 654 cttcaggtcc attcagcctc ctggcattta actaccagca tccagtggtc cccaaggaat 714 cccttcctag cctcctgaca tgagtctgct ggaaagagca tccaaacaaa caagtaataa 774 ataaataaat aaactcaatg cagacacaaa aa                               806
```

Figure 3

```
              1                                                                    50
rat Secs-1    MRLLTLSGLF FMLFLCLCVL SSEGRKRPAK F...PKLRPR CHLSPRSKPI
murine Secs-1 MRLLALSGLL CMLLLCFCIF SSEGRRHPAK S...LKLRRC CHLSPRSKLT
human Secs-1  MRLLVLSSLL CILLLCFSIF STEGKRRPAK AWSGRRTRLC CHRVPSPNST 51                                              81
rat Secs-1    TWKGNHTRPC RPCR.KLESN SWVVPGALPQ I
murine Secs-1 TWKGNHTRPC RLCRNKLPVK SWVVPGALPQ I
human Secs-1  NLKGHHVRLC KPCKLEPEPR LWVVPGALPQ V
```

Figure 4A

```
     0
446  ATGAGGCTTCTAGTCCTTTCCAGCCTGCTCTGTATCCTGCTTCTCTGCTTCTCCATCTTC
     ::::::::::::::::::::::::::::::::::::::::::::::::::::::::::::
  1  M  R  L  L  V  L  S  S  L  L  C  I  L  L  L  C  F  S  I  F

60           .         :         .         :         .         :
506  TCCACAGAAGGTAGGGCAGCCCCCAGGGTGCAGATCCCTGAGCAGGATTTCAGCATCTGG
     :::::::::.--------------------------------------------------
 21  S  T  E

120          .         :         .         :         .         :
566  GAAGACTCTGATCAGGATTTGTTGGAGGGCAGGCCTTGGNNNNNNNNNNNCGCGCGTACTT
     ------------------------------------------------------------

180          .         :         .         :         .         :
626  CCAGCCCCGTGGTGAAGACGAAAGAGGGCTCTTTCTCCTGAACCTATAGGTTTGGGGCTC
     ------------------------------------------------------------

240          .         :         .         :         .         :
686  AGGACTGCCTGCAGGTGGCTTGGGGGTTCCATTCACAGCCCCTGCACCCCCAAATACATA
     ------------------------------------------------------------

300          .         :         .         :         .         :
746  CCCAGCCTAAGTAAAGTGGTGTGTTCGCCATGCAAACACACATACAACCTCTCAGCTAGA
     ------------------------------------------------------------

360          .         :         .         :         .         :
806  TTACTGTGCTTAAGTCCTACCTATCTAGAATTTCTGGAGCCATTCTCTTGTACTTGTGTC
     ------------------------------------------------------------

420          .         :         .         :         .         :
866  ATGCTTGGAACAGAGTAAATTAGTGTTGGGCAAATGAATACATTAATTAGTAGACCATCT
     ------------------------------------------------------------

480          .         :         .         :         .         :
926  AAGTCTGAACATCCCAAAACCTCATGCCCAGAAAATATCCATGAGCAGCTGAAATGAAGG
     ------------------------------------------------------------

540          .         :         .         :         .         :
986  TGTGTGTGGTAGGGAGGTGGGGTATGTTTATGCATGTTTAGAAGGGGACACCATCTTTTT
     ------------------------------------------------------------

600          .         :         .         :         .         :
1046 ACCTCTATAGATATGAATATTTAGCTCTCTTGCCCTTTTTTCTTTTTTCTTTTTTTTTTT
     ------------------------------------------------------------

660          .         :         .         :         .         :
1106 TTTTTTGAGATGGAGTCTTGCTCTGTCACCCAGGCTGGAGTGCAGTGGCGCTATCTCAGC
     ------------------------------------------------------------

720          .         :         .         :         .         :
1166 TCACTGCAATCTCCGCCTCCTGGGTTCAAGCAATTCTCTGCCTCAGCCTCCCAAGTAGCT
     ------------------------------------------------------------
```

Figure 4B

```
780            .         :         .         :         .         :         .         :         .         :         .         :
1226  GAGATTACAGGTGCCCACCACCAAGCCCAGCTAATTTTTGTATTTTTAGTACAGACAGGT

840            .         :         .         :         .         :         .         :         .         :         .         :
1286  TTCACCATCTTGGCCAGGCTGGTCTTGAACTCCTAACCTCGTAATCCTCCCACCTCGGCC

900            .         :         .         :         .         :         .         :         .         :         .         :
1346  TCCCAAAGTGCTGGGATTACAGGCGTGAGCCACCATGCCTGGCTGCCTTTCTTGATTCAG

960            .         :         .         :         .         :         .         :         .         :         .         :
1406  ATAGCTGAGTGTTTCAATCCATTTTTCTCTTGTCTAACCCTCTAGAAACTGCCTACATTT

1020           .         :         .         :         .         :         .         :         .         :         .         :
1466  ATTTTTTGTTTTAGTGGTTATGGTTACTCAAACTTTTGGGTGGGGGGAGCTGGAGCTATA

1080           .         :         .         :         .         :         .         :         .         :         .         :
1526  GAAATATATAAAGAGAAGAAAAACACTCAATTCCATGATTCAAGAGTAGCCATGTTCAAC

1140           .         :         .         :         .         :         .         :         .         :         .         :
1586  ATTTTGTTTATTTCCTTGCATGTAGAATTTTTAAAAATTAATTGATGTACCTATATGTTC

1200           .         :         .         :         .         :         .         :         .         :         .         :
1646  AAGGTTATATCTTTTTTATTTATCACTATATATATTGTTATAATCACCCAAAATGCTTAT

1260           .         :         .         :         .         :         .         :         .         :         .         :
1706  GATTGAAGATATTCTGGAAGCATTTACAACCCAGTGTCAGCAGCAGCCATCTCTGAGTAG

1320           .         :         .         :         .         :         .         :         .         :         .         :
1766  TGGGATTATAACAAGTGTTTGTTTTACAAAGTTTCTGCGATGAAAATGTCCCACATATAT

1380           .         :         ..        :         .         :         .         :         .         :         .         :
1826  AATAAGGAAAACAGTGATTAGAATTCCTCATAAACACAGCCCGTGACATGCAATTTATCA

1440           .         :         .         :         .         :         .         :         .         :         .         :
1886  GACCTCTATTTTTGGACATGTTGGAGGTTGCCAGTGATACCCTAGTGACAATTAAATGAG

1500           .         :         .         :         .         :         .         :         .         :         .         :
1946  GATAGATACCTTCCCCCATAAAGTTTCCTATCCATTTAGGACTATCTGTAGCAAACTCTT
```

Figure 4C

```
1560         .    :    .    :    .    :    .    :    .    :    .    :
2006  GAAGTAGCATTAATCAACTAATATTTTCAGGTATAACTTGCTACAAGTGAACGTACTATG

1620         .    :    .    :    .    :    .    :    .    :    .    :
2066  ATGAATTTACATGCTTAGACATTTAGATAGTTCACAATTGTGTGCTTTTCCTTTTTTGAA

1680         .    :    .    :    .    :    .    :    .    :    .    :
2126  GCAAGATCTTGCTCTCTTGCCCAGGTCGGAGTGCAGTGGCATGACCACGGCTCAGTGCAG

1740         .    :    .    :    .    :    .    :    .    :    .    :
2186  GCTTGACTTCCAGGGCTCAAGCAATACTCGCACCTCAGGTTTTCCAGTAGCTGGGAAAAC

1800         .    :    .    :    .    :    .    :    .    :    .    :
2246  AGGTGCGCACCACAATGCCCTGCTAATTTTTAAAATTTTTTGCAGAGACGAGGTCTCTCT

1860         .    :    .    :    .    :    .    :    .    :    .    :
2306  AAGTTGCCCAGGCTGGTCTTGAACTTCTGGACTCAAGCCATCCTCCCACCTTGGCCTCCC

1920         .    :    .    :    .    :    .    :    .    :    .    :
2366  AGAGTGCTAGGATCACAGGCATGAGCCACCACACCTGGCCTACTTTGCACATTTTAATTA

1980         .    :    .    :    .    :    .    :    .    :    .    :
2426  TGTGGTAAAAGGTATATATGTACATAAAGTATGTCCTTTATTCAGGCTTTTTTTCTTTTT

2040         .    :    .    :    .    :    .    :    .    :    .    :
2486  TTCTTTTTTTTATTTTTTTGAGACGAAGTTTTTGCTCTTGTTGTCCAGGCTGGAGTGTAA

2100         .    :    .    :    .    :    .    :    .    :    .    :
2546  TGGCATGCTCTTGGCTCACCACAACCTCCGCCTCCCGGGTTCAAGTGATTCTCCTGCCTC

2160         .    :    .    :    .    :    .    :    .    :    .    :
2606  AACCTCCTGAGTAGCTGGGATTACAGGCATGCACCAACATGCCAGGCTGATTTTGTATTT

2220         .    :    .    :    .    :    .    :    .    :    .    :
2666  TTAGTAGAGATGGGGTTTCTCCATGTTGGTCAGGCTGGTCTCGAACACTCGACCTCAAGT

2280         .    :    .    :    .    :    .    :    .    :    .    :
2726  GATCCGCCCACCTCAGCCTCCCAAAGAGCTAGGATTACAGGCATGAGCCACCACACCCAG
```

Figure 4D

```
2340         .         :         .         :         .         :         .         :         .         :
2786  CTCAGGGCTTATTTTCTTAGGCTAGATTGCCAAGGGGAGAATTATTATGTCAAAGAAACT
      ------------------------------------------------------------

2400         .         :         .         :         .         :         .         :         .         :
2846  ACTTATTGGACAGGAATCTGAAAAGGATGTGTTTTGGGGCCATGTGTCTCCCAACATTGT
      ------------------------------------------------------------

2460         .         :         .         :         .         :         .         :         .         :
2906  TATTTCTGAAAAGTAAATCACAACAAGGCCCACTCTTTCCCTAGGACCTCTCGTAGCCTG
      ------------------------------------------------------------

2520         .         :         .         :         .         :         .         :         .         :
2966  GCTCATCCTGAGTTTCTCTGGATAAATATTCCTGAGCCCTGTGCCTTGGAAGGGGAAGCT
      ------------------------------------------------------------

2580         .         :         .         :         .         :         .         :         .         :
3026  CACTCACAGACAAGCCCACTAAAGACAGTCTCTCTTCCTTTGTGTCCACCCTCAGGGAAG
      ---------------------------------------------------------..:::
  25                                                               G  K

2640         .         :         .         :         .         :         .         :         .         :
3086  AGGCGTCCTGCCAAGGCCTGGTCAGGCAGGAGAACCAGGCTCTGCTGCCACCGAGTCCCT
      ::::::::::::::::::::::::::::::::::::::::::::::::::::::::::::
  26   R  R  P  A  K  A  W  S  G  R  R  T  R  L  C  C  H  R  V  P

2700         .         :         .         :         .         :         .         :         .         :
3146  AGCCCCAACTCAACAAACCTGAAAGGTAAGTACCCCCACCTCGTCCAGACTGTGGGGCAG
      :::::::::::::::.-------------------------------------------
  46   S  P  N  S  T  N  L  K

2760         .         :         .         :         .         :         .         :         .         :
3206  AAGTTCTACAGTGGCCATGGGACCAGCCACACACACTGATCAGCCCCCACCCATGGCTGG
      ------------------------------------------------------------

2820         .         :         .         :         .         :         .         :         .         :
3266  CATCAGGCTCTGGCTGGGAGGACATCTTTGTTTTGTTGATTAATTTGTTGACTCCCCCCC
      ------------------------------------------------------------

2880         .         :         .         :         .         :         .         :         .         :
3326  AAAAGTCAACAAATTAATCATTTTAAACTGAATACATTCTGCCATGGAAAAAAAGCAGGA
      ------------------------------------------------------------

2940         .         :         .         :         .         :         .         :         .         :
3386  TGCAATTAGCAGATGTTGTGTGGAAACACACTTACTTTAGGTGGAAGGTGTCTGAGCAGG
      ------------------------------------------------------------

3000         .         :         .         :         .         :         .         :         .         :
3446  TGACATTTATGAGACCTGGCTCATTTATGAGCCAGGAGCCTGGCTGAGGCCTGTGGAGGT
      ------------------------------------------------------------
```

Figure 4E

```
3060         .         :         .         :         .         :         .         :         .         :         .         :
3506 GGGGCATGCAGGCAGAGGAGGCAGCAAGGGTGAAGGGCAAGAGTGGGGTATGGAAGACAG
     ------------------------------------------------------------

3120         .         :         .         :         .         :         .         :         .         :         .         :
3566 ATGGTAGCAGGGCTTGAGAGGTACTCCCAGAAGCTAAGGACCAAAGCTGCCTGTGAACCC
     ------------------------------------------------------------

3180         .         :         .         :         .         :         .         :         .         :         .         :
3626 TGTGGACCTGGGGCACAGATCAGCATGCAGGTCACCAGCAGGGGAGTGGGCCTGAGGGTC
     ------------------------------------------------------------

3240         .         :         .         :         .         :         .         :         .         :         .         :
3686 CAGAGAGCCATAGCTTGGCAGGAGATAAGGCAGCCCCAGAGATGCCAGCAGGCAGCATCC
     ------------------------------------------------------------

3300         .         :         .         :         .         :         .         :         .         :         .         :
3746 AGGCTGCATGACCAGAACGAGGCCCAGAAGAGCAAGGCTGCCCTCTCCCTGAGGCCTGGG
     ------------------------------------------------------------

3360         .         :         .         :         .         :         .         :         .         :         .         :
3806 GACACTGGGAGGCCTGTGGCGGACAGGCCCAAGCTCAGGAGGGCTGCGGGCACCCAGTTC
     ------------------------------------------------------------

3420         .         :         .         :         .         :         .         :         .         :         .         :
3866 CCTGCACAGGGGCTGCAGGCCCAGAGCAGATATTCACTGGAGTTGCCCAGCCCAGGTGGA
     ------------------------------------------------------------

3480         .         :         .         :         .         :         .         :         .         :         .         :
3926 AGGGTCAGGCTGCTGGAGCTTGGGTAGGGCAGGCAGATCCCCAAGGGGAGACTGTGGACC
     ------------------------------------------------------------

3540         .         :         .         :         .         :         .         :         .         :         .         :
3986 CTGAGTCAGACAGCCTGACACCAACCTGGGGCTCCTGCCTGAACTCTGCAGCCCCAGTGC
     ------------------------------------------------------------

3600         .         :         .         :         .         :         .         :         .         :         .         :
4046 CCACTCTCAAGAGGCTGAGGAGGTCCCGGCCCCACTTGCTCCTCTGCGGCCATGGCCCAT
     ------------------------------------------------------------

3660         .         :         .         :         .         :         .         :         .         :         .         :
4106 GGGGTCCATGACCAGCGCCGGAGCCTCCATGCCTTTCCCAGCTACCAAGGGGATGCTCAG
     ------------------------------------------------------------

3720         .         :         .         :         .         :         .         :         .         :         .         :
4166 CTGTGATGCAGGAGAGGGATAGAGGGAGGAAGCAAGACAGCATGACTCCAGCCGCAGACC
     ------------------------------------------------------------

3780         .         :         .         :         .         :         .         :         .         :         .         :
4226 TTCTCCCGGAGATGCTGACAGCCCTTTCTTCCAAACTGGCATCACACCCAGCCGGCCAGG
     ------------------------------------------------------------
```

Figure 4F

```
3840             .    :    .    :    .    :    .    :    .    :    .    :
4286  ATAAAAATAACCAGCTCGTCTTCACCACGGGCTGAAGGATCCCNNNNNNNNNNNNCACGAAA
      ------------------------------------------------------------

3900             .    :    .    :    .    :    .    :    .    :    .    :
4346  AGCCCCTTCTGGGCCTCCAGGGAAAAGCATAAGATCTAATTCTTGCTTTGAAATTTTTTT
      ------------------------------------------------------------

3960             .    :    .    :    .    :    .    :    .    :    .    :
4406  TTAAATGTGTTTGAAAATGCAACTTAATTGTGTTTTCCTCTCTCTCCCCACAACCTGGCT
      ------------------------------------------------------------

4020             .    :    .    :    .    :    .    :    .    :    .    :
4466  CTGACCTCGCCATCTTCCTGTCCTTGTCCCTCTTGTCTACTCATTGCTCCTCCCAGGACA
      ----------------------------------------------------..::
  55                                                          G  H

4080             .    :    .    :    .    :    .    :    .    :    .    :
4526  TCATGTGAGGCTCTGTAAACCATGCAAGCTTGAGCCAGAGCCCCGCCTTTGGGTGGTGCC
      :::::::::::::::::::::::::::::::::::::::::::::::::::::::::::
  56   H   V   R   L   C   K   P   C   K   L   E   P   E   P   R   L   W   V   V   P

4140             .    :    .
4586  TGGGGCACTCCCACAGGTG
      :::::::::::::::::::
  76   G   A   L   P   Q   V
```

US 7,629,144 B2

SECRETED EPITHELIAL COLON STROMAL-1 MOLECULES AND USES THEREOF

This application is a continuation of U.S. Application Ser. No. 09/599,087 filed Jun. 21, 2000, now abandoned.

FIELD OF THE INVENTION

The present invention relates to novel Secreted Epithelial Colon Stromal-1 (Secs-1) polypeptides and nucleic acid molecules encoding the same. The invention also relates to vectors, host cells, pharmaceutical compositions, selective binding agents, and methods for producing Secs-1 polypeptides. The invention further relates to methods for the diagnosis, treatment, amelioration, and/or prevention of diseases associated with Secs-1 polypeptides.

BACKGROUND OF THE INVENTION

Technical advances in the identification, cloning, expression, and manipulation of nucleic acid molecules and the deciphering of the human genome have greatly accelerated the discovery of novel therapeutics. Rapid nucleic acid sequencing techniques can now generate sequence information at unprecedented rates and, coupled with computational analyses, allow the assembly of overlapping sequences into partial and entire genomes and the identification of polypeptide-encoding regions. A comparison of a predicted amino acid sequence against a database compilation of known amino acid sequences allows one to determine the extent of homology to previously identified sequences and/or structural landmarks. The cloning and expression of a polypeptide-encoding region of a nucleic acid molecule provides a polypeptide product for structural and functional analyses. The manipulation of nucleic acid molecules and encoded polypeptides may confer advantageous properties on a product for use as a therapeutic.

In spite of the significant technical advances in genome research over the past decade, the potential for the development of novel therapeutics based on the human genome is still largely unrealized. Many genes encoding potentially beneficial polypeptide therapeutics or those encoding polypeptides, which may act as "targets" for therapeutic molecules, have still not been identified.

Accordingly, it is an object of the invention to identify novel polypeptides, and nucleic acid molecules encoding the same, which have diagnostic or therapeutic benefit.

SUMMARY OF THE INVENTION

The present invention relates to novel Secs-1 nucleic acid molecules and encoded polypeptides.

The invention provides for an isolated nucleic acid molecule comprising a nucleotide sequence selected from the group consisting of:

(a) the nucleotide sequence as set forth in SEQ ID NO: 1 or SEQ ID NO: 4;

(b) the nucleotide sequence of the DNA insert in ATCC Deposit Nos. PTA-1753 or PTA-1755;

(c) a nucleotide sequence encoding the polypeptide as set forth in SEQ ID NO: 2 or SEQ ID NO: 5;

(d) a nucleotide sequence which hybridizes under moderately or highly stringent conditions to the complement of any of (a)-(c); and (e) a nucleotide sequence complementary to any of (a)-(c).

The invention also provides for an isolated nucleic acid molecule comprising a nucleotide sequence selected from the group consisting of:

(a) a nucleotide sequence encoding a polypeptide that is at least about 70 percent identical to the polypeptide as set forth in SEQ ID NO: 2 or SEQ ID NO: 5 wherein the encoded polypeptide has an activity of the polypeptide set forth in SEQ ID NO: 2 or SEQ ID NO: 5;

(b) a nucleotide sequence encoding an allelic variant or splice variant of the nucleotide sequence as set forth in SEQ ID NO: 1 or SEQ ID NO: 4, the nucleotide sequence of the DNA insert in ATCC Deposit Nos. PTA-1753 or PTA-1755, or (a);

(c) a region of the nucleotide sequence of SEQ ID NO: 1, SEQ ID NO: 4, the DNA insert in ATCC Deposit Nos. PTA-1753 or PTA-1755, (a), or (b) encoding a polypeptide fragment of at least about 25 amino acid residues wherein the encoded polypeptide fragment has an activity of the polypeptide as set forth in SEQ ID NO: 2 or SEQ ID NO: 5, or is antigenic;

(d) a region of the nucleotide sequence of SEQ ID NO: 1, SEQ ID NO: 4, the DNA insert in ATCC Deposit Nos. PTA-1753 or PTA-1755, or any of (a)-(c) comprising a fragment of at least about 16 nucleotides;

(e) a nucleotide sequence which hybridizes under moderately or highly stringent conditions to the complement of any of (a)-(d); and (f) a nucleotide sequence complementary to any of (a)-(d).

The invention further provides for an isolated nucleic acid molecule comprising a nucleotide sequence selected from the group consisting of:

(a) a nucleotide sequence encoding a polypeptide as set forth in SEQ ID NO: 2 or SEQ ID NO: 5 with at least one conservative amino acid substitution and wherein the encoded polypeptide has an activity of the polypeptide as set forth in SEQ ID NO: 2 or SEQ ID NO: 5;

(b) a nucleotide sequence encoding a polypeptide as set forth in SEQ ID NO: 2 or SEQ ID NO: 5 with at least one amino acid insertion and wherein the encoded polypeptide has an activity of the polypeptide as set forth in SEQ ID NO: 2 or SEQ ID NO: 5;

(c) a nucleotide sequence encoding a polypeptide as set forth in SEQ ID NO: 2 or SEQ ID NO: 5 with at least one amino acid deletion and wherein the encoded polypeptide has an activity of the polypeptide as set forth in SEQ ID NO: 2or SEQ ID NO: 5;

(d) a nucleotide sequence encoding a polypeptide as set forth in SEQ ID NO: 2 or SEQ ID NO: 5 which has a C- and/or N-terminal truncation and wherein the encoded polypeptide has an activity of the polypeptide as set forth in SEQ ID NO: 2 or SEQ ID NO: 5;

(e) a nucleotide sequence encoding a polypeptide as set forth in SEQ ID NO: 2 or SEQ ID NO: 5 with at least one modification selected from the group consisting of amino acid substitutions, amino acid insertions, amino acid deletions, C-terminal truncation, and N-terminal truncation and wherein the encoded polypeptide has an activity of the polypeptide as set forth in SEQ ID NO: 2 or SEQ ID NO: 5;

(f) a region of the nucleotide sequence of any of (a)-(e) comprising a fragment of at least about 16 nucleotides;

(g) a nucleotide sequence which hybridizes under moderately or highly stringent conditions to the complement of any of (a)-(f); and (h) a nucleotide sequence complementary to any of (a)-(e).

The present invention provides for an isolated polypeptide comprising the amino acid sequence selected from the group consisting of:

(a) the amino acid sequence as set forth in SEQ ID NO: 2 or SEQ ID NO: 5; and (b) the amino acid sequence encoded by the DNA insert of ATCC Deposit Nos. PTA-1753 or PTA-1755.

The invention also provides for an isolated polypeptide comprising the amino acid sequence selected from the group consisting of:

(a) the amino acid sequence as set forth in SEQ ID NO: 3 or SEQ ID NO: 6, optionally further comprising an amino-terminal methionine;

(b) an amino acid sequence for an ortholog of SEQ ID NO: 2 or SEQ ID NO: 5;

(c) an amino acid sequence that is at least about 70 percent identical to the amino acid sequence of SEQ ID NO: 2 or SEQ ID NO: 5 wherein the polypeptide has an activity of the polypeptide as set forth in SEQ ID NO: 2 or SEQ ID NO: 5;

(d) a fragment of the amino acid sequence set forth in SEQ ID NO: 2 or SEQ ID NO: 5 comprising at least about 25 amino acid residues wherein the fragment has an activity of the polypeptide as set forth in SEQ ID NO: 2 or SEQ ID NO: 5, or is antigenic; and (e) an amino acid sequence for an allelic variant or splice variant of the amino acid sequence as set forth in SEQ ID NO: 2 or SEQ ID NO: 5, the amino acid sequence encoded by the DNA insert of ATCC Deposit Nos. PTA-1753 or PTA-1755, or any of (a)-(c).

The invention further provides for an isolated polypeptide comprising the amino acid sequence selected from the group consisting of:

(a) the amino acid sequence as set forth in SEQ ID NO: 2 or SEQ ID NO: 5 with at least one conservative amino acid substitution and wherein the polypeptide has an activity of the polypeptide as set forth in SEQ ID NO: 2 or SEQ ID NO: 5;

(b) the amino acid sequence as set forth in SEQ ID NO: 2 or SEQ ID NO: 5 with at least one amino acid insertion and wherein the polypeptide has an activity of the polypeptide as set forth in SEQ ID NO: 2 or SEQ ID NO: 5;

(c) the amino acid sequence as set forth in SEQ ID NO: 2 or SEQ ID NO: 5 with at least one amino acid deletion and wherein the polypeptide has an activity of the polypeptide as set forth in SEQ ID NO: 2 or SEQ ID NO: 5;

(d) the amino acid sequence as set forth in SEQ ID NO: 2 or SEQ ID NO: 5 which has a C- and/or N-terminal truncation and wherein the polypeptide has an activity of the polypeptide as set forth in SEQ ID NO: 2 or SEQ ID NO: 5; and (e) the amino acid sequence as set forth in SEQ ID NO: 2 or SEQ ID NO: 5 with at least one modification selected from the group consisting of amino acid substitutions, amino acid insertions, amino acid deletions, C-terminal truncation, and N-terminal truncation and wherein the polypeptide has an activity of the polypeptide as set forth in SEQ ID NO: 2 or SEQ ID NO: 5.

Also provided are fusion polypeptides comprising the amino acid sequences of (a)-(e) above.

The present invention also provides for an expression vector comprising the isolated nucleic acid molecules as set forth herein, recombinant host cells comprising the recombinant nucleic acid molecules as set forth herein, and a method of producing a Secs-1 polypeptide comprising culturing the host cells and optionally isolating the polypeptide so produced.

A transgenic non-human animal comprising a nucleic acid molecule encoding a Secs-1 polypeptide is also encompassed by the invention. The Secs-1 nucleic acid molecules are introduced into the animal in a manner that allows expression and increased levels of a Secs-1 polypeptide, which may include increased circulating levels. Alternatively, the Secs-1 nucleic acid molecules are introduced into the animal in a manner that prevents expression of endogenous Secs-1 polypeptide (i.e., generates a transgenic animal possessing a Secs-1 polypeptide gene knockout). The transgenic non-human animal is preferably a mammal, and more preferably a rodent, such as a rat or a mouse.

Also provided are derivatives of the Secs-1 polypeptides of the present invention.

Additionally provided are selective binding agents such as antibodies and peptides capable of specifically binding the Secs-1 polypeptides of the invention. Such antibodies and peptides may be agonistic or antagonistic.

Pharmaceutical compositions comprising the nucleotides, polypeptides, or selective binding agents of the invention and one or more pharmaceutically acceptable formulation agents are also encompassed by the invention. The pharmaceutical compositions are used to provide therapeutically effective amounts of the nucleotides or polypeptides of the present invention. The invention is also directed to methods of using the polypeptides, nucleic acid molecules, and selective binding agents.

The Secs-1 polypeptides and nucleic acid molecules of the present invention may be used to treat, prevent, ameliorate, and/or detect diseases and disorders, including those recited herein.

The present invention also provides a method of assaying test molecules to identify a test molecule that binds to a Secs-1 polypeptide. The method comprises contacting a Secs-1 polypeptide with a test molecule to determine the extent of binding of the test molecule to the polypeptide. The method further comprises determining whether such test molecules are agonists or antagonists of a Secs-1 polypeptide. The present invention further provides a method of testing the impact of molecules on the expression of Secs-1 polypeptide or on the activity of Secs-1 polypeptide.

Methods of regulating expression and modulating (i.e., increasing or decreasing) levels of a Secs-1 polypeptide are also encompassed by the invention. One method comprises administering to an animal a nucleic acid molecule encoding a Secs-1 polypeptide. In another method, a nucleic acid molecule comprising elements that regulate or modulate the expression of a Secs-1 polypeptide may be administered. Examples of these methods include gene therapy, cell therapy, and anti-sense therapy as further described herein.

Surprisingly, Secs-1 polypeptide was differentially expressed in epithelial cells, specifically epithelial cells of the cheek, tongue, esophagus, large intestine, uterus, thymus, nipple, skin, and nasal cavity. Therefore, the present polypeptide and its useful nucleic acid intermediates have demonstrated utility in differentiating this cell type from the background.

In another aspect of the present invention, the Secs-1 polypeptides may be used for identifying receptors thereof ("Secs-1 polypeptide receptors"). Various forms of "expression cloning" have been extensively used to clone receptors for protein ligands. See, e.g., Simonsen and Lodish, 1994, *Trends Pharmacol. Sci.* 15:437-41 and Tartaglia et al., 1995, *Cell* 83:1263-71. The isolation of a Secs-1 polypeptide receptor is useful for identifying or developing novel agonists and antagonists of the Secs-1 polypeptide signaling pathway. Such agonists and antagonists include soluble Secs-1 polypeptide receptors, anti-Secs-1 polypeptide receptor-selective binding agents (such as antibodies and derivatives thereof), small molecules, and antisense oligonucleotides, any of which can be used for treating one or more disease or disorder, including those disclosed herein.

BRIEF DESCRIPTION OF THE FIGURES

FIG. 1 illustrates the nucleotide sequence of the murine Secs-1 gene (SEQ ID NO: 1) and the deduced amino acid sequence of murine Secs-1 polypeptide (SEQ ID NO: 2). The predicted signal peptide is indicated (underline);

FIG. 2 illustrates the nucleotide sequence of the human Secs-1 gene (SEQ ID NO: 4) and the deduced amino acid sequence of human Secs-1 polypeptide (SEQ ID NO: 5). The predicted signal peptide is indicated (underline);

FIG. 3 illustrates an amino acid sequence alignment of rat Secs-1 polypeptide (SEQ ID NO: 7), murine Secs-1 polypeptide (SEQ ID NO: 2), and human Secs-1 polypeptide (SEQ ID NO: 5);

FIGS. 4A-4F illustrate the genomic nucleotide sequence for human Secs-1 polypeptide (SEQ ID NO: 8). The location and deduced amino acid sequence of the exons (SEQ ID NOS: 9-11) are indicated.

DETAILED DESCRIPTION OF THE INVENTION

The section headings used herein are for organizational purposes only and are not to be construed as limiting the subject matter described. All references cited in this application are expressly incorporated by reference herein.

Definitions

The terms "Secs-1 gene" or "Secs-1 nucleic acid molecule" or "Secs-1 polynucleotide" refer to a nucleic acid molecule comprising or consisting of a nucleotide sequence as set forth in SEQ ID NO: 1 or SEQ ID NO: 4, a nucleotide sequence encoding the polypeptide as set forth in SEQ ID NO: 2 or SEQ ID NO: 5, a nucleotide sequence of the DNA insert in ATCC Deposit Nos. PTA-1753 or PTA-1755, and nucleic acid molecules as defined herein.

The term "Secs-1 polypeptide" refers to a polypeptide comprising the amino acid sequence of SEQ ID NO: 2 or SEQ ID NO: 5, and related polypeptides. Related polypeptides include: Secs-1 polypeptide allelic variants, Secs-1 polypeptide orthologs, Secs-1 polypeptide splice variants, Secs-1 polypeptide variants, and Secs-1 polypeptide derivatives, which possess at least one activity of the polypeptide as set forth in SEQ ID NO: 2 or SEQ ID NO: 5. Secs-1 polypeptides may be mature polypeptides, as defined herein, and may or may not have an amino terminal methionine residue, depending on the method by which they are prepared.

The term "Secs-1 polypeptide allelic variant" refers to one of several possible naturally occurring alternate forms of a gene occupying a given locus on a chromosome of an organism or a population of organisms.

The term "Secs-1 polypeptide derivatives" refers to, the polypeptide as set forth in SEQ ID NO: 2 or SEQ ID NO: 5, Secs-1 polypeptide allelic variants, Secs-1 polypeptide orthologs, Secs-1 polypeptide splice variants, or Secs-1 polypeptide variants, as defined herein, that have been chemically modified.

The term "Secs-1 polypeptide fragment" refers to a polypeptide that comprises a truncation at the amino terminus (with or without a leader sequence) and/or a truncation at the carboxy terminus of the polypeptide as set forth in SEQ ID NO: 2 or SEQ ID NO: 5, Secs-1 polypeptide allelic variants, Secs-1 polypeptide orthologs, Secs-1 polypeptide splice variants and/or a Secs-1 polypeptide variant having one or more amino acid additions or substitutions or internal deletions (wherein the resulting polypeptide is at least six (6) amino acids or more in length) as compared to the Secs-1 polypeptide amino acid sequence set forth in SEQ ID NO: 2 or SEQ ID NO: 5. Secs-1 polypeptide fragments may result from alternative RNA splicing or from in vivo protease activity. Membrane-bound forms of a Secs-1 polypeptide are also contemplated by the present invention. In preferred embodiments, truncations and/or deletions comprise about 10 amino acids, or about 20 amino acids, or about 30 amino acids, or about 40 amino acids, or about 50 amino acids, or more than about 50 amino acids. The polypeptide fragments so produced will comprise about 25 contiguous amino acids, or about 30 amino acids, or about 40 amino acids, or about 50 amino acids, or about 60 amino acids, or about 70 amino acids. Such Secs-1 polypeptide fragments may optionally comprise an amino terminal methionine residue. It will be appreciated that such fragments can be used, for example, to generate antibodies to Secs-1 polypeptides.

The term "Secs-1 fusion polypeptide" refers to a fusion of one or more amino acids (such as a heterologous peptide or polypeptide) at the amino or carboxy terminus of the polypeptide as set forth in SEQ ID NO: 2 or SEQ ID NO: 5, Secs-1 polypeptide allelic variants, Secs-1 polypeptide orthologs, Secs-1 polypeptide splice variants, or Secs-1 polypeptide variants having one or more amino acid deletions, substitutions or internal additions as compared to the Secs-1 polypeptide amino acid sequence set forth in SEQ ID NO: 2 or SEQ ID NO: 5.

The term "Secs-1 polypeptide ortholog" refers to a polypeptide from another species that corresponds to Secs-1 polypeptide amino acid sequence as set forth in SEQ ID NO: 2 or SEQ ID NO: 5. For example, mouse and human Secs-1 polypeptides are considered orthologs of each other.

The term "Secs-1 polypeptide splice variant" refers to a nucleic acid molecule, usually RNA, which is generated by alternative processing of intron sequences in an RNA transcript of Secs-1 polypeptide amino acid sequence as set forth in SEQ ID NO: 2 or SEQ ID NO: 5.

The term "Secs-1 polypeptide variants" refers to Secs-1 polypeptides comprising amino acid sequences having one or more amino acid sequence substitutions, deletions (such as internal deletions and/or Secs-1 polypeptide fragments), and/or additions (such as internal additions and/or Secs-1 fusion polypeptides) as compared to the Secs-1 polypeptide amino acid sequence set forth in SEQ ID NO: 2 or SEQ ID NO: 5 (with or without a leader sequence). Variants may be naturally occurring (e.g., Secs-1 polypeptide allelic variants, Secs-1 polypeptide orthologs, and Secs-1 polypeptide splice variants) or artificially constructed. Such Secs-1 polypeptide variants may be prepared from the corresponding nucleic acid molecules having a DNA sequence that varies accordingly from the DNA sequence as set forth in SEQ ID NO: 1 or SEQ ID NO: 4. In preferred embodiments, the variants have from 1 to 3, or from 1 to 5, or from 1 to 10, or from 1 to 15, or from 1 to 20, or from 1 to 25, or from 1 to 30, or from 1 to 40, or from 1 to 50, or more than 50 amino acid substitutions, insertions, additions and/or deletions, wherein the substitutions may be conservative, or non-conservative, or any combination thereof.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "biologically active Secs-1 polypeptides" refers to Secs-1 polypeptides having at least one activity characteristic of the polypeptide comprising the amino acid sequence of SEQ ID NO: 2 or SEQ ID NO: 5.

The terms "effective amount" and "therapeutically effective amount" each refer to the amount of a Secs-1 polypeptide or Secs-1 nucleic acid molecule used to support an observable level of one or more biological activities of the Secs-1 polypeptides as set forth herein.

The term "vector" is used to refer to any molecule (e.g., nucleic acid, plasmid, or virus) used to transfer coding information to a host cell.

The term "expression vector" refers to a vector that is suitable for transformation of a host cell and contains nucleic acid sequences that direct and/or control the expression of inserted heterologous nucleic acid sequences. Expression includes, but is not limited to, processes such as transcription, translation, and RNA splicing, if introns are present.

The term "host cell" is used to refer to a cell which has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

The term "identity," as known in the art, refers to a relationship between the sequences of two or more polypeptide molecules or two or more nucleic acid molecules, as determined by comparing the sequences. In the art, "identity" also means the degree of sequence relatedness between nucleic acid molecules or polypeptides, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms").

The term "similarity" is a related concept, but in contrast to "identity," "similarity" refers to a measure of relatedness which includes both identical matches and conservative substitution matches. If two polypeptide sequences have, for example, 10/20 identical amino acids, and the remainder are all non-conservative substitutions, then the percent identity and similarity would both be 50%. If in the same example, there are five more positions where there are conservative substitutions, then the percent identity remains 50%, but the percent similarity would be 75% (15/20). Therefore, in cases where there are conservative substitutions, the percent similarity between two polypeptides will be higher than the percent identity between those two polypeptides.

The term "isolated nucleic acid molecule" refers to a nucleic acid molecule of the invention that (1) has been separated from at least about 50 percent of proteins, lipids, carbohydrates, or other materials with which it is naturally found when total nucleic acid is isolated from the source cells, (2) is not linked to all or a portion of a polynucleotide to which the "isolated nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecule(s) or other contaminants that are found in its natural environment that would interfere with its use in polypeptide production or its therapeutic, diagnostic, prophylactic or research use.

The term "isolated polypeptide" refers to a polypeptide of the present invention that (1) has been separated from at least about 50 percent of polynucleotides, lipids, carbohydrates, or other materials with which it is naturally found when isolated from the source cell, (2) is not linked (by covalent or noncovalent interaction) to all or a portion of a polypeptide to which the "isolated polypeptide" is linked in nature, (3) is operably linked (by covalent or noncovalent interaction) to a polypeptide with which it is not linked in nature, or (4) does not occur in nature. Preferably, the isolated polypeptide is substantially free from any other contaminating polypeptides or other contaminants that are found in its natural environment that would interfere with its therapeutic, diagnostic, prophylactic or research use.

The term "mature Secs-1 polypeptide" refers to a Secs-1 polypeptide lacking a leader sequence. A mature Secs-1 polypeptide may also include other modifications such as proteolytic processing of the amino terminus (with or without a leader sequence) and/or the carboxy terminus, cleavage of a smaller polypeptide from a larger precursor, N-linked and/or O-linked glycosylation, and the like. An exemplary mature Secs-1 polypeptide is depicted by the amino acid sequence of SEQ ID NO: 3 or SEQ ID NO: 6.

The term "nucleic acid sequence" or "nucleic acid molecule" refers to a DNA or RNA sequence. The term encompasses molecules formed from any of the known base analogs of DNA and RNA such as, but not limited to 4-acetylcytosine, 8-hydroxy-N6-methyladenosine, aziridinyl-cytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-iso-pentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" as used herein refers to a material that is not found in nature or that has been structurally modified or synthesized by man.

The term "operably linked" is used herein to refer to an arrangement of flanking sequences wherein the flanking sequences so described are configured or assembled so as to perform their usual function. Thus, a flanking sequence operably linked to a coding sequence may be capable of effecting the replication, transcription and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

The term "pharmaceutically acceptable carrier" or "physiologically acceptable carrier" as used herein refers to one or more formulation materials suitable for accomplishing or enhancing the delivery of the Secs-1 polypeptide, Secs-1 nucleic acid molecule, or Secs-1 selective binding agent as a pharmaceutical composition.

The term "selective binding agent" refers to a molecule or molecules having specificity for a SECS-1 polypeptide. As used herein, the terms, "specific" and "specificity" refer to the ability of the selective binding agents to bind to human Secs-1 polypeptides and not to bind to human non-Secs-1 polypeptides. It will be appreciated, however, that the selective binding agents may also bind orthologs of the polypeptide as set forth in SEQ ID NO: 2 or SEQ ID NO: 5, that is, interspecies versions thereof, such as mouse and rat polypeptides.

The term "transduction" is used to refer to the transfer of genes from one bacterium to another, usually by a phage. "Transduction" also refers to the acquisition and transfer of eukaryotic cellular sequences by retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52:456; Sambrook et al., *Molecular Cloning, A Laboratory Manual* (Cold Spring Harbor Laboratories, 1989); Davis et al., *Basic Methods in Molecular Biology* (Elsevier, 1986); and Chu et al., 1981, *Gene* 13:197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, may be maintained transiently as an episomal element without being replicated, or may replicate independently as a plasmid. A cell is considered to have been stably transformed when the DNA is replicated with the division of the cell.

Relatedness of Nucleic Acid Molecules and/or Polypeptides

It is understood that related nucleic acid molecules include allelic or splice variants of the nucleic acid molecule of SEQ ID NO: 1 or SEQ ID NO: 4, and include sequences which are complementary to any of the above nucleotide sequences. Related nucleic acid molecules also include a nucleotide sequence encoding a polypeptide comprising or consisting essentially of a substitution, modification, addition and/or deletion of one or more amino acid residues compared to the polypeptide in SEQ ID NO: 2 or SEQ ID NO: 5.

Related nucleic acid molecules also include fragments of Secs-1 nucleic acid molecules which encode a polypeptide of at least about 25 amino acid residues, or about 30, or about 40, or about 50, or about 60, or about 70, or greater than about 70 amino acid residues of the Secs-1 polypeptide of SEQ ID NO: 2 or SEQ ID NO: 5.

In addition, related Secs-1 nucleic acid molecules also include those molecules which comprise nucleotide sequences which hybridize under moderately or highly stringent conditions as defined herein with the fully complementary sequence of the Secs-1 nucleic acid molecule of SEQ ID NO: 1 or SEQ ID NO: 4, or of a molecule encoding a polypeptide, which polypeptide comprises the amino acid sequence as shown in SEQ ID NO: 2 or SEQ ID NO: 5, or of a nucleic acid fragment as defined herein, or of a nucleic acid fragment encoding a polypeptide as defined herein. Hybridization probes may be prepared using the Secs-1 sequences provided herein to screen cDNA, genomic or synthetic DNA libraries for related sequences. Regions of the DNA and/or amino acid sequence of Secs-1 polypeptide that exhibit significant identity to known sequences are readily determined using sequence alignment algorithms as described herein and those regions may be used to design probes for screening.

The term "highly stringent conditions" refers to those conditions that are designed to permit hybridization of DNA strands whose sequences are highly complementary, and to exclude hybridization of significantly mismatched DNAs. Hybridization stringency is principally determined by temperature, ionic strength, and the concentration of denaturing agents such as formamide. Examples of "highly stringent conditions" for hybridization and washing are 0.015 M sodium chloride, 0.0015 M sodium citrate at 65-68° C. or 0.015 M sodium chloride, 0.0015 M sodium citrate, and 50% formamide at 42° C. See Sambrook, Fritsch & Maniatis, *Molecular Cloning: A Laboratory Manual* (2nd ed., Cold Spring Harbor Laboratory, 1989); Anderson et al., *Nucleic Acid Hybridisation: A Practical Approach* Ch. 4 (IRL Press Limited).

More stringent conditions (such as higher temperature, lower ionic strength, higher formamide, or other denaturing agent) may also be used—however, the rate of hybridization will be affected. Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, $NaDodSO_4$, (SDS), ficoll, Denhardt's solution, sonicated salmon sperm DNA (or another non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4; however, at typical ionic strength conditions, the rate of hybridization is nearly independent of pH. See Anderson et al., *Nucleic Acid Hybridisation: A Practical Approach* Ch. 4 (IRL Press Limited).

Factors affecting the stability of DNA duplex include base composition, length, and degree of base pair mismatch. Hybridization conditions can be adjusted by one skilled in the art in order to accommodate these variables and allow DNAs of different sequence relatedness to form hybrids. The melting temperature of a perfectly matched DNA duplex can be estimated by the following equation:

$$T_m(° C.)=81.5+16.6(\log [Na+])+0.41(\% G+C)-600/N-0.72(\% \text{ formamide})$$

where N is the length of the duplex formed, [Na+] is the molar concentration of the sodium ion in the hybridization or washing solution, % G+C is the percentage of (guanine+cytosine) bases in the hybrid. For imperfectly matched hybrids, the melting temperature is reduced by approximately 1° C. for each 1% mismatch.

The term "moderately stringent conditions" refers to conditions under which a DNA duplex with a greater degree of base pair mismatching than could occur under "highly stringent conditions" is able to form. Examples of typical "moderately stringent conditions" are 0.015 M sodium chloride, 0.0015 M sodium citrate at 50-65° C. or 0.015 M sodium chloride, 0.0015 M sodium citrate, and 20% formamide at 37-50° C. By way of example, "moderately stringent conditions" of 50° C. in 0.015 M sodium ion will allow about a 21% mismatch.

It will be appreciated by those skilled in the art that there is no absolute distinction between "highly stringent conditions"

and "moderately stringent conditions." For example, at 0.015 M sodium ion (no formamide), the melting temperature of perfectly matched long DNA is about 71° C. With a wash at 65° C. (at the same ionic strength), this would allow for approximately a 6% mismatch. To capture more distantly related sequences, one skilled in the art can simply lower the temperature or raise the ionic strength.

A good estimate of the melting temperature in 1M NaCl* for oligonucleotide probes up to about 20 nt is given by:

*The sodium ion concentration in 6× salt sodium citrate (SSC) is 1M. See Suggs et al., *Developmental Biology Using Purified Genes* 683 (Brown and Fox, eds., 1981).

$$Tm = 2° C. \text{ per } A-T \text{ base pair} + 4° C. \text{ per } G-C \text{ base pair}$$

High stringency washing conditions for oligonucleotides are usually at a temperature of 0-5° C. below the Tm of the oligonucleotide in 6×SSC, 0.1% SDS.

In another embodiment, related nucleic acid molecules comprise or consist of a nucleotide sequence that is at least about 70 percent identical to the nucleotide sequence as shown in SEQ ID NO: 1 or SEQ ID NO: 4, or comprise or consist essentially of a nucleotide sequence encoding a polypeptide that is at least about 70 percent identical to the polypeptide as set forth in SEQ ID NO: 2 or SEQ ID NO: 5. In preferred embodiments, the nucleotide sequences are about 75 percent, or about 80 percent, or about 85 percent, or about 90 percent, or about 95, 96, 97, 98, or 99 percent identical to the nucleotide sequence as shown in SEQ ID NO: 1 or SEQ ID NO: 4, or the nucleotide sequences encode a polypeptide that is about 75 percent, or about 80 percent, or about 85 percent, or about 90 percent, or about 95, 96, 97, 98, or 99 percent identical to the polypeptide sequence as set forth in SEQ ID NO: 2 or SEQ ID NO: 5. Related nucleic acid molecules encode polypeptides possessing at least one activity of the polypeptide set forth in SEQ ID NO: 2 or SEQ ID NO: 5.

Differences in the nucleic acid sequence may result in conservative and/or non-conservative modifications of the amino acid sequence relative to the amino acid sequence of SEQ ID NO: 2 or SEQ ID NO: 5.

Conservative modifications to the amino acid sequence of SEQ ID NO: 2 or SEQ ID NO: 5 (and the corresponding modifications to the encoding nucleotides) will produce Secs-1 polypeptides having functional and chemical characteristics similar to those of a naturally occurring Secs-1 polypeptide. In contrast, substantial modifications in the functional and/or chemical characteristics of Secs-1 polypeptides may be accomplished by selecting substitutions in the amino acid sequence of SEQ ID NO: 2 or SEQ ID NO: 5 that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a nonnative residue such that there is little or no effect on the polarity or charge of the amino acid residue at that position. Furthermore, any native residue in the polypeptide may also be substituted with alanine, as has been previously described for "alanine scanning mutagenesis."

Conservative amino acid substitutions also encompass non-naturally occurring amino acid residues that are typically incorporated by chemical peptide synthesis rather than by synthesis in biological systems. These include peptidomimetics, and other reversed or inverted forms of amino acid moieties.

Naturally occurring residues may be divided into classes based on common side chain properties:
1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

For example, non-conservative substitutions may involve the exchange of a member of one of these classes for a member from another class. Such substituted residues may be introduced into regions of the human Secs-1 polypeptide that are homologous with non-human Secs-1 polypeptides, or into the non-homologous regions of the molecule.

In making such changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al., 1982, *J. Mol. Biol.* 157:105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological embodiments, as in the present case. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0 ±1); glutamate (+3.0 ±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those which are within ±1 are particularly preferred, and those within ±0.5 are even more particularly preferred. One may also identify epitopes from primary amino acid sequences on the basis of hydrophilicity. These regions are also referred to as "epitopic core regions."

Desired amino acid substitutions (whether conservative or non-conservative) can be determined by those skilled in the art at the time such substitutions are desired. For example, amino acid substitutions can be used to identify important residues of the Secs-1 polypeptide, or to increase or decrease the affinity of the Secs-1 polypeptides described herein. Exemplary amino acid substitutions are set forth in Table I.

TABLE I

Amino Acid Substitutions

| Original Residues | Exemplary Substitutions | Preferred Substitutions |
| --- | --- | --- |
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide as set forth in SEQ ID NO: 2 or SEQ ID NO: 5 using well-known techniques. For identifying suitable areas of the molecule that may be changed without destroying biological activity, one skilled in the art may target areas not believed to be important for activity. For example, when similar polypeptides with similar activities from the same species or from other species are known, one skilled in the art may compare the amino acid sequence of a Secs-1 polypeptide to such similar polypeptides. With such a comparison, one can identify residues and portions of the molecules that are conserved among similar polypeptides. It will be appreciated that changes in areas of the Secs-1 molecule that are not conserved relative to such similar polypeptides would be less likely to adversely affect the biological activity and/or structure of a Secs-1 polypeptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a Secs-1 polypeptide that correspond to amino acid residues that are important for activity or structure in similar polypeptides. One skilled in the art may opt for chemically similar amino acid substitutions for such predicted important amino acid residues of Secs-1 polypeptides.

One skilled in the art can also analyze the three-dimensional structure and amino acid sequence in relation to that structure in similar polypeptides. In view of such information, one skilled in the art may predict the alignment of amino acid residues of Secs-1 polypeptide with respect to its three dimensional structure.

One skilled in the art may choose not to make radical changes to amino acid residues predicted to be on the surface of the protein, since such residues may be involved in important interactions with other molecules. Moreover, one skilled in the art may generate test variants containing a single amino acid substitution at each amino acid residue. The variants could be screened using activity assays known to those with skill in the art. Such variants could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult, 1996, *Curr. Opin. Biotechnol.* 7:422-27; Chou et al., 1974, *Biochemistry* 13:222-45; Chou et al., 1974, *Biochemistry* 113:211-22; Chou et al., 1978, *Adv. Enzymol. Relat. Areas Mol. Biol.* 47:45-48; Chou et al., 1978, *Ann. Rev. Biochem.* 47:251-276; and Chou et al., 1979, *Biophys. J.* 26:367-84. Moreover, computer programs are currently available to assist with predicting secondary structure. One method of predicting secondary structure is based upon homology modeling. For example, two polypeptides or proteins which have a sequence identity of greater than 30%, or similarity greater than 40%, often have similar structural topologies. The recent growth of the protein structural database (PDB) has provided enhanced predictability of secondary structure, including the potential number of folds within the structure of a polypeptide or protein. See Holm et al., 1999, *Nucleic Acids Res.* 27:244-47. It has been suggested that there are a limited number of folds in a given polypeptide or protein and that once a critical number of structures have been resolved, structural prediction will become dramatically more accurate (Brenner et al., 1997, *Curr. Opin. Struct. Biol.* 7:369-76).

Additional methods of predicting secondary structure include "threading" (Jones, 1997, *Curr. Opin. Struct. Biol.* 7:377-87; Sippl et al., 1996, *Structure* 4:15-19), "profile analysis" (Bowie et al., 1991, *Science,* 253:164-70; Gribskov et al., 1990, *Methods Enzymol.* 183:146-59; Gribskov et al., 1987, *Proc. Nat. Acad. Sci. U.S.A.* 84:4355-58), and "evolutionary linkage" (See Holm et al., supra, and Brenner et al., supra).

Preferred Secs-1 polypeptide variants include glycosylation variants wherein the number and/or type of glycosylation sites have been altered compared to the amino acid sequence set forth in SEQ ID NO: 2 or SEQ ID NO: 5. In one embodiment, Secs-1 polypeptide variants comprise a greater or a lesser number of N-linked glycosylation sites than the amino acid sequence set forth in SEQ ID NO: 2 or SEQ ID NO: 5. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred Secs-1 variants include cysteine variants, wherein one or more cysteine residues are deleted or substituted with another amino acid (e.g., serine) as compared to the amino acid sequence set forth in SEQ ID NO: 2 or SEQ ID NO: 5. Cysteine variants are useful when Secs-1 polypeptides must be refolded into a biologically active conformation such as after the isolation of insoluble inclusion bodies. Cysteine variants generally have fewer cysteine residues than the native protein, and typically have an even number to minimize interactions resulting from unpaired cysteines.

In other embodiments, related nucleic acid molecules comprise or consist of a nucleotide sequence encoding a polypeptide as set forth in SEQ ID NO: 2 or SEQ ID NO: 5 with at least one amino acid insertion and wherein the polypeptide has an activity of the polypeptide as set forth in SEQ ID NO: 2 or SEQ ID NO: 5, or a nucleotide sequence encoding a polypeptide as set forth in either SEQ ID NO: 2 or SEQ ID NO: 5 with at least one amino acid deletion and wherein the polypeptide has an activity of the polypeptide as set forth in SEQ ID NO: 2 or SEQ ID NO: 5. Related nucleic acid molecules also comprise or consist of a nucleotide sequence encoding a polypeptide as set forth in either SEQ ID NO: 2 or SEQ ID NO: 5 wherein the polypeptide has a C- and/or N-terminal truncation and further wherein the polypeptide has an activity of the polypeptide as set forth in SEQ ID NO: 2 or SEQ ID NO: 5. Related nucleic acid molecules also comprise or consist of a nucleotide sequence encoding a polypeptide as set forth in either SEQ ID NO: 2 or SEQ ID NO: 5 with at least one modification selected from the group consisting of amino acid substitutions, amino acid insertions, amino acid deletions, C-terminal truncations, and N-terminal truncations and wherein the polypeptide has an activity of the polypeptide as set forth in SEQ ID NO:2 or SEQ D NO: 5.

In addition, the polypeptide comprising the amino acid sequence of SEQ ID NO: 2 or SEQ ID NO: 5 or a Secs-1 polypeptide variant may be fused to a homologous polypeptide to form a homodimer or to a heterologous polypeptide to form a heterodimer. Heterologous peptides and polypeptides include, but are not limited to: an epitope to allow for the detection and/or isolation of a Secs-1 fusion polypeptide; a transmembrane receptor protein or a portion thereof, such as an extracellular domain or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region; and a polypeptide which has a therapeutic activity different from the polypeptide comprising the amino acid sequence as set forth in SEQ ID NO: 2 or SEQ ID NO: 5 or a Secs-1 polypeptide variant.

Fusions can be made either at the amino terminus or at the carboxy terminus of the polypeptide comprising the amino acid sequence set forth in SEQ ID NO: 2 or SEQ ID NO: 5 or a Secs-1 polypeptide variant. Fusions may be direct with no linker or adapter molecule or may be through a linker or adapter molecule. A linker or adapter molecule may be one or more amino acid residues, typically from about 20 to about 50 amino acid residues. A linker or adapter molecule may also be designed with a cleavage site for a DNA restriction endonuclease or for a protease to allow for the separation of the fused moieties. It will be appreciated that once constructed, the fusion polypeptides can be derivatized according to the methods described herein.

In a further embodiment of the invention, the polypeptide comprising the amino acid sequence of SEQ ID NO: 2 or SEQ ID NO: 5 or a Secs-1 polypeptide variant is fused to one or more domains of an Fc region of human IgG. Antibodies comprise two functionally independent parts, a variable domain known as "Fab," that binds antigen, and a constant domain known as "Fc," that is involved in effector functions such as complement activation and attack by phagocytic cells. An Fc has a long serum half-life, whereas an Fab is short-lived. Capon et al, 1989, *Nature* 337:525-31. When constructed together with a therapeutic protein, an Fc domain can provide longer half-life or incorporate such functions as Fc receptor binding, protein A binding, complement fixation, and perhaps even placental transfer. Id. Table II summarizes the use of certain Fc fusions known in the art.

TABLE II

Fc Fusion with Therapeutic Proteins

| Form of Fc | Fusion partner | Therapeutic implications | Reference |
|---|---|---|---|
| IgG1 | N-terminus of CD30-L | Hodgkin's disease; anaplastic lymphoma; T-cell leukemia | U.S. Pat. No. 5,480,981 |
| Murine Fcγ2a | IL-10 | anti-inflammatory; transplant rejection | Zheng et al., 1995, J. Immunol. 154: 5590-600 |
| IgG1 | TNF receptor | septic shock | Fisher et al., 1996, N. Engl. J. Med. 334: 1697-1702; Van Zee et al., 1996, J. Immunol. 156: 2221-30 |
| IgG, IgA, IgM, or IgE (excluding the first domain) | TNF receptor | inflammation, autoimmune disorders | U.S. Pat. No. 5,808,029 |
| IgG1 | CD4 receptor | AIDS | Capon et al., 1989, Nature 337: 525-31 |
| IgG1, IgG3 | N-terminus of IL-2 | anti-cancer, antiviral | Harvill et al., 1995, Immunotech. 1: 95-105 |
| IgG1 | C-terminus of OPG | osteoarthritis; bone density | WO 97/23614 |
| IgG1 | N-terminus of leptin | anti-obesity | PCT/US 97/23183, filed Dec. 11, 1997 |
| Human Ig Cγ1 | CTLA-4 | autoimmune disorders | Linsley, 1991, J. Exp. Med., 174: 561-69 |

In one example, a human IgG hinge, CH2, and CH3 region may be fused at either the N-terminus or C-terminus of the Secs-1 polypeptides using methods known to the skilled artisan. The resulting Secs-1 fusion polypeptide may be purified by use of a Protein A affinity column. Peptides and proteins fused to an Fc region have been found to exhibit a substantially greater half-life in vivo than the unfused counterpart. Also, a fusion to an Fc region allows for dimerization/multimerization of the fusion polypeptide. The Fc region may be a naturally occurring Fc region, or may be altered to improve certain qualities, such as therapeutic qualities, circulation time, or reduced aggregation.

Identity and similarity of related nucleic acid molecules and polypeptides can be readily calculated by known methods. Such methods include, but are not limited to those described in *Computational Molecular Biology* (A. M. Lesk, ed., Oxford University Press 1988); *Biocomputing: Informatics and Genome Projects* (D. W. Smith, ed., Academic Press 1993); *Computer Analysis of Sequence Data* (Part 1, A. M. Griffin and H. G. Griffin, eds., Humana Press 1994); G. von Heinle, *Sequence Analysis in Molecular Biology* (Academic Press 1987); *Sequence Analysis Primer* (M. Gribskov and J. Devereux, eds., M. Stockton Press 1991); and Carillo et al., 1988, *SIAM J. Applied Math.*, 48:1073.

Preferred methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG program package, including GAP (Devereux et al., 1984, *Nucleic Acids Res.* 12:387; Genetics Computer Group, University of Wisconsin, Madison, Wis.), BLASTP, BLASTN, and FASTA (Altschul et al., 1990, *J. Mol. Biol.* 215:403-10). The BLASTX program is publicly available from the National Center for Biotechnology Information (NCBI) and other sources (Altschul et al., *BLAST Manual* (NCB National Library Medicine NIH, Bethesda, Md.); Altschul et al., 1990, supra). The well-known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full-length sequences. Accordingly, in a preferred embodiment, the selected alignment method (GAP program) will result in an alignment that spans at least 50 contiguous amino acids of the claimed polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span," as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 0.1× the gap opening penalty), as well as a comparison matrix such as PAM 250 or BLOSUM 62 are used in conjunction with the algorithm. A standard comparison matrix is also used by the algorithm (see Dayhoff et al., 5 *Atlas of Protein Sequence and Structure* (Supp. 3 1978)(PAM250 comparison matrix); Henikoff et al., 1992, *Proc. Natl. Acad. Sci USA* 89:10915-19 (BLOSUM 62 comparison matrix)).

Preferred parameters for polypeptide sequence comparison include the following:
Algorithm: Needleman and Wunsch, 1970, *J. Mol. Biol.* 48:443-53;
Comparison matrix: BLOSUM 62 (Henikoff et al., supra);
Gap Penalty: 12
Gap Length Penalty: 4
Threshold of Similarity: 0

The GAP program is useful with the above parameters. The aforementioned parameters are the default parameters for polypeptide comparisons (along with no penalty for end gaps) using the GAP algorithm.

Preferred parameters for nucleic acid molecule sequence comparison include the following:
Algorithm: Needleman and Wunsch, supra;
Comparison matrix: matches=+10, mismatch=0
Gap Penalty: 50
Gap Length Penalty: 3

The GAP program is also useful with the above parameters. The aforementioned parameters are the default parameters for nucleic acid molecule comparisons.

Other exemplary algorithms, gap opening penalties, gap extension penalties, comparison matrices, and thresholds of similarity may be used, including those set forth in the Program Manual, Wisconsin Package, Version 9, September, 1997. The particular choices to be made will be apparent to those of skill in the art and will depend on the specific comparison to be made, such as DNA-to-DNA, protein-to-protein, protein-to-DNA; and additionally, whether the comparison is between given pairs of sequences (in which case GAP or BestFit are generally preferred) or between one sequence and a large database of sequences (in which case FASTA or BLASTA are preferred).

Nucleic Acid Molecules

The nucleic acid molecules encoding a polypeptide comprising the amino acid sequence of a Secs-1 polypeptide can readily be obtained in a variety of ways including, without limitation, chemical synthesis, cDNA or genomic library screening, expression library screening, and/or PCR amplification of cDNA.

Recombinant DNA methods used herein are generally those set forth in Sambrook et al., *Molecular Cloning: A Laboratory Manual* (Cold Spring Harbor Laboratory Press, 1989) and/or *Current Protocols in Molecular Biology* (Ausubel. et al., eds., Green Publishers Inc. and Wiley and Sons 1994). The invention provides for nucleic acid molecules as described herein and methods for obtaining such molecules.

Where a gene encoding the amino acid sequence of a Secs-1 polypeptide has been identified from one species, all or a portion of that gene may be used as a probe to identify orthologs or related genes from the same species. The probes or primers may be used to screen cDNA libraries from various tissue sources believed to express the Secs-1 polypeptide. In addition, part or all of a nucleic acid molecule having the sequence as set forth in SEQ ID NO: 1 or SEQ ID NO: 4 may be used to screen a genomic library to identify and isolate a gene encoding the amino acid sequence of a Secs-1 polypeptide. Typically, conditions of moderate or high stringency will be employed for screening to minimize the number of false positives obtained from the screening.

Nucleic acid molecules encoding the amino acid sequence of Secs-1 polypeptides may also be identified by expression cloning which employs the detection of positive clones based upon a property of the expressed protein. Typically, nucleic acid libraries are screened by the binding an antibody or other binding partner (e.g., receptor or ligand) to cloned proteins that are expressed and displayed on a host cell surface. The antibody or binding partner is modified with a detectable label to identify those cells expressing the desired clone.

Recombinant expression techniques conducted in accordance with the descriptions set forth below may be followed to produce these polynucleotides and to express the encoded polypeptides. For example, by inserting a nucleic acid sequence that encodes the amino acid sequence of a Secs-1 polypeptide into an appropriate vector, one skilled in the art can readily produce large quantities of the desired nucleotide sequence. The sequences can then be used to generate detection probes or amplification primers. Alternatively, a polynucleotide encoding the amino acid sequence of a Secs-1 polypeptide can be inserted into an expression vector. By introducing the expression vector into an appropriate host, the encoded Secs-1 polypeptide may be produced in large amounts.

Another method for obtaining. a suitable nucleic acid sequence is the polymerase chain reaction (PCR). In this method, cDNA is prepared from poly(A)+RNA or total RNA using the enzyme reverse transcriptase. Two primers, typically complementary to two separate regions of cDNA encoding the amino acid sequence of a Secs-1 polypeptide, are then added to the cDNA along with a polymerase such as Taq polymerase, and the polymerase amplifies the cDNA region between the two primers.

Another means of preparing a nucleic acid molecule encoding the amino acid sequence of a Secs-1 polypeptide is chemical synthesis using methods well known to the skilled artisan such as those described by Engels et al., 1989, *Angew. Chem. Intl. Ed.* 28:716-34. These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the amino acid sequence of a Secs-1 polypeptide will be several hundred nucleotides in length. Nucleic acids larger than about 100 nucleotides can be synthesized as several fragments using these methods. The fragments can then be ligated together to form the full-length nucleotide sequence of a Secs-1 gene. Usually, the DNA fragment encoding the amino terminus of the polypeptide will have an ATG, which encodes a methionine residue. This methionine may or may not be present on the mature form of the Secs-1 polypeptide, depending on whether the polypeptide produced in the host cell is designed to be secreted from that cell. Other methods known to the skilled artisan may be used as well.

In certain embodiments, nucleic acid variants contain codons which have been altered for optimal expression of a Secs-1 polypeptide in a given host cell. Particular codon alterations will depend upon the Secs-1 polypeptide and host cell selected for expression. Such "codon optimization" can be carried out by a variety of methods, for example, by selecting codons which are preferred for use in highly expressed genes in a given host cell. Computer algorithms which incorporate codon frequency tables such as "Eco_high.Cod" for codon preference of highly expressed bacterial genes may be used and are provided by the University of Wisconsin Package Version 9.0 (Genetics Computer Group, Madison, Wis.). Other useful codon frequency tables include "Celegans_high.cod," "Celegans_low.cod," "Drosophila_high.cod," "Human_high.cod," "Maize_high.cod," and "Yeast_high.cod."

In some cases, it may be desirable to prepare nucleic acid molecules encoding Secs-1 polypeptide variants. Nucleic acid molecules encoding variants may be produced using site directed mutagenesis, PCR amplification, or other appropriate methods, where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well.

In other embodiments, nucleic acid molecules encode Secs-1 polypeptide variants with conservative amino acid substitutions, Secs-1 polypeptide variants with amino acid insertions, or Secs-1 polypeptide variants with amino acid deletions, as described herein. Such Secs-1 polypeptide variants may comprise, for example, an addition and/or a deletion of one or more N-linked or O-linked glycosylation sites or an addition and/or a deletion of one or more cysteine residues. In still other embodiments, nucleic acid molecules encode Secs-1 polypeptide variants having C- and/or N-terminal truncation, as described herein. In still further embodiments, nucleic acid molecules may encode Secs-1 polypeptide variants with at least one modification selected from the group consisting of amino acid substitutions, amino acid insertions, amino acid deletions, C-terminal truncations, and N-terminal truncations, as described herein.

Vectors and Host Cells

A nucleic acid molecule encoding the amino acid sequence of a Secs-1 polypeptide is inserted into an appropriate expression vector using standard ligation techniques. The vector is typically selected to be functional in the particular host cell employed (i.e., the vector is compatible with the host cell machinery such that amplification of the gene and/or expression of the gene can occur). A nucleic acid molecule encoding the amino acid sequence of a Secs-1 polypeptide may be amplified/expressed in prokaryotic, yeast, insect (baculovirus systems) and/or eukaryotic host cells. Selection of the host cell will depend in part on whether a Secs-1 polypeptide is to be post-translationally modified (e.g., glycosylated and/or phosphorylated). If so, yeast, insect, or mammalian host cells are preferable. For a review of expression vectors, see *Meth. Enz.*, vol. 185 (D. V. Goeddel, ed., Academic Press 1990).

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the Secs-1 polypeptide coding sequence; the oligonucleotide sequence encodes polyHis (such as hexaHis), or another "tag" such as FLAG, HA (hemaglutinin influenza virus), or myc for which commercially available antibodies exist. This tag is typically fused to the polypeptide upon expression of the polypeptide, and can serve as a means for affinity purification of the Secs-1 polypeptide from the host cell. Afinity purification can be accomplished, for example, by column chromatography using antibodies against the tag as an affinity matrix. Optionally, the tag can subsequently be removed from the purified Secs-1 polypeptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), or synthetic, or the flanking sequences may be native sequences which normally function to regulate Secs-1 polypeptide expression. As such, the source of a flanking sequence may be any prokaryotic or eukaryotic organism, any vertebrate or invertebrate organism, or any plant, provided that the flanking sequence is functional in, and can be activated by, the host cell machinery.

The flanking sequences useful in the vectors of this invention may be obtained by any of several methods well known in the art. Typically, flanking sequences useful herein—other than the Secs-1 gene flanking sequences—will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with a suitable oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, column chromatography (QIAGEN Inc., Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. Amplification of the vector to a certain copy number can, in some cases, be important for the optimal expression of a Secs-1 polypeptide. If the vector of choice does not contain an origin of replication site, one may be chemically synthesized based on a known sequence, and ligated into the vector. For example, the origin of replication from the plasmid pBR322 (New England Biolabs, Inc., Beverly, Mass.) is suitable for most gram-negative bacteria and various origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it contains the early promoter).

A transcription termination sequence is typically located 3' of the end of a polypeptide coding region and serves to terminate transcription. Usually, a transcription termination sequence in prokaryotic cells is a G–C rich fragment followed by a poly-T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex media. Preferred selectable markers are the kanamycin resistance gene, the ampicillin resistance gene, and the tetracycline resistance gene. A neomycin resistance gene may also be used for selection in prokaryotic and eukaryotic host cells.

Other selection genes may be used to amplify the gene that will be expressed. Amplification is the process wherein genes that are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure wherein only the transformants are uniquely adapted to survive by virtue of the selection gene present in the vector. Selection pressure is imposed by culturing the transformed cells under conditions in which the concentration of selection agent in the medium is successively changed, thereby leading to the amplification of both the selection gene and the DNA that encodes a Secs-1 polypeptide. As a result, increased quantities of Secs-1 polypeptide are synthesized from the amplified DNA.

A ribosome binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of a Secs-1 polypeptide to be expressed. The Shine-Dalgarno sequence is varied but is typically a polypurine (i.e., having a high A-G content). Many Shine-Dalgarno sequences have been identified, each of which can be readily synthesized using methods set forth herein and used in a prokaryotic vector.

A leader, or signal, sequence may be used to direct a Secs-1 polypeptide out of the host cell. Typically, a nucleotide sequence encoding the signal sequence is positioned in the coding region of a Secs-1 nucleic acid molecule, or directly at the 5' end of a Secs-1 polypeptide coding region. Many signal sequences have been identified, and any of those that are functional in the selected host cell may be used in conjunction with a Secs-1 nucleic acid molecule. Therefore, a signal sequence may be homologous (naturally occurring) or heterologous to the Secs-1 nucleic acid molecule. Additionally, a signal sequence may be chemically synthesized using methods described herein. In most cases, the secretion of a Secs-1 polypeptide from the host cell via the presence of a signal peptide will result in the removal of the signal peptide from the secreted Secs-1 polypeptide. The signal sequence may be a component of the vector, or it may be a part of a Secs-1 nucleic acid molecule that is inserted into the vector.

Included within the scope of this invention is the use of either a nucleotide sequence encoding a native Secs-1 polypeptide signal sequence joined to a Secs-1 polypeptide coding region or a nucleotide sequence encoding a heterologous signal sequence joined to a Secs-1 polypeptide coding region. The heterologous signal sequence selected should be one that is recognized and processed, i.e., cleaved by a signal peptidase, by the host cell. For prokaryotic host cells that do not recognize and process the native Secs-1 polypeptide signal sequence, the signal sequence is substituted by a prokaryotic signal sequence selected, for example, from the group of the alkaline phosphatase, penicillinase, or heat-stable enterotoxin II leaders. For yeast secretion, the native Secs-1 polypeptide signal sequence may be substituted by the yeast invertase, alpha factor, or acid phosphatase leaders. In mammalian cell expression the native signal sequence is satisfactory, although other mammalian signal sequences may be suitable.

In some cases, such as where glycosylation is desired in a eukaryotic host cell expression system, one may manipulate the various presequences to improve glycosylation or yield. For example, one may alter the peptidase cleavage site of a particular signal peptide, or add pro-sequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the N-terminus. Alternatively, use of some enzyme cleavage sites may result in a slightly truncated form of the desired Secs-1 polypeptide, if the enzyme cuts at such area within the mature polypeptide.

In many cases, transcription of a nucleic acid molecule is increased by the presence of one or more introns in the vector; this is particularly true where a polypeptide is produced in eukaryotic host cells, especially mammalian host cells. The introns used may be naturally occurring within the Secs-1 gene especially where the gene used is a full-length genomic sequence or a fragment thereof. Where the intron is not naturally occurring within the gene (as for most cDNAs), the intron may be obtained from another source. The position of the intron with respect to flanking sequences and the Secs-1 gene is generally important, as the intron must be transcribed to be effective. Thus, when a Secs-1 cDNA molecule is being transcribed, the preferred position for the intron is 3' to the transcription start site and 5' to the poly-A transcription termination sequence. Preferably, the intron or introns will be located on one side or the other (i.e., 5' or 3') of the cDNA such that it does not interrupt the coding sequence. Any intron from any source, including viral, prokaryotic and eukaryotic (plant or animal) organisms, may be used to practice this invention, provided that it is compatible with the host cell into which it is inserted. Also included herein are synthetic introns. Optionally, more than one intron may be used in the vector.

The expression and cloning vectors of the present invention will typically contain a promoter that is recognized by the host organism and operably linked to the molecule encoding the Secs-1 polypeptide. Promoters are untranscribed sequences located upstream (i.e., 5') to the start codon of a structural gene (generally within about 100 to 1000 bp) that control the transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression. A large number of promoters, recognized by a variety of potential host cells, are well known. A suitable promoter is operably linked to the DNA encoding Secs-1 polypeptide by removing the promoter from the source DNA by restriction enzyme digestion and inserting the desired promoter sequence into the vector. The native Secs-1 promoter sequence may be used to direct amplification and/or expression of a Secs-1 nucleic acid molecule. A heterologous promoter is preferred, however, if it permits greater transcription and higher yields of the expressed protein as compared to the native promoter, and if it is compatible with the host cell system that has been selected for use.

Promoters suitable for use with prokaryotic hosts include the beta-lactamase and lactose promoter systems; alkaline phosphatase; a tryptophan (trp) promoter system; and hybrid promoters such as the tac promoter. Other known bacterial promoters are also suitable. Their sequences have been published, thereby enabling one skilled in the art to ligate them to the desired DNA sequence, using linkers or adapters as needed to supply any useful restriction sites.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest in controlling Secs-1 gene expression include, but are not limited to: the SV40 early promoter region (Bemoist and Chambon, 1981, *Nature* 290:304-10); the CMV promoter; the promoter contained in the 3' long terminal repeat of Rous sarcoma virus (Yamamoto, et al., 1980, *Cell* 22:787-97); the herpes thymidine kinase promoter (Wagner et al., 1981, *Proc. Natl. Acad. Sci. U.S.A.* 78:1444-45); the regulatory sequences of the metallothionine gene (Brinster et al., 1982, *Nature* 296:39-42); prokaryotic expression vectors such as the beta-lactamase promoter (Villa-Kamaroff et al., 1978, *Proc. Natl. Acad. Sci. U.S.A.*, 75:3727-31); or the tac promoter (DeBoer et al., 1983, *Proc. Natl. Acad. Sci. U.S.A.*, 80:21-25). Also of interest are the following animal transcriptional control regions, which exhibit tissue specificity and have been utilized in transgenic animals: the elastase I gene control region which is active in pancreatic acinar cells (Swift et al., 1984, *Cell* 38:639-46; Ornitz et al., 1986, *Cold Spring Harbor Symp. Quant. Biol.* 50:399-409 (1986); MacDonald, 1987, *Hepatology* 7:425-515); the insulin gene control region which is active in pancreatic beta cells (Hanahan, 1985, *Nature* 315:115-22); the immunoglobulin gene control region which is active in lymphoid cells (Grosschedl et al., 1984, *Cell* 38:647-58; Adames et al., 1985, *Nature* 318:533-38; Alexander et al., 1987, *Mol. Cell. Biol.*, 7:1436-44); the mouse mammary tumor virus control region which is active in testicular, breast, lymphoid and mast cells (Leder et al., 1986, *Cell* 45:485-95); the albumin gene control region which is active in liver (Pinkert et al., 1987, *Genes and Devel.* 1:268-76); the alpha-feto-protein gene control region which is active in liver (Krumlauf et al., 1985, *Mol. Cell. Biol.*, 5:1639-48; Hammer et al., 1987, *Science* 235:53-58); the alpha 1-antitrypsin gene control region which is active in the liver (Kelsey et al., 1987, *Genes and Devel.* 1:161-71); the beta-globin gene control region which is active in myeloid cells (Mogram et al., 1985, *Nature* 315:338-40; Kollias et al., 1986, *Cell* 46:89-94); the myelin basic protein gene control region which is active in oligodendrocyte cells in the brain (Readhead et al., 1987, *Cell* 48:703-12); the myosin light chain-2 gene control region which is active in skeletal muscle (Sani, 1985, *Nature* 314:283-86); and the gonadotropic releasing hormone gene control region which is active in the hypothalamus (Mason et al., 1986, *Science* 234:1372-78).

An enhancer sequence may be inserted into the vector to increase the transcription of a DNA encoding a Secs-1 polypeptide of the present invention by higher eukaryotes. Enhancers are cis-acting elements of DNA, usually about 10-300 bp in length, that act on the promoter to increase transcription. Enhancers are relatively orientation and position independent. They have been found 5' and 3' to the transcription unit. Several enhancer sequences available from mammalian genes are known (e.g., globin, elastase, albumin, alpha-feto-protein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to a Secs-1 nucleic acid molecule, it is typically located at a site 5' from the promoter.

Expression vectors of the invention may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

Preferred vectors for practicing this invention are those which are compatible with bacterial, insect, and mammalian host cells. Such vectors include, inter alia, pCRII, pCR3, and pcDNA3.1 (Invitrogen Corp., San Diego, Calif.), pBSII (Stratagene Corp., La Jolla, Calif.), pET15 (Novagen, Inc., Madison, Wis.), pGEX (Pharmacia Biotech, Piscataway, N.J.), pEGFP-N2 (Clontech Laboratories, Inc., Palo Alto, Calif.), pETL (BlueBach, Invitrogen Corp.), pDSR-alpha (PCT Pub. No. WO 90/14363) and pFastBacDual (GIBCO-BRL, Grand Island, N.Y.).

Additional suitable vectors include, but are not limited to, cosmids, plasmids, or modified viruses, but it will be appreciated that the vector system must be compatible with the selected host cell. Such vectors include, but are not limited to plasmids such as Bluescript® plasmid derivatives (a high copy number ColE1-based phagemid, Stratagene Corp., La Jolla, Calif.), PCR cloning plasmids designed for cloning Taq-amplified PCR products (e.g., TOPO TA Cloning® Kit, PCR2.1 plasmid derivatives, Invitrogen Corp., Carlsbad, Calif.), and mammalian, yeast or virus vectors such as a baculovirus expression system (pBacPAK plasmid derivatives, Clontech Laboratories, Inc., Palo Alto, Calif.).

After the vector has been constructed and a nucleic acid molecule encoding a Secs-1 polypeptide has been inserted into the proper site of the vector, the completed vector may be inserted into a suitable host cell for amplification and/or polypeptide expression. The transformation of an expression vector for a Secs-1 polypeptide into a selected host cell may be accomplished by well known methods including methods such as transfection, infection, calcium chloride, electroporation, microinjection, lipofection, DEAE-dextran method, or other known techniques. The method selected will in part be a function of the type of host cell to be used. These methods and other suitable methods are well known to the skilled artisan, and are set forth, for example, in Sambrook et al., supra.

Host cells may be prokaryotic host cells (such as E. coli) or eukaryotic host cells (such as a yeast, insect, or vertebrate cell). The host cell, when cultured under appropriate conditions, synthesizes a Secs-1 polypeptide which can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

A number of suitable host cells are known in the art and many are available from the American Type Culture Collection (ATCC), Manassas, Va. Examples include, but are not limited to, mammalian cells, such as Chinese hamster ovary cells (CHO), CHO DHFR(-) cells (Urlaub et al., 1980, Proc. Natl. Acad. Sci. U.S.A. 97:4216-20), human embryonic kidney (HEK) 293 or 293T cells, or 3T3 cells. The selection of suitable mammalian host cells and methods for transformation, culture, amplification, screening, product production, and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, Hela, mouse L-929 cells, 3T3 lines derived from Swiss, Balb-c or NIH mice, BHK or HaK hamster cell lines. Each of these cell lines is known by and available to those skilled in the art of protein expression.

Similarly useful as host cells suitable for the present invention are bacterial cells. For example, the various strains of E. coli (e.g., HB101, DH5α, DH10, and MC1061) are well-known as host cells in the field of biotechnology. Various strains of B. subtilis, Pseudomonas spp., other Bacillus spp., Streptomyces spp., and the like may also be employed in this method.

Many strains of yeast cells known to those skilled in the art are also available as host cells for the expression of the polypeptides of the present invention. Preferred yeast cells include, for example, Saccharomyces cerivisae and Pichia pastoris.

Additionally, where desired, insect cell systems may be utilized in the methods of the present invention. Such systems are described, for example, in Kitts et al., 1993, Biotechniques, 14:810-17; Lucklow, 1993, Curr. Opin. Biotechnol. 4:564-72; and Lucklow et al., 1993, J. Virol., 67:4566-79. Preferred insect cells are Sf-9 and Hi5 (Invitrogen Corp.).

One may also use transgenic animals to express glycosylated Secs-1 polypeptides. For example, one may use a transgenic milk-producing animal (a cow or goat, for example) and obtain the present glycosylated polypeptide in the animal milk. One may also use plants to produce Secs-1 polypeptides, however, in general, the glycosylation occurring in plants is different from that produced in mammalian cells, and may result in a glycosylated product which is not suitable for human therapeutic use.

Polypeptide Production

Host cells comprising a Secs-1 polypeptide expression vector may be cultured using standard media well known to the skilled artisan. The media will usually contain all nutrients necessary for the growth and survival of the cells. Suitable media for culturing E. coli cells include, for example, Luria Broth (LB) and/or Terrific Broth (TB). Suitable media for culturing eukaryotic cells include Roswell Park Memorial Institute medium 1640 (RPMI 1640), Minimal Essential Medium (MEM) and/or Dulbecco's Modified Eagle Medium (DMEM), all of which may be supplemented with serum and/or growth factors as necessary for the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of transfected or transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin. Other compounds for selective growth include ampicillin, tetracycline, and neomycin.

The amount of a Secs-1 polypeptide produced by a host cell can be evaluated using standard methods known in the art. Such methods include, without limitation, Western blot analysis, SDS-polyacrylamide gel electrophoresis, non-denaturing gel electrophoresis, High Performance Liquid Chromatography (HPLC) separation, immunoprecipitation, and/or activity assays such as DNA binding gel shift assays.

If a Secs-1 polypeptide has been designed to be secreted from the host cells, the majority of polypeptide may be found in the cell culture medium. If however, the Secs-1 polypeptide is not secreted from the host cells, it will be present in the cytoplasm and/or the nucleus (for eukaryotic host cells) or in the cytosol (for gram-negative bacteria host cells).

For a Secs-1 polypeptide situated in the host cell cytoplasm and/or nucleus (for eukaryotic host cells) or in the cytosol (for bacterial host cells), the intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation.

If a Secs-1 polypeptide has formed inclusion bodies in the cytosol, the inclusion bodies can often bind to the inner and/or outer cellular membranes and thus will be found primarily in the pellet material after centrifugation. The pellet material can then be treated at pH extremes or with a chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The solubilized Secs-1 polypeptide can then be analyzed using gel electrophoresis, immunoprecipitation, or the like. If it is desired to isolate the Secs-1 polypeptide, isolation may be accomplished using standard methods such as those described herein and in Marston et al., 1990, *Meth. Enz.*, 182:264-75.

In some cases, a Secs-1 polypeptide may not be biologically active upon isolation. Various methods for "refolding" or converting the polypeptide to its tertiary structure and generating disulfide linkages can be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing agent or the reducing agent plus its oxidized form in a specific ratio to generate a particular redox potential allowing for disulfide shuffling to occur in the formation of the protein's cysteine bridges. Some of the commonly used redox couples include cysteine/cystamine, glutathione (GSH)/dithiobis GSH, cupric chloride, dithiothreitol(DTT)/dithiane DTT, and 2-2-mercaptoethanol(bME)/dithio-b(ME). In many instances, a cosolvent may be used or may be needed to increase the efficiency of the refolding, and the more common reagents used for this purpose include glycerol, polyethylene glycol of various molecular weights, arginine and the like.

If inclusion bodies are not formed to a significant degree upon expression of a Secs-1 polypeptide, then the polypeptide will be found primarily in the supernatant after centrifugation of the cell homogenate. The polypeptide may be further isolated from the supernatant using methods such as those described herein.

The purification of a Secs-1 polypeptide from solution can be accomplished using a variety of techniques. If the polypeptide has been synthesized such that it contains a tag such as Hexahistidine (Secs-1 polypeptide/hexaHis) or other small peptide such as FLAG (Eastman Kodak Co., New Haven, Conn.) or myc (Invitrogen Corp., Carlsbad, Calif.) at either its carboxyl- or amino-terminus, it may be purified in a one-step process by passing the solution through an affinity column where the column matrix has a high affinity for the tag.

For example, polyhistidine binds with great affinity and specificity to nickel. Thus, an affinity column of nickel (such as the nickel columns of QIAGEN Inc.) can be used for purification of Secs-1 polypeptide/polyHis. See, e.g., *Current Protocols in Molecular Biology* § 10.11.8 (Ausubel et al., eds., Green Publishers Inc. and Wiley and Sons 1993).

Additionally, the SECS-1 like polypeptide may be purified through the use of a monoclonal antibody that is capable of specifically recognizing and binding to the SECS-1. like polypeptide.

Suitable procedures for purification thus include, without limitation, affinity chromatography, immunoaffinity chromatography, ion exchange. chromatography, molecular sieve chromatography, HPLC, electrophoresis (including native gel electrophoresis) followed by gel elution, and preparative isoelectric focusing ("Isoprime" machine/technique, Hoefer Scientific, San Francisco, Calif.). In some cases, two or more purification techniques may be combined to achieve increased purity.

Secs-1 polypeptides may also be prepared by chemical synthesis methods (such as solid phase peptide synthesis) using techniques known in the art such as those set forth by Merrifield et al., 1963, *J. Am. Chem. Soc.* 85:2149; Houghten et al., 1985, *Proc Natl Acad. Sci. USA* 82:5132; and Stewart and Young, *Solid Phase Peptide Synthesis* (Pierce Chemical Co. 1984). Such polypeptides may be synthesized with or without a methionine on the amino terminus. Chemically synthesized Secs-1 polypeptides may be oxidized using methods set forth in these references to form disulfide bridges. Chemically synthesized Secs-1 polypeptides are expected to have comparable biological activity to the corresponding Secs-1 polypeptides produced recombinantly or purified from natural sources, and thus may be used interchangeably with a recombinant or natural Secs-1 polypeptide.

Another means of obtaining Secs-1 polypeptide is via purification from biological samples such as source tissues and/or fluids in which the Secs-1 polypeptide is naturally found. Such purification can be conducted using methods for protein purification as described herein. The presence of the Secs-1 polypeptide during purification may be monitored, for example, using an antibody prepared against recombinantly produced Secs-1 polypeptide or peptide fragments thereof.

A number of additional methods for producing nucleic acids and polypeptides are known in the art, and the methods can be used to produce polypeptides having specificity for Secs-1 polypeptide. See, e.g., Roberts et al., 1997, *Proc. Natl. Acad. Sci. U.S.A.* 94:12297-303, which describes the production of fusion proteins between an mRNA and its encoded peptide. See also, Roberts, 1999, *Curr. Opin. Chem. Biol.* 3:268-73. Additionally, U.S. Pat. No. 5,824,469 describes methods for obtaining oligonucleotides capable of carrying out a specific biological function. The procedure involves generating a heterogeneous pool of oligonucleotides, each having a 5' randomized sequence, a central preselected sequence, and a 3' randomized sequence. The resulting heterogeneous pool is introduced into a population of cells that do not exhibit the desired biological function. Subpopulations of the cells are then screened for those that exhibit a predetermined biological function. From that subpopulation, oligonucleotides capable of carrying out the desired biological function are isolated.

U.S. Pat. Nos. 5,763,192; 5,814,476; 5,723,323; and 5,817,483 describe processes for producing peptides or polypeptides. This is done by producing stochastic genes or fragments thereof, and then introducing these genes into host cells which produce one or more proteins encoded by the stochastic genes. The host cells are then screened to identify those clones producing peptides or polypeptides having the desired activity.

Another method for producing peptides or polypeptides is described in PCT/US98/20094 (WO99/15650) filed by Athersys, Inc. Known as "Random Activation of Gene Expression for Gene Discovery" (RAGE-GD), the process involves the activation of endogenous gene expression or over-expression of a gene by in situ recombination methods. For example, expression of an endogenous gene is activated or increased by integrating a regulatory sequence into the target cell which is capable of activating expression of the gene by non-homologous or illegitimate recombination. The target DNA is first subjected to radiation, and a genetic promoter inserted. The promoter eventually locates a break at the front of a gene, initiating transcription of the gene. This results in expression of the desired peptide or polypeptide.

It will be appreciated that these methods can also be used to create comprehensive IL-17 like protein expression libraries, which can subsequently be used for high throughput phenotypic screening in a variety of assays, such as biochemical assays, cellular assays, and whole organism assays (e.g., plant, mouse, etc.).

Synthesis

It will be appreciated by those skilled in the art that the nucleic acid and polypeptide molecules described herein many be produced by recombinant and other means.

Selective Binding Agents

As used herein, the term "selective binding agent" refers to a molecule that has specificity for one or more Secs-1 polypeptides. Suitable selective binding agents include, but are not limited to, antibodies and derivatives thereof, polypeptides, and small molecules. Suitable selective binding agents may be prepared using methods known in the art. An exemplary Secs-1 polypeptide selective binding agent of the present invention is capable of binding a certain portion of the Secs-1 polypeptide thereby inhibiting the binding of the polypeptide to a Secs-1 polypeptide receptor.

Selective binding agents such as antibodies and antibody fragments that bind Secs-1 polypeptides are within the scope of the present invention. The antibodies may be polyclonal including monospecific polyclonal; monoclonal (MAbs); recombinant; chimeric; humanized, such as CDR-grafted; human; single chain; and/or bispecific; as well as fragments; variants; or derivatives thereof.

Antibody fragments include those portions of the antibody that bind to an epitope on the Secs-1 polypeptide. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions.

Polyclonal antibodies directed toward a Secs-1 polypeptide generally are produced in animals (e.g., rabbits or mice) by means of multiple subcutaneous or intraperitoneal injections of Secs-1 polypeptide and an adjuvant. It may be useful to conjugate a Secs-1 polypeptide to a carrier protein that is immunogenic in the species to be immunized, such as keyhole limpet hemocyanin, serum, albumin, bovine thyroglobulin, or soybean trypsin inhibitor. Also, aggregating agents such as alum are used to enhance the immune response. After immunization, the animals are bled and the serum is assayed for anti-Secs-1 antibody titer.

Monoclonal antibodies directed toward Secs-1 polypeptides are produced using any method that provides for the production of antibody molecules by continuous cell lines in culture. Examples of suitable methods for preparing monoclonal antibodies include the hybridoma methods of Kohler et al., 1975, *Nature* 256:495-97 and the human B-cell hybridoma method (Kozbor, 1984, *J. Immunol.* 133:3001; Brodeur et al., *Monoclonal Antibody Production Techniques and Applications* 51-63 (Marcel Dekker, Inc., 1987). Also provided by the invention are hybridoma cell lines that produce monoclonal antibodies reactive with Secs-1 polypeptides.

Monoclonal antibodies of the invention may be modified for use as therapeutics. One embodiment is a "chimeric" antibody in which a portion of the heavy and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. Also included are fragments of such antibodies, so long as they exhibit the desired biological activity. See U.S. Pat. No. 4,816,567; Morrison et al., 1985, *Proc. Natl. Acad. Sci.* 81:6851-55.

In another embodiment, a monoclonal antibody of the invention is a "humanized" antibody. Methods for humanizing non-human antibodies are well known in the art. See U.S. Pat. Nos. 5,585,089 and 5,693,762. Generally, a humanized antibody has one or more amino acid residues introduced into it from a source that is non-human. Humanization can be performed, for example, using methods described in the art (Jones et al., 1986, *Nature* 321:522-25; Riechmann et al., 1998, *Nature* 332:323-27; Verhoeyen et al., 1988, *Science* 239:1534-36), by substituting at least a portion of a rodent complementarity-determining region (CDR) for the corresponding regions of a human antibody.

Also encompassed by the invention are human antibodies that bind Secs-1 polypeptides. Using transgenic animals (e.g., mice) that are capable of producing a repertoire of human antibodies in the absence of endogenous immunoglobulin production such antibodies are produced by immunization with a Secs-1 polypeptide antigen (i.e., having at least 6 contiguous amino acids), optionally conjugated to a carrier. See, e.g., Jakobovits et al., 1993, *Proc. Natl. Acad. Sci.* 90:2551-55; Jakobovits et al., 1993, *Nature* 362:255-58; Bruggermann et al., 1993, *Year in Immuno.* 7:33. In one method, such transgenic animals are produced by incapacitating the endogenous loci encoding the heavy and light immunoglobulin chains therein, and inserting loci encoding human heavy and light chain proteins into the genome thereof. Partially modified animals, that is those having less than the full complement of modifications, are then crossbred to obtain an animal having all of the desired immune system modifications. When administered an immunogen, these transgenic animals produce antibodies with human (rather than, e.g., murine) amino acid sequences, including variable regions which are immunospecific for these antigens. See PCT App. Nos. PCT/US96/05928 and PCT/US93/06926. Additional methods are described in U.S. Pat. No. 5,545,807, PCT App. Nos. PCT/US91/245 and PCT/GB89/01207, and in EP Pub. Nos. 546073B1 and 546073A1. Human antibodies can also be produced by the expression of recombinant DNA in host cells or by expression in hybridoma cells as described herein.

In an alternative embodiment, human antibodies can also be produced from phage-display libraries (Hoogenboom et al., 1991, *J. Mol. Biol.* 227:381; Marks et al., 1991, *J. Mol. Biol.* 222:581). These processes mimic immune selection through the display of antibody repertoires on the surface of filamentous bacteriophage, and subsequent selection of phage by their binding to an antigen of choice. One such technique is described in PCT App. No. PCT/US98/17364, which describes the isolation of high affinity and functional agonistic antibodies for MPL- and msk- receptors using such an approach.

Chimeric, CDR grafted, and humanized antibodies are typically produced by recombinant methods. Nucleic acids encoding the antibodies are introduced into host cells and expressed using materials and procedures described herein. In a preferred embodiment, the antibodies are produced in mammalian host cells, such as CHO cells. Monoclonal (e.g., human) antibodies may be produced by the expression of recombinant DNA in host cells or by expression in hybridoma cells as described herein.

The anti-Secs-1 antibodies of the invention may be employed in any known assay method, such as competitive binding assays, direct and indirect sandwich assays, and immunoprecipitation assays (Sola, *Monoclonal Antibodies: A Manual of Techniques* 147-158 (CRC Press, Inc., 1987)) for the detection and quantitation of Secs-1 polypeptides. The antibodies will bind Secs-1 polypeptides with an affinity that is appropriate for the assay method being employed.

For diagnostic applications, in certain embodiments, anti-Secs-1 antibodies may be labeled with a detectable moiety. The detectable moiety can be any one that is capable of producing, either directly or indirectly, a detectable signal. For example, the detectable moiety may be a radioisotope, such as $^3$H, $^{14}$C, $^{32}$P, $^{35}$S, $^{125}$I, $^{99}$Tc, $^{111}$In, or $^{67}$Ga; a fluorescent or chemiluminescent compound, such as fluorescein isothiocyanate, rhodamine, or luciferin; or an enzyme, such as alkaline phosphatase, β-galactosidase, or horseradish peroxidase (Bayer, et al., 1990, *Meth. Enz.* 184:138-63).

Competitive binding assays rely on the ability of a labeled standard (e.g., a Secs-1 polypeptide, or an immunologically reactive portion thereof) to compete with the test sample analyte (a Secs-1 polypeptide) for binding with a limited amount of anti-Secs-1 antibody. The amount of a Secs-1 polypeptide in the test sample is inversely proportional to the amount of standard that becomes bound to the antibodies. To facilitate determining the amount of standard that becomes bound, the antibodies typically are insolubilized before or after the competition, so that the standard and analyte that are bound to the antibodies may conveniently be separated from the standard and analyte which remain unbound.

Sandwich assays typically involve the use of two antibodies, each capable of binding to a different immunogenic portion, or epitope, of the protein to be detected and/or quantitated. In a sandwich assay, the test sample analyte is typically bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assays). For example, one type of sandwich assay is an enzyme-linked immunosorbent assay (ELISA), in which case the detectable moiety is an enzyme.

The selective binding agents, including anti-Secs-1 antibodies, are also useful for in vivo imaging. An antibody labeled with a detectable moiety may be administered to an animal, preferably into the bloodstream, and the presence and location of the labeled antibody in the host assayed. The antibody may be labeled with any moiety that is detectable in an animal, whether by nuclear magnetic resonance, radiology, or other detection means known in the art.

Selective binding agents of the invention, including antibodies, may be used as therapeutics. These therapeutic agents are generally agonists or antagonists, in that they either enhance or reduce, respectively, at least one of the biological activities of a Secs-1 polypeptide. In one embodiment, antagonist antibodies of the invention are antibodies or binding fragments thereof which are capable of specifically binding to a Secs-1 polypeptide and which are capable of inhibiting or eliminating the functional activity of a Secs-1 polypeptide in vivo or in vitro. In preferred embodiments, the selective binding agent, e.g., an antagonist antibody, will inhibit the functional activity of a Secs-1 polypeptide by at least about 50%, and preferably by at least about 80%. In another embodiment, the selective binding agent may be an anti-Secs-1 polypeptide antibody that is capable of interacting with a Secs-1 polypeptide binding partner (a ligand or receptor) thereby inhibiting or eliminating Secs-1 polypeptide activity in vitro or in vivo. Selective binding agents, including agonist and antagonist anti-Secs-1 polypeptide antibodies, are identified by screening assays that are well known in the art.

The invention also relates to a kit comprising Secs-1 selective binding agents (such as antibodies) and other reagents useful for detecting Secs-1 polypeptide levels in biological samples. Such reagents may include a detectable label, blocking serum, positive and negative control samples, and detection reagents.

The Secs-1 polypeptides of the present invention can be used to clone Secs-1 polypeptide receptors, using an expression cloning strategy. Radiolabeled (125-Iodine) Secs-1 polypeptide or affinity/activity-tagged Secs-1 polypeptide (such as an Fc fusion or an alkaline phosphatase fusion) can be used in binding assays to identify a cell type or cell line or tissue that expresses Secs-1 polypeptide receptors. RNA isolated from such cells or tissues can be converted to cDNA, cloned into a mammalian expression vector, and transfected into mammalian cells (such as COS or 293 cells) to create an expression library. A radiolabeled or tagged Secs-1 polypeptide can then be used as an affinity ligand to identify and isolate from this library the subset of cells that express the Secs-1 polypeptide receptors on their surface. DNA can then be isolated from these cells and transfected into mammalian cells to create a secondary expression library in which the fraction of cells expressing Secs-1 polypeptide receptors is many-fold higher than in the original library. This enrichment process can be repeated iteratively until a single recombinant clone containing a Secs-1 polypeptide receptor is isolated. Isolation of the Secs-1 polypeptide receptors is useful for identifying or developing novel agonists and antagonists of the Secs-1 polypeptide signaling pathway. Such agonists and antagonists include soluble Secs-1 polypeptide receptors, anti-Secs-1 polypeptide receptor antibodies, small molecules, or antisense oligonucleotides, and they may be used for treating, preventing, or diagnosing one or more of the diseases or disorders described herein.

Microarrays

It will be appreciated that DNA microarray technology can be utilized in accordance with the present invention. DNA microarrays are miniature, high-density arrays of nucleic acids positioned on a solid support, such as glass. Each cell or element within the array contains numerous copies of a single nucleic acid species that acts as a target for hybridization with a complementary nucleic acid sequence (e.g., mRNA). In expression profiling using DNA microarray technology, mRNA is first extracted from a cell or tissue sample and then converted enzymatically to fluorescently labeled cDNA. This material is hybridized to the microarray and unbound cDNA is removed by washing. The expression of discrete genes represented on the array is then visualized by quantitating the amount of labeled cDNA that is specifically bound to each target nucleic acid molecule. In this way, the expression of thousands of genes can be quantitated in a high throughput, parallel manner from a single sample of biological material.

This high throughput expression profiling has a broad range of applications with respect to the Secs-1 like molecules of the invention, including, but not limited to: the identification and validation of Secs-1 disease-related genes as targets for therapeutics; molecular toxicology of related Secs-1 molecules and inhibitors thereof; stratification of populations and generation of surrogate markers for clinical trials; and enhancing related Secs-1 polypeptide small molecule drug discovery by aiding in the identification of selective compounds in high throughput screens.

Chemical Derivatives

Chemically modified derivatives of Secs-1 polypeptides may be prepared by one skilled in the art, given the disclosures described herein. Secs-1 polypeptide derivatives are modified in a manner that is different—either in the type or location of the molecules naturally attached to the polypeptide. Derivatives may include molecules formed by the deletion of one or more naturally-attached chemical groups. The polypeptide comprising the amino acid sequence of SEQ ID NO: 2 or SEQ ID NO: 5 or a Secs-1 polypeptide variant may be modified by the covalent attachment of one or more polymers. For example, the polymer selected is typically water-soluble so that the protein to which it is attached does not precipitate in an aqueous environment, such as a physiological environment. Included within the scope of suitable polymers is a mixture of polymers. Preferably, for therapeutic use of the end-product preparation, the polymer will be pharmaceutically acceptable.

The polymers each may be of any molecular weight and may be branched or unbranched. The polymers each typically have an average molecular weight of between about 2 kDa to about 100 kDa (the term "about" indicating that in preparations of a water-soluble polymer, some molecules will weigh more, some less, than the stated molecular weight). The average molecular weight of each polymer is preferably between about 5 kDa and about 50 kDa, more preferably between about 12 kDa and about 40 kDa and most preferably between about 20 kDa and about 35 kDa.

Suitable water-soluble polymers or mixtures thereof include, but are not limited to, N-linked or O-linked carbohydrates, sugars, phosphates, polyethylene glycol (PEG) (including the forms of PEG that have been used to derivatize proteins, including mono-($C_1$-$C_{10}$), alkoxy-, or aryloxy-polyethylene glycol), monomethoxy-polyethylene glycol, dextran (such as low molecular weight dextran of, for example, about 6 kD), cellulose, or other carbohydrate based polymers, poly-(N-vinyl pyrrolidone) polyethylene glycol, propylene glycol homopolymers, polypropylene oxide/ethylene oxide co-polymers, polyoxyethylated polyols (e.g., glycerol), and polyvinyl alcohol. Also encompassed by the present invention are bifunctional crosslinking molecules which may be used to prepare covalently attached multimers of the polypeptide comprising the amino acid sequence of SEQ ID NO: 2 or SEQ ID NO: 5 or a Secs-1 polypeptide variant.

In general, chemical derivatization may be performed under any suitable condition used to react a protein with an activated polymer molecule. Methods for preparing chemical derivatives of polypeptides will generally comprise the steps of: (a) reacting the polypeptide with the activated polymer molecule (such as a reactive ester or aldehyde derivative of the polymer molecule) under conditions whereby the polypeptide comprising the amino acid sequence of SEQ ID NO: 2 or SEQ ID NO: 5 or a Secs-1 polypeptide variant becomes attached to one or more polymer molecules, and (b) obtaining the reaction products. The optimal reaction conditions will be determined based on known parameters and the desired result. For example, the larger the ratio of polymer molecules to protein, the greater the percentage of attached polymer molecule. In one embodiment, the Secs-1 polypeptide derivative may have a single polymer molecule moiety at the amino terminus. See, e.g., U.S. Pat. No. 5,234,784.

The pegylation of a polypeptide may be specifically carried out using any of the pegylation reactions known in the art. Such reactions are described, for example, in the following references: Francis et al., 1992, *Focus on Growth Factors* 3:4-10; EP Pub. Nos. 0154316 and 0401384; and U.S. Pat. No. 4,179,337. For example, pegylation may be carried out via an acylation reaction or an alkylation reaction with a reactive polyethylene glycol molecule (or an analogous reactive water-soluble polymer) as described herein. For the acylation reactions, a selected polymer should have a single reactive ester group. For reductive alkylation, a selected polymer should have a single reactive aldehyde group. A reactive aldehyde is, for example, polyethylene glycol propionaldehyde, which is water stable, or mono $C_1$-$C_{10}$ alkoxy or aryloxy derivatives thereof (see U.S. Pat. No. 5,252,714).

In another embodiment, Secs-1 polypeptides may be chemically coupled to biotin. The biotin/Secs-1 polypeptide molecules are then allowed to bind to avidin, resulting in tetravalent avidin/biotin/Secs-1 polypeptide molecules. Secs-1 polypeptides may also be covalently coupled to dinitrophenol (DNP) or trinitrophenol (TNP) and the resulting conjugates precipitated with anti-DNP or anti-TNP-IgM to form decameric conjugates with a valency of 10.

Generally, conditions that may be alleviated or modulated by the administration of the present Secs-1 polypeptide derivatives include those described herein for Secs-1 polypeptides. However, the Secs-1 polypeptide derivatives disclosed herein may have additional activities, enhanced or reduced biological activity, or other characteristics, such as increased or decreased half-life, as compared to the non-derivatized molecules.

Genetically Engineered Non-Human Animals

Additionally included within the scope of the present invention are non-human animals such as mice, rats, or other rodents; rabbits, goats, sheep, or other farm animals, in which the genes encoding native Secs-1 polypeptide have been disrupted (i.e., "knocked out") such that the level of expression of Secs-1 polypeptide is significantly decreased or completely abolished. Such animals may be prepared using techniques and methods such as those described in U.S. Pat. No. 5,557,032.

The present invention further includes non-human animals such as mice, rats, or other rodents; rabbits, goats, sheep, or other farm animals, in which either the native form of a Secs-1 gene for that animal or a heterologous Secs-1 gene is overexpressed by the animal, thereby creating a "transgenic" animal. Such transgenic animals may be prepared using well known methods such as those described in U.S. Pat. No 5,489,743 and PCT Pub. No. WO 94/28122.

The present invention further includes non-human animals in which the promoter for one or more of the Secs-1 polypeptides of the present invention is either activated or inactivated (e.g., by using homologous recombination methods) to alter the level of expression of one or more of the native Secs-1 polypeptides.

These non-human animals may be used for drug candidate screening. In such screening, the impact of a drug candidate on the animal may be measured. For example, drug candidates may decrease or increase the expression of the Secs-1 gene. In certain embodiments, the amount of Secs-1 polypeptide that is produced may be measured after the exposure of the animal to the drug candidate. Additionally, in certain embodiments, one may detect the actual impact of the drug candidate on the animal. For example, over-expression of a particular gene may result in, or be associated with, a disease or pathological condition. In such cases, one may test a drug candidate's ability to decrease expression of the gene or its ability to prevent or inhibit a pathological condition. In other examples, the production of a particular metabolic product such as a fragment of a polypeptide, may result in, or be associated with, a disease or pathological condition. In such cases, one may test a drug candidate's ability to decrease the production of such a metabolic product or its ability to prevent or inhibit a pathological condition.

Assaying for Other Modulators of Secs-1 Polypeptide Activity

In some situations, it may be desirable to identify molecules that are modulators, i.e., agonists or antagonists, of the activity of Secs-1 polypeptide. Natural or synthetic molecules that modulate Secs-1 polypeptide may be identified using one or more screening assays, such as those described herein. Such molecules may be administered either in an ex vivo manner or in an in vivo manner by injection, or by oral delivery, implantation device, or the like.

"Test molecule" refers to a molecule that is under evaluation for the ability to modulate (i.e., increase or decrease) the activity of a Secs-1 polypeptide. Most commonly, a test molecule will interact directly with a Secs-1 polypeptide. However, it is also contemplated that a test molecule may also modulate Secs-1 polypeptide activity indirectly, such as by affecting Secs-1 gene expression, or by binding to a Secs-1 polypeptide binding partner (e.g., receptor or ligand). In one embodiment, a test molecule will bind to a Secs-1 polypeptide with an affinity constant of at least about $10^{-6}$ M, preferably about $10^{-8}$ M, more preferably about $10^{-9}$ M, and even more preferably about $10^{-10}$ M.

Methods for identifying compounds that interact with Secs-1 polypeptides are encompassed by the present invention. In certain embodiments, a Secs-1 polypeptide is incubated with a test molecule under conditions that permit the interaction of the test molecule with a Secs-1 polypeptide, and the extent of the interaction is measured. The test molecule can be screened in a substantially purified form or in a crude mixture.

In certain embodiments, a Secs-1 polypeptide agonist or antagonist may be a protein, peptide, carbohydrate, lipid, or small molecular weight molecule that interacts with Secs-1 polypeptide to regulate its activity. Molecules which regulate Secs-1 polypeptide expression include nucleic acids which are complementary to nucleic acids encoding a Secs-1 polypeptide, or are complementary to nucleic acids sequences which direct or control the expression of Secs-1 polypeptide, and which act as anti-sense regulators of expression.

Once a test molecule has been identified as interacting with a Secs-1 polypeptide, the molecule may be further evaluated for its ability to increase or decrease Secs-1 polypeptide activity. The measurement of the interaction of a test molecule with Secs-1 polypeptide may be carried out in several formats, including cell-based binding assays, membrane binding assays, solution-phase assays, and immunoassays. In general, a test molecule is incubated with a Secs-1 polypeptide for a specified period of time, and Secs-1 polypeptide activity is determined by one or more assays for measuring biological activity.

The interaction of test molecules with Secs-1 polypeptides may also be assayed directly using polyclonal or monoclonal antibodies in an immunoassay. Alternatively, modified forms of Secs-1 polypeptides containing epitope tags as described herein may be used in solution and immunoassays.

In the event that Secs-1 polypeptides display biological activity through an interaction with a binding partner (e.g., a receptor or a ligand), a variety of in vitro assays may be used to measure the binding of a Secs-1 polypeptide to the corresponding binding partner (such as a selective binding agent, receptor, or ligand). These assays may be used to screen test molecules for their ability to increase or decrease the rate and/or the extent of binding of a Secs-1 polypeptide to its binding partner. In one assay, a Secs-1 polypeptide is immobilized in the wells of a microtiter plate. Radiolabeled Secs-1 polypeptide binding partner (for example, iodinated Secs-1 polypeptide binding partner) and a test molecule can then be added either one at a time (in either order) or simultaneously to the wells. After incubation, the wells can be washed and counted for radioactivity, using a scintillation counter, to determine the extent to which the binding partner bound to the Secs-1 polypeptide. Typically, a molecule will be tested over a range of concentrations, and a series of control wells lacking one or more elements of the test assays can be used for accuracy in the evaluation of the results. An alternative to this method involves reversing the "positions" of the proteins, i.e., immobilizing Secs-1 polypeptide binding partner to the microtiter plate wells, incubating with the test molecule and radiolabeled Secs-1 polypeptide, and determining the extent of Secs-1 polypeptide binding. See, e.g., *Current Protocols in Molecular Biology*, chap. 18 (Ausubel et al., eds., Green Publishers Inc. and Wiley and Sons 1995).

As an alternative to radiolabeling, a Secs-1 polypeptide or its binding partner may be conjugated to biotin, and the presence of biotinylated protein can then be detected using streptavidin linked to an enzyme, such as horse radish peroxidase (HRP) or alkaline phosphatase (AP), which can be detected colorometrically, or by fluorescent tagging of streptavidin. An antibody directed to a Secs-1 polypeptide or to a Secs-1 polypeptide binding partner, and which is conjugated to biotin, may also be used for purposes of detection following incubation of the complex with enzyme-linked streptavidin linked to AP or HRP.

A Secs-1 polypeptide or a Secs-1 polypeptide binding partner can also be immobilized by attachment to agarose beads, acrylic beads, or other types of such inert solid phase substrates. The substrate-protein complex can be placed in a solution containing the complementary protein and the test compound. After incubation, the beads can be precipitated by centrifugation, and the amount of binding between a Secs-1 polypeptide and its binding partner can be assessed using the methods described herein. Alternatively, the substrate-protein complex can be immobilized in a column with the test molecule and complementary protein passing through the column. The formation of a complex between a Secs-1 polypeptide and its binding partner can then be assessed using any of the techniques described herein (e.g., radiolabelling or antibody binding).

Another in vitro assay that is useful for identifying a test molecule which increases or decreases the formation of a complex between a Secs-1 polypeptide binding protein and a Secs-1 polypeptide binding partner is a surface plasmon resonance detector system such as the BIAcore® assay system (Pharmacia AB Corp., Piscataway, N.J.). The BIAcore® system is utilized as specified by the manufacturer. This assay essentially involves the covalent binding of either Secs-1 polypeptide or a Secs-1 polypeptide binding partner to a dextran-coated sensor chip that is located in a detector. The test compound and the other complementary protein can then be injected, either simultaneously or sequentially, into the chamber containing the sensor chip. The amount of complementary protein that binds can be assessed based on the change in molecular mass that is physically associated with the dextran-coated side of the sensor chip, with the change in molecular mass being measured by the detector system.

In some cases, it may be desirable to evaluate two or more test compounds together for their ability to increase or decrease the formation of a complex between a Secs-1 polypeptide and a Secs-1 polypeptide binding partner. In these cases, the assays set forth herein can be readily modified by adding such additional test compound(s) either simultaneously with, or subsequent to, the first test compound. The remainder of the steps in the assay are as set forth herein.

In vitro assays such as those described herein may be used advantageously to screen large numbers of compounds for an effect on the formation of a complex between a Secs-1 polypeptide and Secs-1 polypeptide binding partner. The assays may be automated to screen compounds generated in phage display, synthetic peptide, and chemical synthesis libraries.

Compounds which increase or decrease the formation of a complex between a Secs-1 polypeptide and a Secs-1 polypeptide binding partner may also be screened in cell culture using cells and cell lines expressing either Secs-1 polypeptide or Secs-1 polypeptide binding partner. Cells and cell lines may be obtained from any mammal, but preferably will be from human or other primate, canine, or rodent sources. The binding of a Secs-1 polypeptide to cells expressing Secs-1 polypeptide binding partner at the surface is evaluated in the presence or absence of test molecules, and the extent of binding may be determined by, for example, flow cytometry using a biotinylated antibody to a Secs-1 polypeptide binding partner. Cell culture assays can be used advantageously to further evaluate compounds that score positive in protein binding assays described herein.

Cell cultures can also be used to screen the impact of a drug candidate.

For example, drug candidates may decrease or increase the expression of the Secs-1 gene. In certain embodiments, the amount of Secs-1 polypeptide or a Secs-1 polypeptide fragment that is produced may be measured after exposure of the cell culture to the drug candidate. In certain embodiments, one may detect the actual impact of the drug candidate on the cell culture. For example, the over-expression of a particular gene may have a particular impact on the cell culture. In such cases, one may test a drug candidate's ability to increase or decrease the expression of the gene or its ability to prevent or inhibit a particular impact on the cell culture. In other examples, the production of a particular metabolic product such as a fragment of a polypeptide, may result in, or be associated with, a disease or pathological condition. In such cases, one may test a drug candidate's ability to decrease the production of such a metabolic product in a cell culture.

Internalizing Proteins

The tat protein sequence (from HIV) can be used to internalize proteins into a cell. See, e.g., Falwell et al., 1994, *Proc. Natl. Acad. Sci. USA.* 91:664-68. For example, an 11 amino acid sequence (Y-G-R-K-K-R-R-Q-R-R-R; SEQ ID NO: 12) of the HIV tat protein (termed the "protein transduction domain," or TAT PDT) has been described as mediating delivery across the cytoplasmic membrane and the nuclear membrane of a cell. See Schwarze et al., 1999, *Science* 285:1569-72; and Nagahara et al., 1998, *Nat. Med.* 4:1449-52. In these procedures, FITC-constructs (FITC-labeled G-G-G-G-Y-G-R-K-K-R-R-Q-R-R-R; SEQ ID NO: 13), which penetrate tissues following intraperitoneal administration, are prepared, and the binding of such constructs to cells is detected by fluorescence-activated cell sorting (FACS) analysis. Cells treated with a tat-β-gal fusion protein will demonstrate β-gal activity. Following injection, expression of such a construct can be detected in a number of tissues, including liver, kidney, lung, heart, and brain tissue. It is believed that such constructs undergo some degree of unfolding in order to enter the cell, and as such, may require a refolding following entry into the cell.

It will thus be appreciated that the tat protein sequence may be used to internalize a desired polypeptide into a cell. For example, using the tat protein sequence, a Secs-1 antagonist (such as an anti-Secs-1 selective binding agent, small molecule, soluble receptor, or antisense oligonucleotide) can be administered intracellularly to inhibit the activity of a Secs-1 molecule. As used herein, the term "Secs-1 molecule" refers to both Secs-1 nucleic acid molecules and Secs-1 polypeptides as defined herein. Where desired, the Secs-1 protein itself may also be internally administered to a cell using these procedures. See also, Straus, 1999, *Science* 285:1466-67.

Cell Source Identification Using Secs-1 Polypeptide

In accordance with certain embodiments of the invention, it may be useful to be able to determine the source of a certain cell type associated with a Secs-1 polypeptide. For example, it may be useful to determine the origin of a disease or pathological condition as an aid in selecting an appropriate therapy. Secs-1 polypeptide is specifically associated with epithelial cells, specifically epithelial cells of the cheek, tongue, esophagus, large intestine, uterus, thymus, nipple, skin, and nasal cavity. In certain embodiments, nucleic acids encoding a Secs-1 polypeptide can be used as a probe to identify cells described herein by screening the nucleic acids of the cells with such a probe. In other embodiments, one may use anti-Secs-1 polypeptide antibodies to test for the presence of Secs-1 polypeptide in cells, and thus, determine if such cells are of the types described herein.

Therapeutic Uses

The Secs-1 nucleic acid molecules, polypeptides, and agonists and antagonists thereof can be used to treat, diagnose, ameliorate, or prevent a number of acute and chronic diseases or conditions, including those recited herein.

The Secs-1 gene is primarily expressed in the gastrointestinal tract, as determined by in situ hybridization. Based on this expression pattern, Secs-1 polypeptides may play a role in gastrointestinal development and function. Accordingly, Secs-1 nucleic acid molecules, polypeptides, and agonists and antagonists thereof (including, but not limited to, anti-Secs-1 selective binding agents) may be useful in the diagnosis and/or treatment of diseases involving the gastrointestinal tract. Examples of such diseases include, but are not limited to, gastrointestinal ulcers, reflux esophagitis, coeliac disease, diabetes, ischemia-reperfusion injury, Crohn's disease, inflammatory bowel disease, and bacterial and viral-induced infections and colitis. In addition, Secs-1 nucleic acid molecules, polypeptides, and agonists and antagonists thereof may be useful in the treatment of chemotherapy or radiation-induced gastrointestinal damage. Other diseases associated with gastrointestinal development and function are encompassed by the scope of this invention.

Based on the expression of the Secs-1 gene in the gastrointestinal tract, Secs-1 nucleic acid molecules, polypeptides, agonists and antagonists thereof (including, but not limited to, anti-Secs-1 selective binding agents) may also be useful for the diagnosis and/or treatment of diseases involving digestion or metabolism. Examples of such diseases include, but are not limited to, obesity, gastrointestinal reflux, diverticulitis, diverticulosis, enteritis, and dysphagia. Other such metabolic disorders are encompassed by the scope of this invention.

Since Secs-1 polypeptide expression has been detected in the tongue and oral mucosa, Secs-1 nucleic acid molecules, polypeptides, agonists and antagonists thereof (including, but not limited to, anti-Secs-1 selective binding agents) may also be useful for the diagnosis and/or treatment of diseases associated with the oral cavity. Examples of such diseases include, but are not limited to, periodontal disease, oral cancer, and chemotherapy or radiation-induced mucositis. Other diseases associated with the oral cavity are encompassed by the scope of this invention.

The differential expression of Secs-1 polypeptides in tumor cells and normal cells suggests that Secs-1 polypeptides may play a role in metastatic disease. Accordingly, Secs-1 nucleic acid molecules, polypeptides, agonists and antagonists thereof (including, but not limited to, anti-Secs-1 selective binding agents) may play a role in the diagnosis and/or treatment of cancer. Examples of such diseases include, but are not limited to, cancer of the colon, stomach, throat, esophagus, breast, prostate, uterus, testis, or lung. Other cancers and metastatic diseases are encompassed by the scope of this invention.

Significant levels of Secs-1 polypeptide expression were also detected in the testis and uterus. Therefore, Secs-1 nucleic acid molecules, polypeptides, agonists and antagonists thereof (including, but not limited to, anti-Secs-1 selective binding agents) may play a role in the diagnosis and/or treatment of fertility disorders. Examples of such diseases include, but are not limited to, male infertility, fertility enhancement, endometriosis, fibroid, or menstruation. Other disorders associated with fertility are encompassed by the scope of this invention.

Other diseases caused by or mediated by undesirable levels of Secs-1 polypeptides are encompassed within the scope of the invention. Undesirable levels include excessive levels of Secs-1 polypeptides and sub-normal levels of Secs-1 polypeptides.

Secs-1 Polypeptide Compositions and Administration

Therapeutic compositions are within the scope of the present invention.

Such SECS-1 polypeptide pharmaceutical compositions may comprise a therapeutically effective amount of a Secs-1 polypeptide or a Secs-1 nucleic acid molecule in admixture with a pharmaceutically or physiologically acceptable formulation agent selected for suitability with the mode of administration. Pharmaceutical compositions may comprise a therapeutically effective amount of one or more Secs-1 polypeptide selective binding agents in admixture with a pharmaceutically or physiologically acceptable formulation agent selected for suitability with the mode of administration.

Acceptable formulation materials preferably are nontoxic to recipients at the dosages and concentrations employed.

The pharmaceutical composition may contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants. See *Remington's Pharmaceutical Sciences* (18th Ed., A. R. Gennaro, ed., Mack Publishing Company 1990.

The optimal pharmaceutical composition will be determined by a skilled artisan depending upon, for example, the intended route of administration, delivery format, and desired dosage. See, e.g., *Remington's Pharmaceutical Sciences*, supra. Such compositions may influence the physical state, stability, rate of in vivo release, and rate of in vivo clearance of the Secs-1 molecule.

The primary vehicle or carrier in a pharmaceutical composition may be either aqueous or non-aqueous in nature. For example, a suitable vehicle or carrier for injection may be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute. In one embodiment of the present invention, Secs-1 polypeptide compositions may be prepared for storage by mixing the selected composition having the desired degree of purity with optional formulation agents (*Remington's Pharmaceutical Sciences*, supra) in the form of a lyophilized cake or an aqueous solution. Further, the Secs-1 polypeptide product may be formulated as a lyophilizate using appropriate excipients such as sucrose.

The Secs-1 polypeptide pharmaceutical compositions can be selected for parenteral delivery. Alternatively, the compositions may be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use in this invention may be in the form of a pyrogen-free, parenterally acceptable, aqueous solution comprising the desired Secs-1 molecule in a pharmaceutically acceptable vehicle. A particularly suitable vehicle for parenteral injection is sterile distilled water in which a Secs-1 molecule is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In one embodiment, a pharmaceutical composition may be formulated for inhalation. For example, Secs-1 polypeptide may be formulated as a dry powder for inhalation. Secs-1 polypeptide or nucleic acid molecule inhalation solutions may also be formulated with a propellant for aerosol delivery. In yet another embodiment, solutions may be nebulized. Pulmonary administration is further described in PCT Pub. No. WO 94/20069, which describes the pulmonary delivery of chemically modified proteins.

It is also contemplated that certain formulations may be administered orally. In one embodiment of the present invention, Secs-1 polypeptides that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the Secs-1 polypeptide. Diluents, flavorings, low melting point waxes, vegetable oils, lubricants, suspending agents, tablet disintegrating agents, and binders may also be employed.

Another pharmaceutical composition may involve an effective quantity of Secs-1 polypeptides in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional Secs-1 polypeptide pharmaceutical compositions will be evident to those skilled in the art, including formulations involving Secs-1 polypeptides in sustained- or controlled-delivery formulations. Techniques for formulating a variety of other sustained- or controlled-delivery means, such as liposome carriers, bio-erodible microparticles or porous beads and depot injections, are also known to those skilled in the art. See, e.g., PCT/US93/00829, which describes the controlled release of porous polymeric microparticles for the delivery of pharmaceutical compositions.

Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919 and EP Pub. No. 058481), copolymers of L-glutamic acid and gamma ethyl-L-glutamate (Sidman et al., 1983, *Biopolymers* 22:547-56), poly(2-hydroxyethyl-methacrylate) (Langer et al., 1981, *J. Biomed. Mater. Res.* 15:167-277 and Langer, 1982, *Chem. Tech.* 12:98-105), ethylene vinyl acetate (Langer et al., supra) or poly-D(−)-3-hydroxybutyric acid (EP Pub. No. 133988). Sustained-release compositions may also include liposomes, which can be prepared by any of several methods known in the art. See, e.g., Eppstein et al., 1985, *Proc. Natl. Acad. Sci. USA* 82:3688-92; and EP Pub. Nos. 036676, 088046, and 143949.

The Secs-1 pharmaceutical composition to be used for in vivo administration typically must be sterile. This may be accomplished by filtration through sterile filtration membranes. Where the composition is lyophilized, sterilization using this method may be conducted either prior to, or following, lyophilization and reconstitution. The composition for parenteral administration may be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or as a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

The effective amount of a Secs-1 pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the Secs-1 molecule is being used, the route of administration, and the size (body weight, body surface, or organ size) and condition (the age and general health) of the patient. Accordingly, the clinician may titer the dosage and modify the route of administration to obtain the optimal therapeutic effect. A typical dosage may range from about 0.1 µg/kg to up to about 100 mg/kg or more, depending on the factors mentioned above. In other embodiments, the dosage may range from 0.1 µg/kg up to about 100 mg/kg; or 1 µg/kg up to about 100 mg/kg; or 5 µg/kg up to about 100 mg/kg.

The frequency of dosing will depend upon the pharmacokinetic parameters of the Secs-1 molecule in the formulation being used. Typically, a clinician will administer the composition until a dosage is reached that achieves the desired effect. The composition may therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraocular, intraarterial, intraportal, or intralesional routes; by sustained release systems; or by implantation devices. Where desired, the compositions may be administered by bolus injection or continuously by infusion, or by implantation device.

Alternatively or additionally, the composition may be administered locally via implantation of a membrane, sponge, or other appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

In some cases, it may be desirable to use Secs-1 polypeptide pharmaceutical compositions in an ex vivo manner. In such instances, cells, tissues, or organs that have been removed from the patient are exposed to Secs-1 polypeptide pharmaceutical compositions after which the cells, tissues, or organs are subsequently implanted back into the patient.

In other cases, a Secs-1 polypeptide can be delivered by implanting certain cells that have been genetically engineered, using methods such as those described herein, to express and secrete the Secs-1 polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

As discussed herein, it may be desirable to treat isolated cell populations (such as stem cells, lymphocytes, red blood cells, chondrocytes, neurons, and the like) with one or more Secs-1 polypeptides. This can be accomplished by exposing the isolated cells to the polypeptide directly, where it is in a form that is permeable to the cell membrane.

Additional embodiments of the present invention relate to cells and methods (e.g., homologous recombination and/or other recombinant production methods) for both the in vitro production of therapeutic polypeptides and for the production and delivery of therapeutic polypeptides by gene therapy or cell therapy. Homologous and other recombination methods may be used to modify a cell that contains a normally transcriptionally-silent Secs-1 gene, or an under-expressed gene, and thereby produce a cell which expresses therapeutically efficacious amounts of Secs-1 polypeptides.

Homologous recombination is a technique originally developed for targeting genes to induce or correct mutations in transcriptionally active genes. Kucherlapati, 1989, *Prog. in Nucl. Acid Res. & Mol. Biol.* 36:301. The basic technique was developed as a method for introducing specific mutations into specific regions of the mammalian genome (Thomas et al., 1986, *Cell* 44:419-28; Thomas and Capecchi, 1987, *Cell* 51:503-12; Doetschman et al., 1988, *Proc. Natl. Acad. Sci. U.S.A.* 85:8583-87) or to correct specific mutations within defective genes (Doetschman et al., 1987, *Nature* 330:576-78). Exemplary homologous recombination techniques are described in U.S. Pat. No. 5,272,071; EP Pub. Nos. 9193051 and 505500; PCT/US90/07642, and PCT Pub No. WO 91/09955).

Through homologous recombination, the DNA sequence to be inserted into the genome can be directed to a specific region of the gene of interest by attaching it to targeting DNA. The targeting DNA is a nucleotide sequence that is complementary (homologous) to a region of the genomic DNA. Small pieces of targeting DNA that are complementary to a specific region of the genome are put in contact with the parental strand during the DNA replication process. It is a general property of DNA that has been inserted into a cell to hybridize, and therefore, recombine with other pieces of endogenous DNA through shared homologous regions. If this complementary strand is attached to an oligonucleotide that contains a mutation or a different sequence or an additional nucleotide, it too is incorporated into the newly synthesized strand as a result of the recombination. As a result of the proofreading function, it is possible for the new sequence of DNA to serve as the template. Thus, the transferred DNA is incorporated into the genome.

Attached to these pieces of targeting DNA are regions of DNA that may interact with or control the expression of a Secs-1 polypeptide, e.g., flanking sequences. For example, a promoter/enhancer element, a suppressor, or an exogenous transcription modulatory element is inserted in the genome of the intended host cell in proximity and orientation sufficient to influence the transcription of DNA encoding the desired Secs-1 polypeptide. The control element controls a portion of the DNA present in the host cell genome. Thus, the expression of the desired Secs-1 polypeptide may be achieved not by transfection of DNA that encodes the Secs-1 gene itself, but rather by the use of targeting DNA (containing regions of homology with the endogenous gene of interest) coupled with DNA regulatory segments that provide the endogenous gene sequence with recognizable signals for transcription of a Secs-1 gene.

In an exemplary method, the expression of a desired targeted gene in a cell (i.e., a desired endogenous cellular gene) is altered via homologous recombination into the cellular genome at a preselected site, by the introduction of DNA which includes at least a regulatory sequence, an exon, and a splice donor site. These components are introduced into the chromosomal (genomic) DNA in such a manner that this, in effect, results in the production of a new transcription unit (in which the regulatory sequence, the exon, and the splice donor site present in the DNA construct are operatively linked to the endogenous gene). As a result of the introduction of these components into the chromosomal DNA, the expression of the desired endogenous gene is altered.

Altered gene expression, as described herein, encompasses activating (or causing to be expressed) a gene which is normally silent (unexpressed) in the cell as obtained, as well as increasing the expression of a gene which is not expressed at physiologically significant levels in the cell as obtained. The embodiments further encompass changing the pattern of regulation or induction such that it is different from the pattern of regulation or induction that occurs in the cell as obtained, and reducing (including eliminating) the expression of a gene which is expressed in the cell as obtained.

One method by which homologous recombination can be used to increase, or cause, Secs-1 polypeptide production from a cell's endogenous Secs-1 gene involves first using homologous recombination to place a recombination sequence from a site-specific recombination system (e.g., Cre/loxP, FLP/FRT) (Sauer, 1994, *Curr. Opin. Biotechnol.*, 5:521-27; Sauer, 1993, *Methods Enzymol.*, 225:890-900) upstream of (i.e., 5' to) the cell's endogenous genomic Secs-1 polypeptide coding region. A plasmid containing a recombination site homologous to the site that was placed just upstream of the genomic Secs-1 polypeptide coding region is introduced into the modified cell line along with the appropriate recombinase enzyme. This recombinase causes the plasmid to integrate, via the plasmid's recombination site, into the recombination site located just upstream of the genomic Secs-1 polypeptide coding region in the cell line (Baubonis and Sauer, 1993, *Nucleic Acids Res.* 21:2025-29; O'Gorman et al., 1991, *Science* 251:1351-55). Any flanking sequences known to increase transcription (e.g., enhancer/promoter, intron, translational enhancer), if properly positioned in this plasmid, would integrate in such a manner as to create a new or modified transcriptional unit resulting in de novo or increased Secs-1 polypeptide production from the cell's endogenous Secs-1 gene.

A further method to use the cell line in which the site specific recombination sequence had been placed just upstream of the cell's endogenous genomic Secs-1 polypeptide coding region is to use homologous recombination to introduce a second recombination site elsewhere in the cell line's genome. The appropriate recombinase enzyme is then introduced into the two-recombination-site cell line, causing a recombination event (deletion, inversion, and translocation) (Sauer, 1994, *Curr. Opin. Biotechnol.*, 5:521-27; Sauer, 1993, *Methods Enzymol*, 225:890-900) that would create a new or modified transcriptional unit resulting in de novo or increased Secs-1 polypeptide production from the cell's endogenous Secs-1 gene.

An additional approach for increasing, or causing, the expression of Secs-1 polypeptide from a cell's endogenous Secs-1 gene involves increasing, or causing, the expression of a gene or genes (e.g., transcription factors) and/or decreasing the expression of a gene or genes (e.g., transcriptional repressors) in a manner which results in de novo or increased Secs-1 polypeptide production from the cell's endogenous Secs-1 gene. This method includes the introduction of a non-naturally occurring polypeptide (e.g., a polypeptide comprising a site specific DNA binding domain fused to a transcriptional factor domain) into the cell such that de novo or increased Secs-1 polypeptide production from the cell's endogenous Secs-1 gene results.

The present invention further relates to DNA constructs useful in the method of altering expression of a target gene. In certain embodiments, the exemplary DNA constructs comprise: (a) one or more targeting sequences, (b) a regulatory sequence, (c) an exon, and (d) an unpaired splice-donor site. The targeting sequence in the DNA construct directs the integration of elements (a)-(d) into a target gene in a cell such that the elements (b)-(d) are operatively linked to sequences of the endogenous target gene. In another embodiment, the DNA constructs comprise: (a) one or more targeting sequences, (b) a regulatory sequence, (c) an exon, (d) a splice-donor site, (e) an intron, and (f) a splice-acceptor site, wherein the targeting sequence directs the integration of elements (a)-(f) such that the elements of (b)-(f) are operatively linked to the endogenous gene. The targeting sequence is homologous to the preselected site in the cellular chromosomal DNA with which homologous recombination is to occur. In the construct, the exon is generally 3' of the regulatory sequence and the splice-donor site is 3' of the exon.

If the sequence of a particular gene is known, such as the nucleic acid sequence of Secs-1 polypeptide presented herein, a piece of DNA that is complementary to a selected region of the gene can be synthesized or otherwise obtained, such as by appropriate restriction of the native DNA at specific recognition sites bounding the region of interest. This piece serves as a targeting sequence upon insertion into the cell and will hybridize to its homologous region within the genome. If this hybridization occurs during DNA replication, this piece of DNA, and any additional sequence attached thereto, will act as an Okazaki fragment and will be incorporated into the newly synthesized daughter strand of DNA. The present invention, therefore, includes nucleotides encoding a Secs-1 polypeptide, which nucleotides may be used as targeting sequences.

Secs-1 polypeptide cell therapy, e.g., the implantation of cells producing Secs-1 polypeptides, is also contemplated. This embodiment involves implanting cells capable of synthesizing and secreting a biologically active form of Secs-1 polypeptide. Such Secs-1 polypeptide-producing cells can be cells that are natural producers of Secs-1 polypeptides or may be recombinant cells whose ability to produce Secs-1 polypeptides has been augmented by transformation with a gene encoding the desired Secs-1 polypeptide or with a gene augmenting the expression of Secs-1 polypeptide. Such a modification may be accomplished by means of a vector suitable for delivering the gene as well as promoting its expression and secretion. In order to minimize a potential immunological reaction in patients being administered a Secs-1 polypeptide, as may occur with the administration of a polypeptide of a foreign species, it is preferred that the natural cells producing Secs-1 polypeptide be of human origin and produce human Secs-1 polypeptide. Likewise, it is preferred that the recombinant cells producing Secs-1 polypeptide be transformed with an expression vector containing a gene encoding a human Secs-1 polypeptide.

Implanted cells may be encapsulated to avoid the infiltration of surrounding tissue. Human or non-human animal cells may be implanted in patients in biocompatible, semipermeable polymeric enclosures or membranes that allow the release of Secs-1 polypeptide, but that prevent the destruction of the cells by the patient's immune system or by other detrimental factors from the surrounding tissue. Alternatively, the patient's own cells, transformed to produce Secs-1 polypeptides ex vivo, may be implanted directly into the patient without such encapsulation.

Techniques for the encapsulation of living cells are known in the art, and the preparation of the encapsulated cells and their implantation in patients may be routinely accomplished. For example, Baetge et al. (PCT Pub. No. WO 95/05452 and PCT/US94/09299) describe membrane capsules containing genetically engineered cells for the effective delivery of biologically active molecules. The capsules are biocompatible and are easily retrievable. The capsules encapsulate cells transfected with recombinant DNA molecules comprising DNA sequences coding for biologically active molecules operatively linked to promoters that are not subject to down-regulation in vivo upon implantation into a mammalian host. The devices provide for the delivery of the molecules from living cells to specific sites within a recipient. In addition, see U.S. Pat. Nos. 4,892,538; 5,011,472; and 5,106,627. A system for encapsulating living cells is described in PCT Pub. No. WO 91/10425 (Aebischer et al.). See also, PCT Pub. No. WO 91/10470 (Aebischer et al.); Winn et al., 1991, *Exper. Neurol.* 113:322-29; Aebischer et al., 1991, *Exper. Neurol.* 111:269-75; and Tresco et al., 1992, *ASAIO* 38:17-23.

In vivo and in vitro gene therapy delivery of Secs-1 polypeptides is also envisioned. One example of a gene therapy technique is to use the Secs-1 gene (either genomic DNA, cDNA, and/or synthetic DNA) encoding a Secs-1 polypeptide which may be operably linked to a constitutive or inducible promoter to form a "gene therapy DNA construct." The promoter may be homologous or heterologous to the endogenous Secs-1 gene, provided that it is active in the cell or tissue type into which the construct will be inserted. Other components of the gene therapy DNA construct may optionally include DNA molecules designed for site-specific integration (e.g., endogenous sequences useful for homologous recombination), tissue-specific promoters, enhancers or silencers, DNA molecules capable of providing a selective advantage over the parent cell, DNA molecules useful as labels to identify transformed cells, negative selection systems, cell specific binding agents (as, for example, for cell targeting), cell-specific internalization factors, transcription factors enhancing expression from a vector, and factors enabling vector production.

A gene therapy DNA construct can then be introduced into cells (either ex vivo or in vivo) using viral or non-viral vectors. One means for introducing the gene therapy DNA construct is by means of viral vectors as described herein. Certain vectors, such as retroviral vectors, will deliver the DNA construct to the chromosomal DNA of the cells, and the gene can integrate into the chromosomal DNA. Other vectors will function as episomes, and the gene therapy DNA construct will remain in the cytoplasm.

In yet other embodiments, regulatory elements can be included for the controlled expression of the Secs-1 gene in the target cell. Such elements are turned on in response to an appropriate effector. In this way, a therapeutic polypeptide can be expressed when desired. One conventional control means involves the use of small molecule dimerizers or rapalogs to dimerize chimeric proteins which contain a small molecule-binding domain and a domain capable of initiating a biological process, such as a DNA-binding protein or transcriptional activation protein (see PCT Pub. Nos. WO 96/41865, WO 97/31898, and WO 97/31899). The dimerization of the proteins can be used to initiate transcription of the transgene.

An alternative regulation technology uses a method of storing proteins expressed from the gene of interest inside the cell as an aggregate or cluster. The gene of interest is expressed as a fusion protein that includes a conditional aggregation domain that results in the retention of the aggregated protein in the endoplasmic reticulum. The stored proteins are stable and inactive inside the cell. The proteins can be released, however, by administering a drug (e.g., small molecule ligand) that removes the conditional aggregation domain and thereby specifically breaks apart the aggregates or clusters so that the proteins may be secreted from the cell. See Aridor et al., 2000, *Science* 287:816-17 and Rivera et al., 2000, *Science* 287:826-30.

Other suitable control means or gene switches include, but are not limited to, the systems described herein. Mifepristone (RU486) is used as a progesterone antagonist. The binding of a modified progesterone receptor ligand-binding domain to the progesterone antagonist activates transcription by forming a dimer of two transcription factors that then pass into the nucleus to bind DNA. The ligand-binding domain is. modified to eliminate the ability of the receptor to bind to the natural ligand. The modified steroid hormone receptor system is further described in U.S. Pat. No. 5,364,791 and PCT Pub. Nos. WO 96/40911 and WO 97/10337.

Yet another control system uses ecdysone (a fruit fly steroid hormone) which binds to and activates an ecdysone receptor (cytoplasmic receptor). The receptor then translocates to the nucleus to bind a specific DNA response element (promoter from ecdysone-responsive gene). The ecdysone receptor includes a transactivation domain, DNA-binding domain, and ligand-binding domain to initiate transcription. The ecdysone system is further described in U.S. Pat. No. 5,514,578 and PCT Pub. Nos. WO 97/38117, WO 96/37609, and WO 93/03162.

Another control means uses a positive tetracycline-controllable transactivator. This system involves a mutated tet repressor protein DNA-binding domain (mutated tet R-4 amino acid changes which resulted in a reverse tetracycline-regulated transactivator protein, i.e., it binds to a tet operator in the presence of tetracycline) linked to a polypeptide which activates transcription. Such systems are described in U.S. Pat. Nos. 5,464,758, 5,650,298, and 5,654,168.

Additional expression control systems and nucleic acid constructs are described in U.S. Pat. Nos. 5,741,679 and 5,834,186, to Innovir Laboratories Inc.

In vivo gene therapy may be accomplished by introducing the gene encoding Secs-1 polypeptide into cells via local injection of a Secs-1 nucleic acid molecule or by other appropriate viral or non-viral delivery vectors. Hefti, 1994, *Neurobiology* 25:1418-35. For example, a nucleic acid molecule encoding a Secs-1 polypeptide may be contained in an adeno-associated virus (AAV) vector for delivery to the targeted cells (see, e.g., Johnson, PCT Pub. No. WO 95/34670; PCT App. No. PCT/US95/07178). The recombinant AAV genome typically contains AAV inverted terminal repeats flanking a DNA sequence encoding a Secs-1 polypeptide operably linked to functional promoter and polyadenylation sequences.

Alternative suitable viral vectors include, but are not limited to, retrovirus, adenovirus, herpes simplex virus, lentivirus, hepatitis virus, parvovirus, papovavirus, poxvirus, alphavirus, coronavirus, rhabdovirus, paramyxovirus, and papilloma virus vectors. U.S. Pat. No. 5,672,344 describes an in vivo viral-mediated gene transfer system involving a recombinant neurotrophic HSV-1 vector. U.S. Pat. No. 5,399,346 provides examples of a process for providing a patient with a therapeutic protein by the delivery of human cells which have been treated in vitro to insert a DNA segment encoding a therapeutic protein. Additional methods and materials for the practice of gene therapy techniques are described in U.S. Pat. Nos. 5,631,236 (involving adenoviral vectors), 5,672,510 (involving retroviral vectors), 5,635,399 (involving retroviral vectors expressing cytokines).

Nonviral delivery methods include, but are not limited to, liposome-mediated transfer, naked DNA delivery (direct injection), receptor-mediated transfer (ligand-DNA complex), electroporation, calcium phosphate precipitation, and microparticle bombardment (e.g., gene gun). Gene therapy materials and methods may also include inducible promoters, tissue-specific enhancer-promoters, DNA sequences designed for site-specific integration, DNA sequences capable of providing a selective advantage over the parent cell, labels to identify transformed cells, negative selection systems and expression control systems (safety measures), cell-specific binding agents (for cell targeting), cell-specific internalization factors, and transcription factors to enhance expression by a vector as well as methods of vector manufacture. Such additional methods and materials for the practice of gene therapy techniques are described in U.S. Pat. No. 4,970,154 (involving electroporation techniques), U.S. Pat. No 5,679,559 (describing a lipoprotein-containing system for gene delivery), U.S. Pat. No. 5,676,954 (involving liposome carriers), U.S. Pat. No. 5,593,875 (describing methods for calcium phosphate transfection), and U.S. Pat. No. 4,945,050 (describing a process wherein biologically active particles are propelled at cells at a speed whereby the particles penetrate the surface of the cells and become incorporated into the interior of the cells), and PCT Pub. No. WO 96/40958 (involving nuclear ligands).

It is also contemplated that Secs-1 gene therapy or cell therapy can further include the delivery of one or more additional polypeptide(s) in the same or a different cell(s). Such cells may be separately introduced into the patient, or the cells may be contained in a single implantable device, such as the encapsulating membrane described above, or the cells may be separately modified by means of viral vectors.

A means to increase endogenous Secs-1 polypeptide expression in a cell via gene therapy is to insert one or more enhancer elements into the Secs-1 polypeptide promoter, where the enhancer elements can serve to increase transcriptional activity of the Secs-1 gene. The enhancer elements used will be selected based on the tissue in which one desires to activate the gene—enhancer elements known to confer promoter activation in that tissue will be selected. For example, if a gene encoding a Secs-1 polypeptide is to be "turned on" in T-cells, the lck promoter enhancer element may be used. Here, the functional portion of the transcriptional element to be added may be inserted into a fragment of DNA containing the Secs-1 polypeptide promoter (and optionally, inserted into a vector and/or 5' and/or 3' flanking sequences) using standard cloning techniques. This construct, known as a "homologous recombination construct," can then be introduced into the desired cells either ex vivo or in vivo.

Gene therapy also can be used to decrease Secs-1 polypeptide expression by modifying the nucleotide sequence of the endogenous promoter. Such modification is typically accomplished via homologous recombination methods. For example, a DNA molecule containing all or a portion of the promoter of the Secs-1 gene selected for inactivation can be engineered to remove and/or replace pieces of the promoter that regulate transcription. For example, the TATA box and/or the binding site of a transcriptional activator of the promoter may be deleted using standard molecular biology techniques; such deletion can inhibit promoter activity thereby repressing the transcription of the corresponding Secs-1 gene. The deletion of the TATA box or the transcription activator binding site in the promoter may be accomplished by generating a DNA construct comprising all or the relevant portion of the Secs-1 polypeptide promoter (from the same or a related species as the Secs-1 gene to be regulated) in which one or more of the TATA box and/or transcriptional activator binding site nucleotides are mutated via substitution, deletion and/or insertion of one or more nucleotides. As a result, the TATA box and/or activator binding site has decreased activity or is rendered completely inactive. This construct, which also will typically contain at least about 500 bases of DNA that correspond to the native (endogenous) 5' and 3' DNA sequences adjacent to the promoter segment that has been modified, may be introduced into the appropriate cells (either ex vivo or in vivo) either directly or via a viral vector as described herein. Typically, the integration of the construct into the genomic DNA of the cells will be via homologous recombination, where the 5' and 3' DNA sequences in the promoter construct can serve to help integrate the modified promoter region via hybridization to the endogenous chromosomal DNA.

Uses of Secs-1 Nucleic Acids and Polypeptides

Nucleic acid molecules of the invention (including those that do not themselves encode biologically active polypeptides) may be used to map the locations of the Secs-1 gene and related genes on chromosomes. Mapping may be done by techniques known in the art, such as PCR amplification and in situ hybridization.

Secs-1 nucleic acid molecules (including those that do not themselves encode biologically active polypeptides), may be useful as hybridization probes in diagnostic assays to test, either qualitatively or quantitatively, for the presence of a Secs-1 nucleic acid molecule in mammalian tissue or bodily fluid samples.

Secs-1 polypeptides may be used (simultaneously or sequentially) in combination with one or more cytokines, growth factors, antibiotics, anti-inflammatories, and/or chemotherapeutic agents as is appropriate for the condition being treated.

Other methods may also be employed where it is desirable to inhibit the activity of one or more Secs-1 polypeptides. Such inhibition may be effected by nucleic acid molecules that are complementary to and hybridize to expression control sequences (triple helix formation) or to Secs-1 mRNA. For example, antisense DNA or RNA molecules, which have a sequence that is complementary to at least a portion of a Secs-1 gene. can be introduced into the cell. Anti-sense probes may be designed by available techniques using the sequence of the Secs-1 gene disclosed herein. Typically, each such antisense molecule will be complementary to the start site (5' end) of each selected Secs-1 gene. When the antisense molecule then hybridizes to the corresponding Secs-1 mRNA, translation of this mRNA is prevented or reduced. Anti-sense inhibitors provide information relating to the decrease or absence of a Secs-1 polypeptide in a cell or organism.

Alternatively, gene therapy may be employed to create a dominant-negative inhibitor of one or more Secs-1 polypeptides. In this situation, the DNA encoding a mutant polypeptide of each selected Secs-1 polypeptide can be prepared and introduced into the cells of a patient using either viral or non-viral methods as described herein. Each such mutant is typically designed to compete with endogenous polypeptide in its biological role.

In addition, a Secs-1 polypeptide, whether biologically active or not, may be used as an immunogen, that is, the polypeptide contains at least one epitope to which antibodies may be raised. Selective binding agents that bind to a Secs-1 polypeptide (as described herein) may be used for in vivo and in vitro diagnostic purposes, including, but not limited to, use in labeled form to detect the presence of Secs-1 polypeptide in a body fluid or cell sample. The antibodies may also be used to prevent, treat, or diagnose a number of diseases and disorders, including those recited herein. The antibodies may bind to a Secs-1 polypeptide so as to diminish or block at least one activity characteristic of a Secs-1 polypeptide, or may bind to a polypeptide to increase at least one activity characteristic of a Secs-1 polypeptide (including by increasing the pharmacokinetics of the Secs-1 polypeptide).

Deposits of cDNA encoding murine Secs1 polypeptide and human Secs1 polypeptide, subcloned into pSPORT1 (GIBCO-BRL) and p7T73D (Pharmacia AB Corp.), and having Accession Nos. PTA-1753 and PTA-1755, were made with the American Type Culture Collection, 10801 University Boulevard, Manassas, Va. 20110-2209 on Apr. 25, 2000.

The following examples are intended for illustration purposes only, and should not be construed as limiting the scope of the invention in any way.

EXAMPLE 1

Cloning of the Human and Murine Secs-1 Polypeptide Genes

Generally, materials and methods as described in Sambrook et al. supra were used to clone and analyze the genes encoding human and murine Secs-1 polypeptides.

Using a proteomic-based approach, a novel peptide was identified from conditioned media obtained from squamous cell and colorectal carcinoma cell lines. The approach utilized in identifying this peptide suggests that it is a naturally secreted product. The amino acid sequence of the identified peptide was determined and found to share sequence identity with EST sequences present in both GenBank® and proprietary (Amgen dbEST) databases. Specifically, the amino acid sequence of this novel secreted peptide was found to share homology with an amino acid sequence corresponding to a human EST sequence present in the GenBank® database (accession no. AA283751). The cDNA clone corresponding to this EST sequence was obtained from the Integrated Molecular Analysis of Genomes and their Expression (I.M.A.G.E.) Consortium (I.M.A.G.E. Consortium clone no. 713624). The nucleotide sequence of this cDNA clone was determined and was found to contain the complete coding sequence for the human Secs-1 gene.

Sequence analysis of the full-length cDNA for human Secs-1 polypeptide indicated that the gene comprises a 243 bp open reading frame encoding a protein of 81 amino acids and possessing a potential signal peptide of 24 amino acids in length at its amino terminus (FIG. 2; predicted signal peptide indicated by underline). FIG. 2 illustrates the nucleotide sequence of the human Secs-1 nucleic acid sequence and the deduced amino acid sequence of the human Secs-1 polypeptide. The human Secs-1 polypeptide was found to be glycosylated at position 51 (Asp).

Sequences corresponding to the murine Secs-1 gene were identified in proprietary databases derived from AC-6 stromal and colon crypt cDNA libraries. Murine Secs-1 polypeptide cDNA sequences were isolated as follows. Total RNA was prepared from either the AC-6 stromal cell line or colon crypt tissue using the TRizol® method (GIBCO-BRL, Rockville, Md.), mRNA isolated from total RNA using a Dynabeads® mRNA kit (Dynal, Inc., Lake Success, N.Y.), and cDNA synthesized from the isolated mRNA using the SuperScript® System (GIBCO-BRL) and a Not I oligo d(T) primer (GIBCO-BRL). Following cDNA synthesis, Sal I adapters (GIBCO-BRL) were ligated onto the cDNA, the cDNA was digested with Not I, and the digested cDNA was then size selected on an agarose gel. Inserts of approximately 1.0 kb or more in size were isolated and ligated into the pSPORT (GIBCO-BRL) vector. Ligation products were transformed into DH10B competent cells and the nucleotide sequence of selected clones was then analyzed.

Sequence analysis of the full-length cDNA for murine Secs-1 polypeptide indicated that the gene comprises a 234 bp open reading frame encoding a protein of 78 amino acids and possessing a potential signal peptide of 24 amino acids in length at its amino terminus (FIG. 1; predicted signal peptide indicated by underline). FIG. 1 illustrates the nucleotide sequence of the murine Secs-1 nucleic acid sequence and the deduced amino acid sequence of the murine Secs-1 polypeptide.

In addition to identifying a number of homologous sequences in GenBank® and proprietary databases, the human and murine Secs-1 nucleic acid sequences were found to share sequence homology with a previously reported rat EST sequence (Hennigan et at., 1994, *Ocogene* 9:3591-600). However, Hennigan et at. disclosed only a portion of the rat Secs-1 nucleic acid sequence and did not disclose the open reading frame for the rat Secs-1 ortholog. FIG. 3 illustrates the amino acid sequence alignment of the full-length rat Secs-1 polypeptide, murine Secs-1 polypeptide, and human Secs-1 polypeptide. A FASTA search of the SWISS-PROT-database using the predicted amino acid sequences for both human and murine Secs-1 polypeptide failed to identify any other sequences sharing significant homology.

FIGS. 4A-4F illustrates the genomic nucleotide sequence for human Secs-1 polypeptide. The genomic sequence for human Secs-1 polypeptide was determined by analysis of a publicly available BAC clone (GenBank® accession no. AC022389). The location and deduced amino acid sequence of the exons are indicated (FIGS. 4A, 4D, and 4F).

EXAMPLE 2

Secs-1 mRNA Expression

Multiple human tissue northern blots (either proprietary or obtained from BioSource Technologies, Inc., Hayward, Calif. or Clontech Laboratories, Inc., Palo Alto, Calif.) were probed with a $^{32}$P-dCTP labeled, 542 bp human Secs1 PCR fragment. The human Secs1 PCR probe was prepared using 25 ng of Jurkat cell cDNA, amplimers corresponding to the human Secs-1 gene (5'-C-C-C-A-A-C-T-C-A-A-C-A-A-A-C-C-T-G-A-A-A-3'; SEQ ID NO: 14 and 5'-G-G-G-A-C-C-A-C-T-G-G-A-T-G-C-T-G-3'; SEQ ID NO: 15) at a final concentration of 0.2 µM each, 2.5 units of 32 Taq polymerase, 200 µM dNTPs, 50 µCi $^{32}$P-dCTP, and 1× Taq polymerase buffer, in a total reaction volume of 25 µl. Reactions were performed at 94° C. for 2 minutes for one cycle; 94° C. for 20 seconds, 57.8° C. for 30 seconds, and 72° C. for 1 minute for 40 cycles; and 72° C. for 5 minutes for 1 cycle.

Northern blots were prehybridized for 1 hour at 42° C. in ULTRAhyb® (Ambion, Inc., Austin, Tex.), and then were hybridized at 42° C. overnight in fresh hybridization buffer containing approximately 8×10$^4$ cpmµl of the labeled probe. Following hybridization, the filters were washed twice for 30 minutes at 50° C. in 2× SSPE and 0.5% SDS, and then twice for 15 minutes at room temperature in 0.1× SSPE and 0.5% SDS. The blots were then analyzed using a phosphoimager.

Analysis of the Northern blots indicated that a single transcript having a molecular mass of 1 kb was expressed in colon and prostate tissue. The expression of Secs-1 mRNA in normal colon was found to be four fold higher than that in colon tumor, and the expression of Secs-1 mRNA in normal prostate tissue was found to be higher than that in prostate tumor.

The expression of Secs-1 mRNA was localized by in situ hybridization. A panel of normal embryonic and adult mouse tissues was fixed in 4% paraformaldehyde, embedded in paraffin, and sectioned at 5 µm. Sectioned tissues were permeabilized in 0.2 M HCl, digested with Proteinase K, and acetylated with triethanolamine and acetic anhydride. Sections were prehybridized for 1 hour at 60° C. in 300 mM NaCl, 20 mM Tris-HCl, pH 8.0, 5 mM EDTA, 1× Denhardt's solution, 0.2% SDS, 10 mM DTT, 0.25 mg/ml tRNA, 25 µg/ml polyA, 25 µg/ml polyC and 50% formamide and then hybridized overnight at 60° C. in the same buffer containing 10% dextran and 2×10⁴ cpm/μl of a $^{33}$P-labeled, 291 bp antisense riboprobe complementary to the murine Secs-1 gene.

The riboprobe was obtained by in vitro transcription of a clone containing murine Secs-1 cDNA sequences. A murine Secs-1 cDNA sequence was generated by RT-PCR using 100 μg of total RNA from MSC 2.2.2 cells, amplimers corresponding to the murine Secs-1 gene (5'-A-C-T-C-C-G-G-C-T-C-C-T-T-C-A-C-T-A-T-G-A-3'; SEQ ID NO: 16 and 5'-A-T-G-T-G-G-G-C-A-T-C-A-T-C-A-A-C-G-C-T-T-T-A-3'; SEQ ID NO: 17) at a final concentration of 0.2 μM each, 5 units of Taq polymerase, 200 μM dNTPs, and 1× Taq polymerase buffer, in a total reaction volume of 50 μl. Reactions were performed at 94° C. for 2 minutes for one cycle; 94° C. for 20 seconds and 57° C. for 30 seconds for 40 cycles; and 72° C. for 5 minutes for 1 cycle. Following amplification, PCR products were separated on an agarose gel, excised from the gel, purified using the QIAQuick® Gel Extraction kit (QIAGEN Inc., Valencia, Calif.), and ligated into the pGEM-T (Promega Corp., Madison, Wis.) vector. Ligation products were transformed into DH5-α competent cells and six clones selected for analysis by restriction enzyme digestion and sequencing.

Following hybridization, sections were rinsed in buffer, treated with RNaseA to digest unhybridized probe, and then washed in 0.1× SSC at 55° C. for 30 minutes. Sections were then immersed in NTB-2 emulsion (Eastman Kodak Co., Rochester, N.Y.), exposed for 3 weeks at 4° C., developed, and counterstained with hematoxylin and eosin. Tissue morphology and hybridization signal were simultaneously analyzed by darkfield and standard illumination for brain (one sagittal and two coronal sections), gastrointestinal tract (esophagus, stomach, duodenum, jejunum, ileum, proximal colon, and distal colon), pituitary, liver, lung, heart, spleen, thymus, lymph nodes, kidney, adrenal, bladder, pancreas, salivary gland, male and female reproductive organs (ovary, oviduct, and uterus in the female; and testis, epididymis, prostate, seminal vesicle, and vas deferens in the male), BAT and WAT (subcutaneous, peri-renal), bone (femur), skin, breast, and skeletal muscle.

The Secs-1 probe produced a clear signal with little background. In both the embryonic and adult tissue, the strongest signal was detected in the epithelial cells of the gastrointestinal system. In adult tissues, intense labeling was specifically found in the epithelial cells of the cheek, ventral tongue, esophagus, and large intestine. A moderate signal was observed in the distal ileum, and no expression was detected in the stomach or proximal sections of the small intestine. While a moderate level of expression was detected in the epithelial cells of embryonic gut, a strong signal was observed in the developing salivary glands.

In tissues from other than the gastrointestinal system, a moderate to strong signal was detected in the developing spermatids of the seminiferous tubules of the testis, some portions of the uterus, and in the epithelial cells of the nipple. A moderate level of expression was detected in the epithelial cells of the skin and nasal cavity. Lower levels of expression were also found in the lymph node, spleen, thymus, and humerus and ulna of the forelimb.

EXAMPLE 3

Production of Secs-1 Polypeptides

To prepare a human Secs-1 bacterial expression vector, a human Secs-1 cDNA sequence was first prepared by PCR amplification of 1 μμg of a human Secs-1 cDNA clone in a reaction mix containing 0.4 pm/μl of amplimers corresponding to the human Secs-1 gene (5'-A-A-A-T-A-A-C-A-T-A-T-G-A-A-A-C-G-T-C-G-T-C-C-A-G-C-T-A-A-A-G-C-C-T-G-G-T-C-A-G-G-C-3'; SEQ ID NO: 18 and 5'-G-G-T-G-A-T-G-G-T-G-A-T-G-G-T-G-C-A-C-C-T-G-T-G-G-G-A-G-T-G-C-C-C-C-3'; SEQ ID NO: 19) and two Ready-To-Go® PCR Beads (Amersham Pharmacia Biotech AB Corp., Piscataway, N.J.), in a total reaction volume of 50 μl. Reactions were performed at 94° C. for 2 minutes for one cycle; 94° C. for 45 seconds, 55° C. for 45 seconds, and 72° C. for 45 seconds for 30 cycles. The PCR product generated in this reaction was gel-purified on a 200 agarose gel.

The human Secs-1 PCR product produced in the initial amplification reaction was then re-amplified in a reaction mix containing 0.4 pm/μl of amplimers corresponding to the human Secs-1 gene (5'-A-A-A-T-A-A-C-A-T-A-T-G-A-A-A-C-G-T-C-G-T-C-C-A-G-C-T-A-A-A-G-C-C-T-G-G-T-C-A-G-G-C-3'; SEQ ID NO: 18 and 5'-G-T-G-G-T-A-G-T-G-G-T-A-G-T-G-G-T-A-G-T-A-A-C-T-A-T-C-C-T-A-G-G-T-A-T-T-T-3'; SEQ ID NO: 20) and two Ready-To-Go® PCR Beads, in a total reaction volume of 50 μl. Reactions were performed at 94° C. for 2 minutes for one cycle; 94° C. for 45 seconds, 55° C. for 45 seconds, and 72° C. for 45 seconds for 30 cycles. The amplimers used in the re-amplification reaction were designed to incorporate suitable restriction sites into the human Secs-1 cDNA sequence.

The pAMG21 (ATCC No. 98113) vector, which contains a lux promoter and kanamycin resistance gene, and the PCR products from the second amplification reaction were digested with Bam HI and Nde I. The PCR products were then gel purified and ligated into pAMG21. Ligation products were transformed into GM121 (ATCC No. 202174) competent cells by electroporation and transformants selected for kanamycin resistance. Plasmid DNA isolated from selected colonies was then subjected to sequence analysis.

Transformed host cells were incubated in 2XYT medium containing 40 μg/ml kanamycin at 30° C. prior to induction. Gene expression was induced by the addition of N-(3-oxohexanoyl)-dl-homoserine lactone to a final concentration of 100 ng/ml followed by incubation at 30° C. for four hours. The expression of human Secs-1 polypeptide was evaluated by centrifuging the culture, resuspending and lysing the bacterial pellets, and then analyzing the host cell proteins by SDS-polyacrylamide gel electrophoresis.

EXAMPLE 4

Production of Anti-Secs-1 Polypeptide Antibodies

Antibodies to Secs-1 polypeptides were generated using procedures as described in Hudson and Bay, *Practical Immunology* (2nd ed., Blackwell Scientific Publications). Specifically, rabbits were immunized with a chemically synthesized Secs-1 peptide (C-W-V-V-P-G-A-L-P-Q-I; SEQ ID NO: 21). Prior to immunization, the Secs-1 peptide sequence was coupled to K-L-H using Maleimide Conjugation Buffer (Pierce Chemical, Rockford, Ill.) according to the manufacturer's suggested protocols. Rabbits were injected with the Secs-1 peptide and those animals having sufficient serum titer levels as determined by enzyme-linked immunosorbent assays (ELISA) were then selected for polyclonal antibody production.

EXAMPLE 5

Expression of Murine Secs-1 Polypeptide in Transgenic Mice

To assess the biological activity of murine Secs-1 polypeptide, a construct encoding a Secs-1 polypeptide/Fc fusion protein under the control of a liver specific ApoE promoter is prepared. The Secs-1 polypeptide/Fc fusion construct comprises the N-terminal 367 amino acids of Secs-1 polypeptide fused to the Fc portion of human IgG. The delivery of this construct is expected to cause pathological changes that are informative as to the function of Secs-1 polypeptide. Similarly, a construct containing the full-length Secs-1 polypeptide under the control of the beta actin promoter is prepared. The delivery of this construct is expected to result in ubiquitous expression.

To generate this construct, PCR is used to amplify template DNA sequences encoding murine Secs-1 polypeptide using primers that correspond to the 5' and 3' ends of the desired sequence and which incorporate restriction enzyme sites to permit insertion of the amplified product into an expression vector. Following amplification, PCR products are gel purified, digested with the appropriate restriction enzymes, and ligated into an expression vector using standard recombinant DNA techniques. For example, amplified Secs-1 polypeptide sequences can be cloned into an expression vector under the control of the human β-actin promoter as described by Graham et al., 1997, *Nature Genetics*, 17:272-74 and Ray et al., 1991, *Genes Dev.* 5:2265-73.

Following ligation, reaction mixtures are used to transform an *E. coli* host strain by electroporation and transformants are selected for drug resistance. Plasmid DNA from selected colonies is isolated and subjected to DNA sequencing to confirm the presence of an appropriate insert and absence of mutation. The murine Secs-1 polypeptide expression is purified through two rounds of CsCl density gradient centrifugation, cleaved with a suitable restriction enzyme, and the linearized fragment containing the murine Secs-1 polypeptide transgene is purified by gel electrophoresis. The purified fragment is resuspended in 5 mM Tris, pH 7.4, and 0.2 mM EDTA at a concentration of 2 mg/mL. Single-cell embryos from BDF1×BDF1 bred mice are injected as described (PCT Pub. No. WO 97/23614). Embryos are cultured overnight in a $CO_2$ incubator and 15-20 two-cell embryos are transferred to the oviducts of a pseudopregnant CD1 female mice. Offspring obtained from the implantation of microinjected embryos are screened by PCR amplification of the integrated transgene in genomic DNA samples as follows. Ear pieces are digested in 20 mL ear buffer (20 mM Tris, pH 8.0, 10 mM EDTA, 0.5% SDS, and 500 mg/mL proteinase K) at 55° C. overnight. The sample is then diluted with 200 mL of TE, and 2 mL of the ear sample is used in a PCR reaction using appropriate primers.

At 8 weeks of age, transgenic founder animals and control animals are sacrificed for necropsy and pathological analysis. Portions of spleen are removed and total cellular RNA isolated from the spleens using the Total RNA Extraction Kit (QIAGEN Inc.) and transgene expression determined by RT-PCR. RNA recovered from spleens is converted to cDNA using the SuperScript® Preamplification System (GIBCO-BRL) as follows. A suitable primer, located in the expression vector sequence and 3' to the Secs-1 polypeptide transgene, is used to prime cDNA synthesis from the transgene transcripts. Ten mg of total spleen RNA from transgenic founders and controls is incubated with 1 mM of primer for 10 minutes at 70° C. and placed on ice. The reaction is then supplemented with 10 mM Tris-HCl, pH 8.3, 50 mM KCl, 2.5 mM $MgCl_2$, 10 mM of each dNTP, 0.1 mM DTT, and 200 U of Super-Script® II reverse transcriptase. Following incubation for 50 minutes at 42° C., the reaction is stopped by heating for 15 minutes at 72° C. and digested with 2U of RNase H for 20 minutes at 37° C. Samples are then amplified by PCR using primers specific for Secs-1 polypeptide.

EXAMPLE 6

Biological Activity of Murine Secs-1 Polypeptide in Transgenic Mice

Prior to euthanasia, transgenic animals are weighed, anesthetized by isofluorane and blood drawn by cardiac puncture. The samples are subjected to hematology and serum chemistry analysis. Radiography is performed after terminal exsanguination. Upon gross dissection, major visceral organs are subject to weight analysis.

Following gross dissection, tissues (i.e., liver, spleen, pancreas, stomach, the entire gastrointestinal tract, kidney, reproductive organs, skin and mammary glands, bone, brain, heart, lung, thymus, trachea, esophagus, thyroid, adrenals, urinary bladder, lymph nodes and skeletal muscle) are removed and fixed in 10% buffered Zn-Formalin for histological examination. After fixation, the tissues are processed into paraffin blocks, and 3 mm sections are obtained. All sections are stained with hematoxylin and exosin, and are then subjected to histological analysis.

The spleen, lymph node, and Peyer's patches of both the transgenic and the control mice are subjected to immunohistology analysis with B cell and T cell specific antibodies as follows. The formalin fixed paraffin embedded sections are deparaffinized and hydrated in deionized water. The sections are quenched with 300 hydrogen peroxide, blocked with Protein Block (Lipshaw Co., Pittsburgh, Pa.), and incubated in rat monoclonal anti-mouse B220 and CD3 (Harlan Bioproducts, Indianapolis, Ind.). Antibody binding is detected by biotinylated rabbit anti-rat immunoglobulins and peroxidase conjugated streptavidin (BioGenex Laboratories Corp., San Ramon, Calif.) with DAB as a chromagen (BioTek Solutions, Inc., Santa Barbara, Calif.). Sections are counterstained with hematoxylin.

After necropsy, MLN and sections of spleen and thymus from transgenic animals and control littermates are removed. Single cell suspensions are prepared by gently grinding the tissues with the flat end of a syringe against the bottom of a 100 mm nylon cell strainer (Becton, Dickinson and Co., Franklin Lakes, N.J.). Cells are washed twice, counted, and approximately $1\times10^6$ cells from each tissue are then incubated for 10 minutes with 0.5 μg CD16/32(FcγIII/II) Fc block in a 20 μL volume. Samples are then stained for 30 minutes at 2-8° C. in a 100 μL volume of PBS (lacking $Ca^+$ and $Mg^+$), 0.1% bovine serum albumin, and 0.01% sodium azide with 0.5 μg antibody of FITC or PE-conjugated monoclonal antibodies against CD90.2 (Thy-1.2), CD45R (B220), CD 11 b(Mac-1), Gr-1, CD4, or CD8 (PharMingen Corp., San Diego, Calif.). Following antibody binding, the cells are washed and then analyzed by flow cytometry on a FACScan (Becton, Dickinson and Co.).

EXAMPLE 7

Biological Activity of Murine Secs-1 Polypeptide

The Secs-1 polypeptide/Fc fusion construct prepared in Example 6 is used to analyze the direct binding of Secs-1 polypeptide to members of the FGF family of growth factors.

The expression of Secs-1 polypeptide in bone marrow stromal cell lines has been shown to correlate with the ability of stromal cells to maintain hematopoietic stem cells. If the ability of stromal cells to maintain hematopoietic stem cells is due to the expression of Secs-1 polypeptide, rather than being merely correlative, the expression of Secs-1 polypeptide in a non-supportive stromal cell line will convert that cell line into a supportive one. Similarly, if the expression of Secs-1 polypeptide in ST2 cells causes these cells to support osteoclastogenesis in the absence of dexamethasone and vitamin D3, this result would suggest that the strong induction of Secs-1 polypeptide expression by dexamethasone and vitamin D3 is not merely an innocent bystander effect but is causally involved in the appearance of the osteoclast support phenotype.

While the present invention has been described. in terms of the preferred embodiments, it is understood that variations and modifications will occur to those skilled in the art. Therefore, it is intended that the appended claims cover all such equivalent variations that come within the scope of the invention as claimed.

What is claimed is:

1. An isolated nucleic acid molecule comprising:
   (a) the nucleotide sequence as set forth in SEQ ID NO: 4;
   (b) a nucleotide sequence encoding a polypeptide comprising the amino acid sequence of SEQ ID NO: 5; or
   (c) a nucleotide sequence that is fully complementary to the entirety of the nucleotide sequence of SEQ ID NO: 4.

2. An isolated nucleic acid molecule consisting of:
   (a) a region of a nucleic acid molecule comprising the nucleotide sequence of SEQ ID NO: 4 encoding a polypeptide fragment of at least about 25 amino acid residues, but not more than 80 amino acid residues of the amino acid sequence of SEQ ID NO: 5; or
   (b) a nucleotide sequence encoding a polypeptide fragment of at least about 25 amino acid residues, but not more than 80 amino acid residues of the amino acid sequence of SEQ ID NO: 5.

3. An isolated nucleic acid molecule comprising:
   (a) a nucleotide sequence encoding a polypeptide comprising the amino acid sequence of SEQ ID NO: 5; or
   (b) a nucleotide sequence that is fully complementary to the entirety of a nucleotide sequence encoding a polypeptide comprising the amino acid sequence of SEQ ID NO: 5.

4. A vector comprising the nucleic acid molecule of claims 1, 2, or 3.

5. An isolated host cell comprising the vector of claim 4.

6. The isolated host cell of claim 5 that is a eukaryotic cell.

7. The isolated host cell of claim 5 that is a prokaryotic cell.

8. A process of producing a polypeptide comprising the amino acid sequence of SEQ ID NO: 5, comprising the step of culturing an isolated host cell having a vector comprising a nucleic acid molecule encoding said polypeptide under suitable conditions to express the polypeptide encoded by said nucleic acid molecule, and optionally isolating the polypeptide from the culture, thereby producing the polypeptide.

* * * * *

```
                              SEQUENCE LISTING

<160> NUMBER OF SEQ ID NOS: 22

<210> SEQ ID NO 1
        <211> LENGTH: 744
        <212> TYPE: DNA
        <213> ORGANISM: Mus musculus
        <220> FEATURE:
        <221> NAME/KEY: CDS
        <222> LOCATION: (38)..(274)

<400> SEQUENCE: 1
gcttcctccc taggcgtgag actccggctc cttcact atg aga ctt cta gcc ctt      55
                                                Met Arg Leu Leu Ala Leu
                                                  1               5 tcc ggt ctg ctc tgc atg ctg ctc ctc tgt ttc tgc att ttc tcc tca      103
        Ser Gly Leu Leu Cys Met Leu Leu Leu Cys Phe Cys Ile Phe Ser Ser
                     10                  15                  20 gaa ggg aga aga cat cct gcc aag tcc ttg aaa ctc agg cgc tgc tgt      151
        Glu Gly Arg Arg His Pro Ala Lys Ser Leu Lys Leu Arg Arg Cys Cys
                 25                  30                  35 cac cta tct cct aga tcc aag ctg aca acc tgg aaa gga aac cac aca      199
        His Leu Ser Pro Arg Ser Lys Leu Thr Thr Trp Lys Gly Asn His Thr
             40                  45                  50 agg ccc tgc aga ctc tgc aga aac aag cta cca gtc aag tca tgg gtg      247
        Arg Pro Cys Arg Leu Cys Arg Asn Lys Leu Pro Val Lys Ser Trp Val
         55                  60                  65                  70 gtg cct ggg gct ctc cca cag ata tag ggcctcctcc gcccagatga              294
        Val Pro Gly Ala Leu Pro Gln Ile
                         75 agcgttgatg cccagatgtg gagacaccag aagcatacac actatgttgc cttgccctt      354 gccaatgagc tgtgacactg gaatgcttca cttcagacat cagggcggat ggattgcaga     414 attccaagtc ctcattccaa aggtgtcacc aaccttcaga gtcactaagg tccaggctca     474 gcccacaagt caccatggct cctccagagt aaaagtccaa gattccacct gtgggagcta     534 cagatccaga gactttcaag ctgactagag tgcagagaag caagacctca gtgtgatcag     594 ccgagactac agcatcttgg gaaccctcag tcagccccaa acccctaaca cttaaccact     654 ggtctccaaa ccaacacctg taacttccta atgaaatcat caggaggata ccaaaagaaa     714 taaaccataa atcagcatac acactaaaaa                                     744

<210> SEQ ID NO 2
        <211> LENGTH: 78
```

```
<212> TYPE: PRT
<213> ORGANISM: Mus musculus

<400> SEQUENCE: 2

Met Arg Leu Leu Ala Leu Ser Gly Leu Leu Cys Met Leu Leu Leu Cys
 1               5                  10                  15

Phe Cys Ile Phe Ser Ser Glu Gly Arg Arg His Pro Ala Lys Ser Leu
             20                  25                  30

Lys Leu Arg Arg Cys Cys His Leu Ser Pro Arg Ser Lys Leu Thr Thr
         35                  40                  45

Trp Lys Gly Asn His Thr Arg Pro Cys Arg Leu Cys Arg Asn Lys Leu
 50                  55                  60

Pro Val Lys Ser Trp Val Val Pro Gly Ala Leu Pro Gln Ile
 65                  70                  75

<210> SEQ ID NO 3
<211> LENGTH: 54
<212> TYPE: PRT
<213> ORGANISM: Mus musculus

<400> SEQUENCE: 3

Arg Arg His Pro Ala Lys Ser Leu Lys Leu Arg Arg Cys Cys His Leu
 1               5                  10                  15

Ser Pro Arg Ser Lys Leu Thr Thr Trp Lys Gly Asn His Thr Arg Pro
             20                  25                  30

Cys Arg Leu Cys Arg Asn Lys Leu Pro Val Lys Ser Trp Val Val Pro
         35                  40                  45

Gly Ala Leu Pro Gln Ile
     50

<210> SEQ ID NO 4
<211> LENGTH: 806
<212> TYPE: DNA
<213> ORGANISM: Homo sapiens
<220> FEATURE:
<221> NAME/KEY: CDS
<222> LOCATION: (29)..(274)

<400> SEQUENCE: 4
ggaacgaggg aaaatctgcc ttctcacc atg agg ctt cta gtc ctt tcc agc        52
                                Met Arg Leu Leu Val Leu Ser Ser
                                 1               5 ctg ctc tgt atc ctg ctt ctc tgc ttc tcc atc ttc tcc aca gaa ggg      100
Leu Leu Cys Ile Leu Leu Leu Cys Phe Ser Ile Phe Ser Thr Glu Gly
         10                  15                  20 aag aga cgt cct gcc aag gcc tgg tca ggc agg aga acc agg ctc tgc      148
Lys Arg Arg Pro Ala Lys Ala Trp Ser Gly Arg Arg Thr Arg Leu Cys
 25                  30                  35                  40 tgc cac cga gtc cct agc ccc aac tca aca aac ctg aaa gga cat cat      196
Cys His Arg Val Pro Ser Pro Asn Ser Thr Asn Leu Lys Gly His His
                 45                  50                  55 gtg agg ctc tgt aaa cca tgc aag ctt gag cca gag ccc cgc ctt tgg      244
Val Arg Leu Cys Lys Pro Cys Lys Leu Glu Pro Glu Pro Arg Leu Trp
             60                  65                  70 gtg gtg cct ggg gca ctc cca cag gtg tag cactcccaaa gcaagactcc        294
Val Val Pro Gly Ala Leu Pro Gln Val
 75                  80 agacagcgga gaacctcatg cctggcacct gaggtaccca gcagcctcct gtctcccctt    354
tcagccttca cagcagtgag ctgcaatgtt ggagggcttc atctcgggct gcaaggaccc    414
```
tgggaaagtt ccagaactcc acgtccttgt ctcaattgtg ccatcaactt tcagagctat    474
catgagccaa cctcacccca cagggcctca gtcgccacca tgtgggcctc tccagtgcaa    534
accaccgagc attccaccat gaccggtcac agctacaaat ccagagacca tcaatcctgc    594
tagagtgcag ggtggcaagc acccaagggt ggctgaccaa gactgcagag tctcctccat    654
cttcaggtcc attcagcctc ctggcattta actaccagca tccagtggtc cccaaggaat    714
cccttcctag cctcctgaca tgagtctgct ggaaagagca tccaaacaaa caagtaataa    774
ataaataaat aaactcaatg cagacacaaa aa    806

<210> SEQ ID NO 5
<211> LENGTH: 81
<212> TYPE: PRT
<213> ORGANISM: Homo sapiens

<400> SEQUENCE: 5

Met Arg Leu Leu Val Leu Ser Ser Leu Leu Cys Ile Leu Leu Leu Cys
  1               5                   10                  15

Phe Ser Ile Phe Ser Thr Glu Gly Lys Arg Arg Pro Ala Lys Ala Trp
             20                  25                  30

Ser Gly Arg Arg Thr Arg Leu Cys Cys His Arg Val Pro Ser Pro Asn
         35                  40                  45

Ser Thr Asn Leu Lys Gly His His Val Arg Leu Cys Lys Pro Cys Lys
     50                  55                  60

Leu Glu Pro Glu Pro Arg Leu Trp Val Val Pro Gly Ala Leu Pro Gln
 65                  70                  75                  80

Val

<210> SEQ ID NO 6
<211> LENGTH: 57
<212> TYPE: PRT
<213> ORGANISM: Homo sapiens

<400> SEQUENCE: 6

Lys Arg Arg Pro Ala Lys Ala Trp Ser Gly Arg Arg Thr Arg Leu Cys
  1               5                   10                  15

Cys His Arg Val Pro Ser Pro Asn Ser Thr Asn Leu Lys Gly His His
             20                  25                  30

Val Arg Leu Cys Lys Pro Cys Lys Leu Glu Pro Glu Pro Arg Leu Trp
         35                  40                  45

Val Val Pro Gly Ala Leu Pro Gln Val
     50                  55

<210> SEQ ID NO 7
<211> LENGTH: 77
<212> TYPE: PRT
<213> ORGANISM: Rattus norvegicus

<400> SEQUENCE: 7

Met Arg Leu Leu Thr Leu Ser Gly Leu Phe Phe Met Leu Phe Leu Cys
  1               5                   10                  15

Leu Cys Val Leu Ser Ser Glu Gly Arg Lys Arg Pro Ala Lys Phe Pro
             20                  25                  30

Lys Leu Arg Pro Arg Cys His Leu Ser Pro Arg Ser Lys Pro Ile Thr
         35                  40                  45

Trp Lys Gly Asn His Thr Arg Pro Cys Arg Pro Cys Arg Lys Leu Glu
     50                  55                  60

Ser Asn Ser Trp Val Val Pro Gly Ala Leu Pro Gln Ile
65                  70                  75

<210> SEQ ID NO 8
<211> LENGTH: 4159
<212> TYPE: DNA
<213> ORGANISM: Homo sapiens
<220> FEATURE:
<221> NAME/KEY: unsure
<222> LOCATION: (160)..(169)
<220> FEATURE:
<221> NAME/KEY: unsure
<222> LOCATION: (3884)..(3893)
<220> FEATURE:
<221> NAME/KEY: exon
<222> LOCATION: (1)..(69)
<220> FEATURE:
<221> NAME/KEY: exon
<222> LOCATION: (2627)..(2725)
<220> FEATURE:
<221> NAME/KEY: exon
<222> LOCATION: (4079)..(4159)

<400> SEQUENCE: 8

| | |
|---|---:|
| atg agg ctt cta gtc ctt tcc agc ctg ctc tgt atc ctg ctt ctc tgc | 48 |
| ttc tcc atc ttc tcc aca gaa ggtagggcag cccccagggt gcagatccct | 99 |
| gagcaggatt tcagcatctg ggaagactct gatcaggatt tgttggaggg caggccttgg | 159 |
| nnnnnnnnnn cgcgcgtact tccagccccg tggtgaagac gaaagagggc tctttctcct | 219 |
| gaacctatag gtttggggct caggactgcc tgcaggtggc ttgggggttc cattcacagc | 279 |
| ccctgcaccc ccaaatacat acccagccta agtaaagtgg tgtgttcgcc atgcaaacac | 339 |
| acatacaacc tctcagctag attactgtgc ttaagtccta cctatctaga atttctggag | 399 |
| ccattctctt gtacttgtgt catgcttgga acagagtaaa ttagtgttgg gcaaatgaat | 459 |
| acattaatta gtagaccatc taagtctgaa catcccaaaa cctcatgccc agaaaatatc | 519 |
| catgagcagc tgaaatgaag gtgtgtgtgg tagggaggtg gggtatgttt atgcatgttt | 579 |
| agaaggggac accatctttt tacctctata gatatgaata tttagctctc ttgcccttt | 639 |
| ttctttttc tttttttttt ttttttgag atggagtctt gctctgtcac ccaggctgga | 699 |
| gtgcagtggc gctatctcag ctcactgcaa tctccgcctc ctgggttcaa gcaattctct | 759 |
| gcctcagcct cccaagtagc tgagattaca ggtgcccacc accaagccca gctaattttt | 819 |
| gtattttag tacagacagg tttcaccatc ttggccaggc tggtcttgaa ctcctaacct | 879 |
| cgtaatcctc ccacctcggc ctcccaaagt gctgggatta caggcgtgag ccaccatgcc | 939 |
| tggctgcctt tcttgattca gatagctgag tgtttcaatc cattttctc ttgtctaacc | 999 |
| ctctagaaac tgcctacatt tattttttgt tttagtggtt atggttactc aaacttttgg | 1059 |
| gtgggggag ctggagctat agaaatatat aaagagaaga aaaacactca attccatgat | 1119 |
| tcaagagtag ccatgttcaa cattttgttt atttccttgc atgtagaatt tttaaaaatt | 1179 |
| aattgatgta cctatatgtt caaggttata tctttttat ttatcactat atatattgtt | 1239 |
| ataatcaccc aaaatgctta tgattgaaga tattctggaa gcatttacaa cccagtgtca | 1299 |
| gcagcagcca tctctgagta gtgggattat aacaagtgtt tgttttacaa agtttctgcg | 1359 |
| atgaaaatgt cccacatata taataaggaa aacagtgatt agaattcctc ataaacacag | 1419 |
| cccgtgacat gcaatttatc agacctctat ttttggacat gttggaggtt gccagtgata | 1479 |
| ccctagtgac aattaaatga ggatagatac cttcccccat aaagtttcct atccatttag | 1539 |
| gactatctgt agcaaactct tgaagtagca ttaatcaact aatatttttca ggtataactt | 1599 |

-continued

```
gctacaagtg aacgtactat gatgaattta catgcttaga catttagata gttcacaatt      1659
gtgtgctttt cctttttga agcaagatct tgctctcttg cccaggtcgg agtgcagtgg       1719
catgaccacg gctcagtgca ggcttgactt ccagggctca agcaatactc gcacctcagg      1779
ttttccagta gctgggaaaa caggtgcgca ccacaatgcc ctgctaattt ttaaaatttt      1839
ttgcagagac gaggtctctc taagttgccc aggctggtct tgaacttctg gactcaagcc      1899
atcctcccac cttggcctcc cagagtgcta ggatcacagg catgagccac cacacctggc     1959
ctactttgca cattttaatt atgtggtaaa aggtatatat gtacataaag tatgtccttt      2019
attcaggctt tttttctttt tttcttttttt ttatttttt gagacgaagt ttttgctctt      2079
gttgtccagg ctggagtgta atggcatgct cttggctcac cacaacctcc gcctcccggg     2139
ttcaagtgat tctcctgcct caacctcctg agtagctggg attacaggca tgcaccaaca     2199
tgccaggctg attttgtatt tttagtagag atggggtttc tccatgttgg tcaggctggt    2259
ctcgaacact cgacctcaag tgatccgccc acctcagcct cccaaagagc taggattaca     2319
ggcatgagcc accacaccca gctcagggct tattttctta ggctagattg ccaaggggag     2379
aattattatg tcaaagaaac tactattgg acaggaatct gaaaaggatg tgttttgggg      2439
ccatgtgtct cccaacattg ttatttctga aaagtaaatc acaacaaggc ccactctttc     2499
cctaggacct ctcgtagcct ggctcatcct gagtttctct ggataaatat tcctgagccc    2559
tgtgccttgg aaggggaagc tcactcacag acaagcccac taaagacagt ctctcttcct    2619 ttgtgtc cac cct cag gga aga ggc gtc ctg cca agg cct ggt cag gca       2668 gga gaa cca ggc tct gct gcc acc gag tcc cta gcc cca act caa caa       2716 acc tga aag gtaagtaccc ccacctcgtc cagactgtgg ggcagaagtt               2765
ctacagtggc catgggacca gccacacaca ctgatcagcc cccacccatg ctggcatca     2825 ggctctggct gggaggacat ctttgttttg ttgattaatt tgttgactcc cccccaaaag    2885
tcaacaaatt aatcatttta aactgaatac attctgccat ggaaaaaag caggatgcaa     2945 ttagcagatg ttgtgtggaa acacacttac tttaggtgga aggtgtctga gcaggtgaca    3005
tttatgagac ctggctcatt tatgagccag gagcctggct gaggcctgtg gaggtggggc    3065
atgcaggcag aggaggcagc aagggtgaag gcaagagtg gggtatggaa acagatggt       3125 agcagggctt gagaggtact cccagaagct aaggaccaaa gctgcctgtg aaccctgtgg    3185
acctggggca cagatcagca tgcaggtcac cagcagggga gtgggcctga ggtccagag     3245 agccatagct tggcaggaga taaggcagcc ccagagatgc cagcaggcag catccaggct    3305
gcatgaccag aacgaggccc agaagagcaa ggctgccctc tccctgaggc ctggggacac    3365
tgggaggcct gtggcggaca ggcccaagct caggagggct gcgggcaccc agttccctgc    3425
acaggggctg caggcccaga gcagatattc actggagttg cccagcccag gtggaagggt    3485
caggctgctg gagcttgggt agggcaggca gatccccaag gggagactgt ggaccctgag    3545
tcagacagcc tgacaccaac ctggggctcc tgcctgaact ctgcagcccc agtgcccact    3605
ctcaagaggc tgaggaggtc ccggcccac ttgctcctct gcggccatgg cccatggggt     3665
ccatgaccag cgccggagcc tccatgcctt cccagctac aaggggatg ctcagctgtg       3725 atgcaggaga gggatagagg gaggaagcaa gacagcatga ctccagccgc agaccttctc    3785
ccggagatgc tgcagcccct tcttccaaa ctggcatcac acccagccgg ccaggataaa      3845
aataaccagc tcgtcttcac cacgggctga aggatcccnn nnnnnnnnca cgaaaagccc    3905
```

```
cttctgggcc tccagggaaa agcataagat ctaattcttg ctttgaaatt ttttttaaa      3965 tgtgtttgaa aatgcaactt aattgtgttt tcctctctct ccccacaacc tggctctgac     4025
ctcgccatct tcctgtcctt gtccctcttg tctactcatt gctcctccca gga cat        4081 cat gtg agg ctc tgt aaa cca tgc aag ctt gag cca gag ccc cgc ctt      4129 tgg gtg gtg cct ggg gca ctc cca cag gtg                              4159
```

```
<210> SEQ ID NO 9
<211> LENGTH: 23
<212> TYPE: PRT
<213> ORGANISM: Homo sapiens

<400> SEQUENCE: 9

Met Arg Leu Leu Val Leu Ser Ser Leu Leu Cys Ile Leu Leu Leu Cys
  1               5                  10                  15

Phe Ser Ile Phe Ser Thr Glu
             20

<210> SEQ ID NO 10
<211> LENGTH: 30
<212> TYPE: PRT
<213> ORGANISM: Homo sapiens

<400> SEQUENCE: 10

Gly Lys Arg Arg Pro Ala Lys Ala Trp Ser Gly Arg Arg Thr Arg Leu
  1               5                  10                  15

Cys Cys His Arg Val Pro Ser Pro Asn Ser Thr Asn Leu Lys
             20                  25                  30

<210> SEQ ID NO 11
<211> LENGTH: 28
<212> TYPE: PRT
<213> ORGANISM: Homo sapiens

<400> SEQUENCE: 11

Gly His His Val Arg Leu Cys Lys Pro Cys Lys Leu Glu Pro Glu Pro
  1               5                  10                  15

Arg Leu Trp Val Val Pro Gly Ala Leu Pro Gln Val
             20                  25

<210> SEQ ID NO 12
<211> LENGTH: 11
<212> TYPE: PRT
<213> ORGANISM: Human immunodeficiency virus type 1

<400> SEQUENCE: 12

Tyr Gly Arg Lys Lys Arg Arg Gln Arg Arg Arg
  1               5                  10

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence:
      internalizing domain derived from HIV tat protein

<400> SEQUENCE: 13

Gly Gly Gly Gly Tyr Gly Arg Lys Lys Arg Arg Gln Arg Arg Arg
  1               5                  10                  15
```

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: PCR primer
      corresponding to human SECS-1

<400> SEQUENCE: 14
cccaactcaa caaacctgaa a                                           21

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence: PCR primer
      corresponding to human SECS-1

<400> SEQUENCE: 15
gggaccactg gatgctg                                                17

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: PCR primer
      corresponding to murine SECS-1

<400> SEQUENCE: 16
actccggctc cttcactatg a                                           21

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: PCR primer
      corresponding to murine SECS-1

<400> SEQUENCE: 17
atgtgggcat catcaacgct tta                                         23

<210> SEQ ID NO 18
<211> LENGTH: 42
<212> TYPE: DNA
<213> ORGANISM: Artificial Sequence
<220> FEATURE:
<223> OTHER INFORMATION: Description of Artificial Sequence: PCR primer
      corresponding to human SECS-1

<400> SEQUENCE: 18
aaataacata tgaaacgtcg tccagctaaa gcctggtcag gc                    42

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence: PCR primer
      corresponding to human SECS-1

<400> SEQUENCE: 19
ggtgatggtg atggtgcacc tgtgggagtg cccc                             34

<210> SEQ ID NO 20

```
<211> LENGTH: 37
<212> TYPE: DNA
<213> ORGANISM: Artificial Sequence
<220> FEATURE:
<223> OTHER INFORMATION: Description of Artificial Sequence: PCR primer
      corresponding to human SECS-1

<400> SEQUENCE: 20
gtggtagtgg tagtggtagt aactatccta ggtattt                             37

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: SECS-1 antigen

<400> SEQUENCE: 21

Cys Trp Val Val Pro Gly Ala Leu Pro Gln Ile
  1               5                  10

<210> SEQ ID NO 22
<211> LENGTH: 81
<212> TYPE: PRT
<213> ORGANISM: Artificial Sequence
<220> FEATURE:
<223> OTHER INFORMATION: Description of Artificial Sequence: artificial
      Secs-1 polypeptide sequence generated from an amino acid sequence
      comparison of the human, murine, and rat Secs-1 polypeptides
<220> FEATURE:
<221> NAME/KEY: UNSURE
<222> LOCATION: (5)
<223> OTHER INFORMATION: "Xaa" can be any naturally occurring amino acid
<220> FEATURE:
<221> NAME/KEY: UNSURE
<222> LOCATION: (8)
<223> OTHER INFORMATION: "Xaa" can be any naturally occurring amino acid
<220> FEATURE:
<221> NAME/KEY: UNSURE
<222> LOCATION: (10)
<223> OTHER INFORMATION: "Xaa" can be any naturally occurring amino acid
<220> FEATURE:
<221> NAME/KEY: UNSURE
<222> LOCATION: (11)
<223> OTHER INFORMATION: "Xaa" can be any naturally occurring amino acid
<220> FEATURE:
<221> NAME/KEY: UNSURE
<222> LOCATION: (12)
<223> OTHER INFORMATION: "Xaa" can be either methionine or isoleucine
<220> FEATURE:
<221> NAME/KEY: UNSURE
<222> LOCATION: (14)
<223> OTHER INFORMATION: "Xaa" can be any naturally occurring amino acid
<220> FEATURE:
<221> NAME/KEY: UNSURE
<222> LOCATION: (17)
<223> OTHER INFORMATION: "Xaa" can be any naturally occurring amino acid
<220> FEATURE:
<221> NAME/KEY: UNSURE
<222> LOCATION: (18)
<223> OTHER INFORMATION: "Xaa" can be either cysteine or serine
<220> FEATURE:
<221> NAME/KEY: UNSURE
<222> LOCATION: (19)
<223> OTHER INFORMATION: "Xaa" can be either isoleucine or valine
<220> FEATURE:
<221> NAME/KEY: UNSURE
<222> LOCATION: (20)
<223> OTHER INFORMATION: "Xaa" can be any naturally occurring amino acid
<220> FEATURE:
<221> NAME/KEY: UNSURE
<222> LOCATION: (22)
<223> OTHER INFORMATION: "Xaa" can be either serine or threonine
<220> FEATURE:
<221> NAME/KEY: UNSURE
```

```
<222> LOCATION: (25)
<223> OTHER INFORMATION: "Xaa" can be either arginine or lysine
<220> FEATURE:
<221> NAME/KEY: UNSURE
<222> LOCATION: (26)
<223> OTHER INFORMATION: "Xaa" can be either arginine or lysine
<220> FEATURE:
<221> NAME/KEY: UNSURE
<222> LOCATION: (27)
<223> OTHER INFORMATION: "Xaa" can be either histidine or arginine
<220> FEATURE:
<221> NAME/KEY: UNSURE
<222> LOCATION: (31)
<223> OTHER INFORMATION: "Xaa" can be any naturally occurring amino acid
<220> FEATURE:
<221> NAME/KEY: UNSURE
<222> LOCATION: (32)
<223> OTHER INFORMATION: "Xaa" can be any naturally occurring amino acid
<220> FEATURE:
<221> NAME/KEY: UNSURE
<222> LOCATION: (33)
<223> OTHER INFORMATION: "Xaa" can be any naturally occurring amino acid
<220> FEATURE:
<221> NAME/KEY: UNSURE
<222> LOCATION: (34)
<223> OTHER INFORMATION: "Xaa" can be any naturally occurring amino acid
<220> FEATURE:
<221> NAME/KEY: UNSURE
<222> LOCATION: (36)
<223> OTHER INFORMATION: "Xaa" can be any naturally occurring amino acid
<220> FEATURE:
<221> NAME/KEY: UNSURE
<222> LOCATION: (37)
<223> OTHER INFORMATION: "Xaa" can be any naturally occurring amino acid
    or may be absent
<220> FEATURE:
<221> NAME/KEY: UNSURE
<222> LOCATION: (38)
<223> OTHER INFORMATION: "Xaa" can be any naturally occurring amino acid
    or may be absent
<220> FEATURE:
<221> NAME/KEY: UNSURE
<222> LOCATION: (39)
<223> OTHER INFORMATION: "Xaa" can be any naturally occurring amino acid
    or may be absent
<220> FEATURE:
<221> NAME/KEY: UNSURE
<222> LOCATION: (40)
<223> OTHER INFORMATION: "Xaa" can be any naturally occurring amino acid
<220> FEATURE:
<221> NAME/KEY: UNSURE
<222> LOCATION: (43)
<223> OTHER INFORMATION: "Xaa" can be any naturally occurring amino acid
<220> FEATURE:
<221> NAME/KEY: UNSURE
<222> LOCATION: (44)
<223> OTHER INFORMATION: "Xaa" can be any naturally occurring amino acid
<220> FEATURE:
<221> NAME/KEY: UNSURE
<222> LOCATION: (46)
<223> OTHER INFORMATION: "Xaa" can be any naturally occurring amino acid
<220> FEATURE:
<221> NAME/KEY: UNSURE
<222> LOCATION: (47)
<223> OTHER INFORMATION: "Xaa" can be any naturally occurring amino acid
<220> FEATURE:
<221> NAME/KEY: UNSURE
<222> LOCATION: (48)
<223> OTHER INFORMATION: "Xaa" can be any naturally occurring amino acid
<220> FEATURE:
<221> NAME/KEY: UNSURE
<222> LOCATION: (49)
<223> OTHER INFORMATION: "Xaa" can be any naturally occurring amino acid
<220> FEATURE:
<221> NAME/KEY: UNSURE
<222> LOCATION: (50)
<223> OTHER INFORMATION: "Xaa" can be any naturally occurring amino acid
<220> FEATURE:
<221> NAME/KEY: UNSURE
```

```
<222> LOCATION: (51)
<223> OTHER INFORMATION: "Xaa" can be either threonine or asparagine
<220> FEATURE:
<221> NAME/KEY: UNSURE
<222> LOCATION: (52)
<223> OTHER INFORMATION: "Xaa" can be any naturally occurring amino acid
<220> FEATURE:
<221> NAME/KEY: UNSURE
<222> LOCATION: (55)
<223> OTHER INFORMATION: "Xaa" can be either asparagine or histidine
<220> FEATURE:
<221> NAME/KEY: UNSURE
<222> LOCATION: (57)
<223> OTHER INFORMATION: "Xaa" can be any naturally occurring amino acid
<220> FEATURE:
<221> NAME/KEY: UNSURE
<222> LOCATION: (59)
<223> OTHER INFORMATION: "Xaa" can be any naturally occurring amino acid
<220> FEATURE:
<221> NAME/KEY: UNSURE
<222> LOCATION: (61)
<223> OTHER INFORMATION: "Xaa" can be either arginine or lysine
<220> FEATURE:
<221> NAME/KEY: UNSURE
<222> LOCATION: (62)
<223> OTHER INFORMATION: "Xaa" can be any naturally occurring amino acid
<220> FEATURE:
<221> NAME/KEY: UNSURE
<222> LOCATION: (64)
<223> OTHER INFORMATION: "Xaa" can be either arginine or lysine
<220> FEATURE:
<221> NAME/KEY: UNSURE
<222> LOCATION: (65)
<223> OTHER INFORMATION: "Xaa" can be any naturally occurring amino acid
      or may be absent
<220> FEATURE:
<221> NAME/KEY: UNSURE
<222> LOCATION: (66)
<223> OTHER INFORMATION: "Xaa" can be any naturally occurring amino acid
<220> FEATURE:
<221> NAME/KEY: UNSURE
<222> LOCATION: (67)
<223> OTHER INFORMATION: "Xaa" can be any naturally occurring amino acid
<220> FEATURE:
<221> NAME/KEY: UNSURE
<222> LOCATION: (68)
<223> OTHER INFORMATION: "Xaa" can be any naturally occurring amino acid
<220> FEATURE:
<221> NAME/KEY: UNSURE
<222> LOCATION: (69)
<223> OTHER INFORMATION: "Xaa" can be any naturally occurring amino acid
<220> FEATURE:
<221> NAME/KEY: UNSURE
<222> LOCATION: (70)
<223> OTHER INFORMATION: "Xaa" can be any naturally occurring amino acid
<220> FEATURE:
<221> NAME/KEY: UNSURE
<222> LOCATION: (71)
<223> OTHER INFORMATION: "Xaa" can be any naturally occurring amino acid
<220> FEATURE:
<221> NAME/KEY: UNSURE
<222> LOCATION: (81)
<223> OTHER INFORMATION: "Xaa" can be either isoleucine or valine

<400> SEQUENCE: 22

Met Arg Leu Leu Xaa Leu Ser Xaa Leu Xaa Xaa Xaa Leu Xaa Leu Cys
 1               5                  10                  15

Xaa Xaa Xaa Xaa Ser Xaa Glu Gly Xaa Xaa Xaa Pro Ala Lys Xaa Xaa
            20                  25                  30

Xaa Xaa Arg Xaa Xaa Xaa Xaa Xaa Cys His Xaa Xaa Pro Xaa Xaa Xaa
        35                  40                  45

Xaa Xaa Xaa Xaa Lys Gly Xaa His Xaa Arg Xaa Cys Xaa Xaa Cys Xaa
    50                  55                  60
```

```
Xaa Xaa Xaa Xaa Xaa Xaa Xaa Trp Val Val Pro Gly Ala Leu Pro Gln
 65                  70                  75                  80

Xaa
```